US008598140B2

(12) United States Patent
Schneider et al.

(10) Patent No.: US 8,598,140 B2
(45) Date of Patent: Dec. 3, 2013

(54) APTAMERS TO β-NGF AND THEIR USE IN TREATING β-NGF MEDIATED DISEASES AND DISORDERS

(75) Inventors: Daniel J. Schneider, Arvada, CO (US); Akihiko Hisaminato, Osaka (JP); Sheela Waugh, Erie, CO (US); Daniel Resnicow, Boulder, CO (US); Akira Nagabukuro, Osaka (JP); Toshihide Ono, Osaka (JP)

(73) Assignees: SomaLogic, Inc., Boulder, CO (US); OTSUKA Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/634,618

(22) PCT Filed: Apr. 12, 2011

(86) PCT No.: PCT/US2011/032017
§ 371 (c)(1),
(2), (4) Date: Sep. 13, 2012

(87) PCT Pub. No.: WO2011/130195
PCT Pub. Date: Oct. 20, 2011

(65) Prior Publication Data
US 2013/0012693 A1    Jan. 10, 2013

Related U.S. Application Data

(60) Provisional application No. 61/323,145, filed on Apr. 12, 2010.

(51) Int. Cl.
*A61K 48/00* (2006.01)

(52) U.S. Cl.
USPC .................................................. 514/44 R

(58) Field of Classification Search
None
See application file for complete search history.

(56) References Cited

U.S. PATENT DOCUMENTS

| | | |
|---|---|---|
| 4,711,955 A | 12/1987 | Ward |
| 4,737,453 A | 4/1988 | Primus et al. |
| 4,752,566 A | 6/1988 | Collins et al. |
| 4,948,882 A | 8/1990 | Ruth |
| 5,270,163 A | 12/1993 | Gold et al. |
| 5,412,087 A | 5/1995 | McGall et al. |
| 5,428,149 A | 6/1995 | Eaton |
| 5,475,096 A | 12/1995 | Gold et al. |
| 5,476,766 A | 12/1995 | Gold et al. |
| 5,496,938 A | 3/1996 | Gold et al. |
| 5,567,588 A | 10/1996 | Gold et al. |
| 5,580,972 A | 12/1996 | Tu |
| 5,582,981 A | 12/1996 | Toole et al. |
| 5,595,877 A | 1/1997 | Gold et al. |
| 5,599,720 A | 2/1997 | Ekins et al. |
| 5,660,985 A | 8/1997 | Pieken et al. |
| 5,719,273 A | 2/1998 | Tu et al. |
| 5,840,867 A * | 11/1998 | Toole et al. ............... 536/23.1 |
| 5,861,254 A | 1/1999 | Schneider et al. |
| 5,945,527 A | 8/1999 | Tu et al. |
| 5,958,691 A | 9/1999 | Pieken |
| 5,962,225 A | 10/1999 | Ramberg |
| 6,020,483 A | 2/2000 | Beckvermit et al. |
| 6,175,001 B1 | 1/2001 | Barbas et al. |
| 6,344,318 B1 | 2/2002 | Gold et al. |
| 6,346,611 B1 | 2/2002 | Pagratis et al. |
| 6,734,172 B2 | 5/2004 | Scholler et al. |
| 7,855,054 B2 | 12/2010 | Schneider et al. |
| 7,947,447 B2 | 5/2011 | Zichi et al. |
| 2003/0054360 A1 | 3/2003 | Gold et al. |
| 2004/0120891 A1 | 6/2004 | Hill et al. |
| 2004/0176282 A1 | 9/2004 | Dalby et al. |
| 2005/0142582 A1 | 6/2005 | Doyle et al. |
| 2005/0288244 A1 | 12/2005 | Manoharan et al. |
| 2006/0105341 A1 | 5/2006 | Krause et al. |
| 2007/0003950 A1 | 1/2007 | Shen et al. |
| 2007/0161015 A1 | 7/2007 | Zheng et al. |
| 2007/0286915 A1 | 12/2007 | Tonogaito et al. |
| 2008/0207523 A1 | 8/2008 | Friebe et al. |
| 2009/0004667 A1 | 1/2009 | Zichi et al. |
| 2010/0285479 A1 | 11/2010 | Jenison |
| 2010/0317120 A1 | 12/2010 | Heil et al. |
| 2011/0136099 A1 | 6/2011 | Schneider et al. |
| 2011/0245479 A1 | 10/2011 | Zichi et al. |
| 2011/0251266 A1 | 10/2011 | Jin et al. |

FOREIGN PATENT DOCUMENTS

| | | |
|---|---|---|
| GB | 2 183 661 | 6/1987 |
| WO | WO 92/14842 | 3/1992 |
| WO | WO 92/14843 | 9/1992 |
| WO | WO2010/035725 | 4/2010 |
| WO | WO2011/118682 | 9/2011 |

OTHER PUBLICATIONS

Bock et al., (1992) Nature 355:564-565 "Selection of Single-Stranded DNA Molecules That Bind and Inhibit Human Thrombin".
Binkley, Jonathan, et al. (1995) Nucleic Acids Res., vol. 23, No. 16, p. 3198-3205, "RNA ligands to human nerve growth factor."
Daniels et al. (Dec. 23, 2003) PNAS 100(26):15416-15421, "A tenascin-C aptamer identified by tumor cell SELEX: Systematic evolution of ligands by exponential enrichment".
DiDonato (2006) "Dissertation. Part II. Synthesis and Evaluation of Modified Nucleotides for DNA Aptamer Selection" University of North Carolina, Raleigh 30-53.
Drabovich et al. (May 1, 2006) Analytical Chemistry 78(9):3171-3178, "Selection of smart aptamers by methods of kinetic capillary electrophoresis".
Eaton et al. (1997) Bioorganic & Medicinal Chemistry 5(6):1087-1096, "Post—SELEX Combinatorial Optimization of Aptamers".
Ekins and Chu (Sep. 1997) JIFCC 9(3):100-109, "Immunoassay and Other Ligand Assays: Present Status and Future Trends".

*Primary Examiner* — Tracy Vivlemore
*Assistant Examiner* — Kate Poliakova
(74) *Attorney, Agent, or Firm* — Swanson & Bratschun, L.L.C.

(57) ABSTRACT

The present disclosure relates generally to the field of nucleic acids and, more particularly, to aptamers capable of binding to β-NGF; pharmaceutical compositions comprising such β-NGF aptamers; and methods of making and using the same.

17 Claims, 15 Drawing Sheets

(56) References Cited

OTHER PUBLICATIONS

Ellington & Szostak (1990) "Selection of RNAs with ligand-specific binding activity from pools of random sequence molecules" RNA Processing meeting abstract, p. 84.
Famulok and Szostak (1992) "In vitro Selection of Specific Ligand-binding Nucleic Acids" Angew. Chem. Int. Ed. Engl. 31(8):979-988.
Gebhardt et al. (Jun. 20, 2000) Biochemistry 39(24):7255-7265, "RNA aptamers to S-adenosylhomocysteine: kinectic properties, divalent cation dependency, and comparision with anti-S-adenosylhomocysteine antibody".
Gold et al. (Jan. 1, 1995) Harvey Lectures 91:47-57, "The SELEX Process: A Surprising Source of Therapeutic and Diagnostic Compounds".
ISR and Written Opinion mailed Jun. 17, 2011 in PCT/US2011/032017.
International Preliminary Report on Patentability mailed Oct. 26, 2012 in PCT/US2011/032017.
Jhaveri et al. (Sep. 1998) "In vitro Selection of Phosphorothiolated Aptamers" Bioorganic & Medicinal Chemistry Letters 8:2285-2290.
Joyce (1989) Gene 82:83-87, "Amplification, mutation and selection of catalytic RNA".
Joyce and Inoue (1989) Nucleic Acids Research 17(2): 711-722, "A novel technique for the rapid preparation of mutant RNAs".
Kinzler and Vogelstein (1989) Nucleic Acids Research 17(10): 3645-3653, "Whole genome PCR: application to the identification of sequences bound by gene regulatory proteins".
Kramer et al. (1974) J. Mol. Biol. 89: 719-736, "Evolution in vitro: sequence and phenotype of a mutant RNA resistant to ethidium bromide".
Langer et al. (Nov. 1981) Proc. Natl. Acad. Sci. USA,78(11):6633-6637, "Enzymatic synthesis of biotin-labeled polynucleotides: Novel nucleic acid affinity probes".
Latham et al. (1994) Nucleic Acids Research 22(14):2817-2822, "The application of a modified nucleotide in aptamer selection: novel thrombin aptamers containing 5-(1-pentynyl)-2'-deoxyuridine".
Levisohn and Spiegleman (1968) PNAS USA 60: 866-872, "The cloning of a self-replicating RNA molecule".
Levisohn and Spiegleman (1969) PNAS USA 63: 805-811, "Further extracellular Darwinian experiments with replicating RNA moleucles: diverse variants isolated under different selective conditions".
McGown et al. (Nov. 1995) Anal. Chem. 67:663A-668A, "The Nucleic Acid Ligand. A New Tool for Molecular Recognition".
Oliphant and Struhl (1987) Methods in Enzymology 155: 568-582, "The use of random-sequence oligonucleotides for determining consensus sequences".
Oliphant and Struhl (1988) Nucleic Acids Research 16(15): 7673-7683, "Defining the consensus sequences of E. coli promoter elements by random selection".
Oliphant et al. (1986) Gene 44:177-183, "Cloning of random-sequence oligodeoxynucleotides".
Oliphant et al. (Jul. 1989) Mol. Cell. Biol. 9: 2944-2949, "Defining the sequence specificity of DNA-binding proteins by selecting binding sites from random-sequence oligonucleotides: analysis of yeast GCN4 protein".
Osborne et al. (1997) Current Opinion in Chemical Biology 1:5-9, "Aptamers as Therapeutic and Diagnostic Reagents: Problems and Prospects".
Robertson and Joyce (Mar. 1990) Nature 344: 467-468, "Selection in vitro of an RNA enzyme that specifically cleaves single-stranded DNA".
Schoetzau et al. (2003) Bioconjugate Chemistry 14:919-926, "Aminomodified Nucleobases: Functionalized Nucleoside Triphosphates Applicable for SELEX".
Syvanen et al. (1986) Nucleic Acid Research, 14(12):5037-5048, "Fast quantification of nucleic acid hybrids by affinity-based hybrid collection".
Szostak (1988) Redesigning the Molecules of Life, (S.A. Benner ed.) Springer-Verlag Berlin Heidelberg, pp. 87-113.
Tarasow (1998) Nucleic Acid Sciences 48(1):29-37, Dressed for Success "Realizing the Catalytic Potential of RNA".
Thiesen and Bach (Jun. 1990) Nucleic Acids Res. 18(11): 3203-3209, "Target detection assay (TDA): a versatile procedure to determine DNA binding sites as demonstrated on SP1 protein".
Tuerk and Gold (Aug. 1990) Science 249: 505-510, "Systematic evolution of ligands by exponential enrichment: RNA ligands to bacteriophage T4 DNA polymerase".
Vaught et al. (Mar. 2010) J.Am. Chem. Soc. ePub, 132(12):4141-4151:4142, "Expanding the Chemistry of DNA for In Vitro Selection".
Vaught, Jonathan David, Thesis Oct. 2008, "Enhancing the Functionality of Nucleic Acids".
Zichi et al. (Mar. 7, 2008) Current Opinion in Chemical Biology 12(1):78-85, "Proteomics and diagnostics: Let's Get Specific, again".
Bartel et al. (1991) Cell 67:529-536, "HIV-1 Rev Regulation Involves Recognition of Non-Watson-Crick Base Pairs in Viral RNA".

* cited by examiner

FIG. 2A

Row (A)

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|---|---|---|---|---|---|---|---|---|---|---|
| A | 0 | 92 | 0 | 0 | 61 | 0 | 0 | 75 | 2 | 1 | 0 | 0 | 0 | 1 | 0 | 0 | 0 | 1 | 96 | 13 | 0 | 0 | 3 | 0 | 0 | 20 | 0 | 1 |
| Z | 23 | 0 | 99 | 1 | 0 | 2 | 3 | 2 | 0 | 97 | 97 | 2 | 0 | 0 | 0 | 99 | 99 | 87 | 0 | 13 | 0 | 0 | 1 | 94 | 93 | 0 | 89 | 7 |
| G | 17 | 7 | 0 | 98 | 38 | 97 | 96 | 20 | 10 | 0 | 2 | 97 | 99 | 98 | 96 | 0 | 0 | 7 | 2 | 71 | 0 | 1 | 89 | 0 | 0 | 0 | 0 | 62 |
| C | 57 | 0 | 0 | 0 | 0 | 0 | 0 | 0 | 86 | 0 | 0 | 0 | 0 | 0 | 0 | 0 | 0 | 0 | 0 | 0 | 97 | 93 | 0 | 0 | 0 | 71 | 0 | 0 |
| T | | | | | | | | | | | • | | | | | | | • | | | | | | | | | | 6 |

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|---|---|---|---|---|---|---|---|---|---|---|
| Consensus | B | A | Z | G | R | G | G | R | S | Z | W | G | G | G | G | Z | Z | W | A | D | C | C | G | Z | Z | R | Z | G |

Row (A) indicates the frequency at which A is observed in the 2426-66 aptamer family at each of the 28 conserved positions
Row (Z) indicates the frequency at which Z is observed in the 2426-66 aptamer family at each of the 28 conserved positions
Row (G) indicates the frequency at which G is observed in the 2426-66 aptamer family at each of the 28 conserved positions
Row (C) indicates the frequency at which C is observed in the 2426-66 aptamer family at each of the 28 conserved positions
Row (T) indicates the only two conserved Z positions that can be replaced with T with no loss of β-NGF binding activity (•)

Row (Consensus) is the consensus sequence for the aptamer with the BzdU substitution, where:

Z = modified U
B = any nucleotide other than A
R = A or G
S = C or G
W = Z or T
D = any nucleotide other than C

FIG. 2B

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|---|---|---|---|---|---|---|---|---|---|---|---|---|---|---|---|---|
| A | 0 | 92 | 0 | 0 | 0 | 51 | 0 | 0 | 0 | 75 | 2 | 0 | 1 | 0 | 0 | 0 | 1 | 0 | 0 | 0 | 0 | 1 | 96 | 13 | 0 | 0 | 0 | 3 | 0 | 0 | 0 | 20 | 0 | 1 |
| Z | 23 | 0 | 0 | 99 | 1 | 0 | 1 | 2 | 3 | 2 | 0 | 1 | 97 | 97 | 2 | 0 | 0 | 0 | 0 | 99 | 99 | 87 | 0 | 13 | 0 | 0 | 0 | 1 | 94 | 93 | 0 | 0 | 89 | 7 |
| G | 17 | 7 | 1 | 0 | 98 | 38 | 0 | 97 | 96 | 20 | 10 | 6 | 0 | 2 | 97 | 99 | 98 | 96 | 3 | 0 | 0 | 7 | 2 | 71 | 0 | 0 | 1 | 89 | 0 | 0 | 1 | 71 | 0 | 62 |
| C | 57 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 97 | 97 | 93 | 0 | 0 | 0 | 0 | 0 | 0 | 6 |
| - | 0 | 0 | 98 | 0 | 0 | 0 | 97 | 0 | 0 | 0 | 86 | 91 | 0 | 0 | 0 | 0 | 0 | 3 | 95 | 0 | 0 | 3 | 0 | 0 | 0 | 1 | 2 | 4 | 4 | 6 | 98 | 6 | 8 | 20 |
| Consensus | B | A | - | Z | G | R | - | G | G | R | S | - | Z | Z | G | G | G | G | - | Z | Z | Z | A | D | - | C | C | G | Z | Z | - | R | Z | G |

Row (A) indicates the frequency at which A is observed in the 2426-66 aptamer family at each of the 34 conserved positions
Row (Z) indicates the frequency at which Z is observed in the 2426-66 aptamer family at each of the 34 conserved positions
Row (G) indicates the frequency at which G is observed in the 2426-66 aptamer family at each of the 34 conserved positions
Row (C) indicates the frequency at which C is observed in the 2426-66 aptamer family at each of the 34 conserved positions
Row (-) indicates the frequency at which a deletion is observed in the 2426-66 aptamer family at each of the 34 conserved positions Row (Consensus) is the consensus sequence for the aptamer with the BzdU substitution, where:

Z = modified U
B = C, G or Z
R = A or G
S = C or G
D = A, G or Z

FIG. 3

Dimerization Strategy #1

Head-to-tail NGF Dimers

Hexaethylene glycol (HEG) is ~22 Å

[5' 28mer 3'] — HEG — [5' 28mer 3'] — Inv dT
[5' 28mer 3'] — HEG — HEG — [5' 28mer 3'] — Inv dT
[5' 28mer 3'] — HEG — HEG — HEG — [5' 28mer 3'] — Inv dT
[5' 28mer 3'] — HEG — HEG — HEG — HEG — [5' 28mer 3'] — Inv dT X = abasic sugar phosphate linkage (~3 Å each)

[5' 28mer 3'] — $X_5$ — [5' 28mer 3'] — Inv dT
[5' 28mer 3'] — $X_{10}$ — [5' 28mer 3'] — Inv dT
[5' 28mer 3'] — $X_{15}$ — [5' 28mer 3'] — Inv dT
[5' 28mer 3'] — $X_{20}$ — [5' 28mer 3'] — Inv dT Dimerization Strategy #2

Base = Uridine (U) or Cytidine(C) (attachment is to the 5-position)
K = R' group plus $(CH_2)_n$ connecting group, where n = 0-3

FIG. 10 continued wherein

R"" is selected from the group consisting of a branched or linear lower alkyl (C1-C20); halogen (F, Cl, Br, I); nitrile (CN); boronic acid ($BO_2H_2$); carboxylic acid (COOH); carboxylic acid ester (COOR"); primary amide ($CONH_2$); secondary amide (CONHR"); tertiary amide (CONR"R'"); sulfonamide ($SO_2NH_2$); N-alkylsulfonamide (SONHR");

wherein

R", R'" are independently selected from a group consisting of a branched or linear lower alkyl (C1-C2)); phenyl (C6H5); an R"" substituted phenyl ring (R""C6H4); wherein R"" is defined above; a carboxylic acid (COOH); a carboxylic acid ester (COOR""); wherein R"" is a branched or linear lower alkyl (C1-C20); and cycloalkyl; wherein R" = R'" = (CH2)n;

wherein n =2-10.

SEQUENCE LISTING

<160> NUMBER OF SEQ ID NOS: 169

<210> SEQ ID NO 1
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (30)..(30)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (43)..(45)
<223> OTHER INFORMATION: 5-(N-benzylcarboxyamide)-2'-deoxyuridine
<220> FEATURE:
<221> NAME/KEY: misc_feature
<222> LOCATION: (51)..(52)
<223> OTHER INFORMATION: 5-(N-benzylcarboxyamide)-2'-deoxyuridine
<220> FEATURE:
<221> NAME/KEY: misc_feature
<222> LOCATION: (54)..(54)
<223> OTHER INFORMATION: 5-(N-benzylcarboxyamide)-2'-deoxyuridine

<400> SEQUENCE: 1
gagtgaccgt ctgcctgcag cgggacacan gaggacnngg ggnnnagccg nngnggcaca      60
gagaagaaac aagacc                                                     76

<210> SEQ ID NO 2
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 5-(N-benzylcarboxyamide)-2'-deoxyuridine
<220> FEATURE:
<221> NAME/KEY: misc_feature
<222> LOCATION: (10)..(11)
<223> OTHER INFORMATION: 5-(N-benzylcarboxyamide)-2'-deoxyuridine
<220> FEATURE:
<221> NAME/KEY: misc_feature -continued

```
<222> LOCATION: (16)..(18)
<223> OTHER INFORMATION: 5-(N-benzylcarboxyamide)-2'-deoxyuridine
<220> FEATURE:
<221> NAME/KEY: misc_feature
<222> LOCATION: (24)..(25)
<223> OTHER INFORMATION: 5-(N-benzylcarboxyamide)-2'-deoxyuridine
<220> FEATURE:
<221> NAME/KEY: misc_feature
<222> LOCATION: (27)..(27)
<223> OTHER INFORMATION: 5-(N-benzylcarboxyamide)-2'-deoxyuridine

<400> SEQUENCE: 2
cangaggacn ngggnnnag ccgnngng                                       28

<210> SEQ ID NO 3
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: a C, G, or Independently selected from a
      modified nucleotide, specifically a modified pyrimidine
<220> FEATURE:
<221> NAME/KEY: misc_feature
<222> LOCATION: (3)..(3)
<223> OTHER INFORMATION: Independently selected from a modified
      nucleotide, specifically a modified pyrimidine
<220> FEATURE:
<221> NAME/KEY: misc_feature
<222> LOCATION: (5)..(5)
<223> OTHER INFORMATION: an A or G
<220> FEATURE:
<221> NAME/KEY: misc_feature
<222> LOCATION: (8)..(8)
<223> OTHER INFORMATION: an A or G
<220> FEATURE:
<221> NAME/KEY: misc_feature
<222> LOCATION: (9)..(9)
<223> OTHER INFORMATION: a C or G
<220> FEATURE:
<221> NAME/KEY: misc_feature
<222> LOCATION: (10)..(11)
<223> OTHER INFORMATION: Independently selected from a modified
      nucleotide, specifically a modified pyrimidine
<220> FEATURE:
<221> NAME/KEY: misc_feature
<222> LOCATION: (16)..(18)
<223> OTHER INFORMATION: Independently selected from a modified
      nucleotide, specifically a modified pyrimidine
<220> FEATURE:
<221> NAME/KEY: misc_feature
<222> LOCATION: (20)..(20)
<223> OTHER INFORMATION: an A, G, or Independently selected from a
      modified nucleotide, specifically a modified pyrimidine
<220> FEATURE:
<221> NAME/KEY: misc_feature
<222> LOCATION: (24)..(25)
<223> OTHER INFORMATION: Independently selected from a modified
      nucleotide, specifically a modified pyrimidine
<220> FEATURE:
<221> NAME/KEY: misc_feature
<222> LOCATION: (26)..(26)
<223> OTHER INFORMATION: an A or G
<220> FEATURE:
<221> NAME/KEY: misc_feature
<222> LOCATION: (27)..(27)
<223> OTHER INFORMATION: Independently selected from a modified
      nucleotide, specifically a modified pyrimidine

<400> SEQUENCE: 3
nangnggnnn ngggnnnan ccgnnnng                                       28

<210> SEQ ID NO 4
```

```
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (30)..(30)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (43)..(45)
<223> OTHER INFORMATION: 5-(N-benzylcarboxyamide)-2'-deoxyuridine

<400> SEQUENCE: 4
gagtgaccgt ctgcctgcag cgggacacan gaggacnngg ggnnnagccg            50

<210> SEQ ID NO 5
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(29)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (42)..(44)
<223> OTHER INFORMATION: 5-(N-benzylcarboxyamide)-2'-deoxyuridine
<220> FEATURE:
<221> NAME/KEY: misc_feature
<222> LOCATION: (50)..(50)
<223> OTHER INFORMATION: 5-(N-benzylcarboxyamide)-2'-deoxyuridine

<400> SEQUENCE: 5
agtgaccgtc tgcctgcagc gggacacang aggacnnggg gnnnagccgn            50

<210> SEQ ID NO 6
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (28)..(28)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (41)..(43)
<223> OTHER INFORMATION: 5-(N-benzylcarboxyamide)-2'-deoxyuridine
<220> FEATURE:
<221> NAME/KEY: misc_feature
<222> LOCATION: (49)..(50)
<223> OTHER INFORMATION: 5-(N-benzylcarboxyamide)-2'-deoxyuridine

<400> SEQUENCE: 6
gtgaccgtct gcctgcagcg ggacacanga ggacnngggg nnnagccgnn            50

<210> SEQ ID NO 7
```

```
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (27)..(27)
<223> OTHER INFORMATION: 5-(N-benzylcarboxyamide)-2'-deoxyuridine
<220> FEATURE:
<221> NAME/KEY: misc_feature
<222> LOCATION: (34)..(35)
<223> OTHER INFORMATION: 5-(N-benzylcarboxyamide)-2'-deoxyuridine
<220> FEATURE:
<221> NAME/KEY: misc_feature
<222> LOCATION: (40)..(42)
<223> OTHER INFORMATION: 5-(N-benzylcarboxyamide)-2'-deoxyuridine
<220> FEATURE:
<221> NAME/KEY: misc_feature
<222> LOCATION: (48)..(49)
<223> OTHER INFORMATION: 5-(N-benzylcarboxyamide)-2'-deoxyuridine

<400> SEQUENCE: 7
tgaccgtctg cctgcagcgg gacacangag gacnnggggn nnagccgnng         50

<210> SEQ ID NO 8
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: 5-(N-benzylcarboxyamide)-2'-deoxyuridine
<220> FEATURE:
<221> NAME/KEY: misc_feature
<222> LOCATION: (33)..(34)
<223> OTHER INFORMATION: 5-(N-benzylcarboxyamide)-2'-deoxyuridine
<220> FEATURE:
<221> NAME/KEY: misc_feature
<222> LOCATION: (39)..(41)
<223> OTHER INFORMATION: 5-(N-benzylcarboxyamide)-2'-deoxyuridine
<220> FEATURE:
<221> NAME/KEY: misc_feature
<222> LOCATION: (47)..(48)
<223> OTHER INFORMATION: 5-(N-benzylcarboxyamide)-2'-deoxyuridine

<400> SEQUENCE: 8
gaccgtctgc ctgcagcggg acacangagg acnnggggnn nagccgnngt         50

<210> SEQ ID NO 9
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(25)
<223> OTHER INFORMATION: 5-(N-benzylcarboxyamide)-2'-deoxyuridine
<220> FEATURE:
<221> NAME/KEY: misc_feature
<222> LOCATION: (32)..(33)
<223> OTHER INFORMATION: 5-(N-benzylcarboxyamide)-2'-deoxyuridine
<220> FEATURE:
<221> NAME/KEY: misc_feature
<222> LOCATION: (38)..(40)
<223> OTHER INFORMATION: 5-(N-benzylcarboxyamide)-2'-deoxyuridine
<220> FEATURE:
<221> NAME/KEY: misc_feature
<222> LOCATION: (46)..(47)
<223> OTHER INFORMATION: 5-(N-benzylcarboxyamide)-2'-deoxyuridine
<220> FEATURE:
<221> NAME/KEY: misc_feature
<222> LOCATION: (49)..(49)
```

<223> OTHER INFORMATION: 5-(N-benzylcarboxyamide)-2'-deoxyuridine

<400> SEQUENCE: 9
accgtctgcc tgcagcggga cacangagga cnnggggnnn agccgnngng    50

<210> SEQ ID NO 10
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 5-(N-benzylcarboxyamide)-2'-deoxyuridine
<220> FEATURE:
<221> NAME/KEY: misc_feature
<222> LOCATION: (31)..(32)
<223> OTHER INFORMATION: 5-(N-benzylcarboxyamide)-2'-deoxyuridine
<220> FEATURE:
<221> NAME/KEY: misc_feature
<222> LOCATION: (37)..(39)
<223> OTHER INFORMATION: 5-(N-benzylcarboxyamide)-2'-deoxyuridine
<220> FEATURE:
<221> NAME/KEY: misc_feature
<222> LOCATION: (45)..(46)
<223> OTHER INFORMATION: 5-(N-benzylcarboxyamide)-2'-deoxyuridine
<220> FEATURE:
<221> NAME/KEY: misc_feature
<222> LOCATION: (48)..(48)
<223> OTHER INFORMATION: 5-(N-benzylcarboxyamide)-2'-deoxyuridine

<400> SEQUENCE: 10
ccgtctgcct gcagcgggac acangaggac nngggggnnna gccgnngngg    50

<210> SEQ ID NO 11
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (31)..(33)
<223> OTHER INFORMATION: 5-(N-benzylcarboxyamide)-2'-deoxyuridine
<220> FEATURE:
<221> NAME/KEY: misc_feature
<222> LOCATION: (38)..(40)
<223> OTHER INFORMATION: 5-(N-benzylcarboxyamide)-2'-deoxyuridine
<220> FEATURE:
<221> NAME/KEY: misc_feature
<222> LOCATION: (46)..(47)
<223> OTHER INFORMATION: 5-(N-benzylcarboxyamide)-2'-deoxyuridine
<220> FEATURE:
<221> NAME/KEY: misc_feature
<222> LOCATION: (49)..(49)
<223> OTHER INFORMATION: 5-(N-benzylcarboxyamide)-2'-deoxyuridine

<400> SEQUENCE: 11
cgtctgcctg cagcgggaca canngaggac nnngggggnnn agccgnngng gc    52

<210> SEQ ID NO 12
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)

```
<223> OTHER INFORMATION: 5-(N-benzylcarboxyamide)-2'-deoxyuridine
<220> FEATURE:
<221> NAME/KEY: misc_feature
<222> LOCATION: (29)..(30)
<223> OTHER INFORMATION: 5-(N-benzylcarboxyamide)-2'-deoxyuridine
<220> FEATURE:
<221> NAME/KEY: misc_feature
<222> LOCATION: (35)..(37)
<223> OTHER INFORMATION: 5-(N-benzylcarboxyamide)-2'-deoxyuridine
<220> FEATURE:
<221> NAME/KEY: misc_feature
<222> LOCATION: (43)..(44)
<223> OTHER INFORMATION: 5-(N-benzylcarboxyamide)-2'-deoxyuridine
<220> FEATURE:
<221> NAME/KEY: misc_feature
<222> LOCATION: (46)..(46)
<223> OTHER INFORMATION: 5-(N-benzylcarboxyamide)-2'-deoxyuridine

<400> SEQUENCE: 12
gtctgcctgc agcgggacac angaggacnn ggggnnnagc cgnngnggca            50

<210> SEQ ID NO 13
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: 5-(N-benzylcarboxyamide)-2'-deoxyuridine
<220> FEATURE:
<221> NAME/KEY: misc_feature
<222> LOCATION: (28)..(29)
<223> OTHER INFORMATION: 5-(N-benzylcarboxyamide)-2'-deoxyuridine
<220> FEATURE:
<221> NAME/KEY: misc_feature
<222> LOCATION: (34)..(36)
<223> OTHER INFORMATION: 5-(N-benzylcarboxyamide)-2'-deoxyuridine
<220> FEATURE:
<221> NAME/KEY: misc_feature
<222> LOCATION: (42)..(43)
<223> OTHER INFORMATION: 5-(N-benzylcarboxyamide)-2'-deoxyuridine
<220> FEATURE:
<221> NAME/KEY: misc_feature
<222> LOCATION: (45)..(45)
<223> OTHER INFORMATION: 5-(N-benzylcarboxyamide)-2'-deoxyuridine

<400> SEQUENCE: 13
tctgcctgca gcgggacaca ngaggacnng gggnnnagcc gnngnggcac            50

<210> SEQ ID NO 14
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: 5-(N-benzylcarboxyamide)-2'-deoxyuridine
<220> FEATURE:
<221> NAME/KEY: misc_feature
<222> LOCATION: (27)..(28)
<223> OTHER INFORMATION: 5-(N-benzylcarboxyamide)-2'-deoxyuridine
<220> FEATURE:
<221> NAME/KEY: misc_feature
<222> LOCATION: (33)..(35)
<223> OTHER INFORMATION: 5-(N-benzylcarboxyamide)-2'-deoxyuridine
<220> FEATURE:
<221> NAME/KEY: misc_feature
<222> LOCATION: (41)..(42)
<223> OTHER INFORMATION: 5-(N-benzylcarboxyamide)-2'-deoxyuridine
<220> FEATURE:
<221> NAME/KEY: misc_feature
<222> LOCATION: (44)..(44)
```

-continued

<223> OTHER INFORMATION: 5-(N-benzylcarboxyamide)-2'-deoxyuridine

<400> SEQUENCE: 14
ctgcctgcag cgggacacan gaggacnngg ggnnnagccg nngnggcaca            50

<210> SEQ ID NO 15
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: 5-(N-benzylcarboxyamide)-2'-deoxyuridine
<220> FEATURE:
<221> NAME/KEY: misc_feature
<222> LOCATION: (26)..(27)
<223> OTHER INFORMATION: 5-(N-benzylcarboxyamide)-2'-deoxyuridine
<220> FEATURE:
<221> NAME/KEY: misc_feature
<222> LOCATION: (32)..(34)
<223> OTHER INFORMATION: 5-(N-benzylcarboxyamide)-2'-deoxyuridine
<220> FEATURE:
<221> NAME/KEY: misc_feature
<222> LOCATION: (40)..(41)
<223> OTHER INFORMATION: 5-(N-benzylcarboxyamide)-2'-deoxyuridine
<220> FEATURE:
<221> NAME/KEY: misc_feature
<222> LOCATION: (43)..(43)
<223> OTHER INFORMATION: 5-(N-benzylcarboxyamide)-2'-deoxyuridine

<400> SEQUENCE: 15
tgcctgcagc gggacacang aggacnnggg gnnnagccgn ngnggcacag            50

<210> SEQ ID NO 16
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: 5-(N-benzylcarboxyamide)-2'-deoxyuridine
<220> FEATURE:
<221> NAME/KEY: misc_feature
<222> LOCATION: (25)..(26)
<223> OTHER INFORMATION: 5-(N-benzylcarboxyamide)-2'-deoxyuridine
<220> FEATURE:
<221> NAME/KEY: misc_feature
<222> LOCATION: (31)..(33)
<223> OTHER INFORMATION: 5-(N-benzylcarboxyamide)-2'-deoxyuridine
<220> FEATURE:
<221> NAME/KEY: misc_feature
<222> LOCATION: (39)..(40)
<223> OTHER INFORMATION: 5-(N-benzylcarboxyamide)-2'-deoxyuridine
<220> FEATURE:
<221> NAME/KEY: misc_feature
<222> LOCATION: (42)..(42)
<223> OTHER INFORMATION: 5-(N-benzylcarboxyamide)-2'-deoxyuridine

<400> SEQUENCE: 16
gcctgcagcg ggacacanga ggacnngggg nnnagccgnn gnggcacaga            50

<210> SEQ ID NO 17
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)

```
<223> OTHER INFORMATION: 5-(N-benzylcarboxyamide)-2'-deoxyuridine
<220> FEATURE:
<221> NAME/KEY: misc_feature
<222> LOCATION: (24)..(25)
<223> OTHER INFORMATION: 5-(N-benzylcarboxyamide)-2'-deoxyuridine
<220> FEATURE:
<221> NAME/KEY: misc_feature
<222> LOCATION: (30)..(32)
<223> OTHER INFORMATION: 5-(N-benzylcarboxyamide)-2'-deoxyuridine
<220> FEATURE:
<221> NAME/KEY: misc_feature
<222> LOCATION: (38)..(39)
<223> OTHER INFORMATION: 5-(N-benzylcarboxyamide)-2'-deoxyuridine
<220> FEATURE:
<221> NAME/KEY: misc_feature
<222> LOCATION: (41)..(41)
<223> OTHER INFORMATION: 5-(N-benzylcarboxyamide)-2'-deoxyuridine

<400> SEQUENCE: 17
cctgcagcgg gacacangag gacnnggggn nnagccgnng nggcacagag                50

<210> SEQ ID NO 18
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (29)..(31)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 18
ctgcagcggg acacangagg acnnggggnn nagccgnngn ggcacagaga                50

<210> SEQ ID NO 19
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
```

<223> OTHER INFORMATION: 5-(N-benzylcarboxyamide)-2'-deoxyuridine

<400> SEQUENCE: 19
tgcagcggga cacangagga cnngggggnnn agccgnngng gcacagagaa         50

<210> SEQ ID NO 20
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 20
gcagcgggac acangaggac nnggggnnna gccgnngngg cacagagaag         50

<210> SEQ ID NO 21
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: 5-(N-benzylcarboxyamide)-2'-deoxyuridine
<220> FEATURE:
<221> NAME/KEY: misc_feature
<222> LOCATION: (20)..(21)
<223> OTHER INFORMATION: 5-(N-benzylcarboxyamide)-2'-deoxyuridine
<220> FEATURE:
<221> NAME/KEY: misc_feature
<222> LOCATION: (26)..(28)
<223> OTHER INFORMATION: 5-(N-benzylcarboxyamide)-2'-deoxyuridine
<220> FEATURE:
<221> NAME/KEY: misc_feature
<222> LOCATION: (34)..(35)
<223> OTHER INFORMATION: 5-(N-benzylcarboxyamide)-2'-deoxyuridine
<220> FEATURE:
<221> NAME/KEY: misc_feature
<222> LOCATION: (37)..(37)
<223> OTHER INFORMATION: 5-(N-benzylcarboxyamide)-2'-deoxyuridine

<400> SEQUENCE: 21
cagcgggaca cangaggacn ngggggnnnag ccgnngnggc acagagaaga         50

<210> SEQ ID NO 22
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)

```
<223> OTHER INFORMATION: 5-(N-benzylcarboxyamide)-2'-deoxyuridine
<220> FEATURE:
<221> NAME/KEY: misc_feature
<222> LOCATION: (19)..(20)
<223> OTHER INFORMATION: 5-(N-benzylcarboxyamide)-2'-deoxyuridine
<220> FEATURE:
<221> NAME/KEY: misc_feature
<222> LOCATION: (25)..(27)
<223> OTHER INFORMATION: 5-(N-benzylcarboxyamide)-2'-deoxyuridine
<220> FEATURE:
<221> NAME/KEY: misc_feature
<222> LOCATION: (33)..(34)
<223> OTHER INFORMATION: 5-(N-benzylcarboxyamide)-2'-deoxyuridine
<220> FEATURE:
<221> NAME/KEY: misc_feature
<222> LOCATION: (36)..(36)
<223> OTHER INFORMATION: 5-(N-benzylcarboxyamide)-2'-deoxyuridine

<400> SEQUENCE: 22
agcgggacac angaggacnn ggggnnnagc cgnngnggca cagagaagaa         50

<210> SEQ ID NO 23
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (18)..(19)
<223> OTHER INFORMATION: 5-(N-benzylcarboxyamide)-2'-deoxyuridine
<220> FEATURE:
<221> NAME/KEY: misc_feature
<222> LOCATION: (24)..(26)
<223> OTHER INFORMATION: 5-(N-benzylcarboxyamide)-2'-deoxyuridine
<220> FEATURE:
<221> NAME/KEY: misc_feature
<222> LOCATION: (32)..(33)
<223> OTHER INFORMATION: 5-(N-benzylcarboxyamide)-2'-deoxyuridine
<220> FEATURE:
<221> NAME/KEY: misc_feature
<222> LOCATION: (35)..(35)
<223> OTHER INFORMATION: 5-(N-benzylcarboxyamide)-2'-deoxyuridine

<400> SEQUENCE: 23
gcgggacaca ngaggacnng gggnnnagcc gnngnggcac agagaagaaa         50

<210> SEQ ID NO 24
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: 5-(N-benzylcarboxyamide)-2'-deoxyuridine
<220> FEATURE:
<221> NAME/KEY: misc_feature
<222> LOCATION: (17)..(18)
<223> OTHER INFORMATION: 5-(N-benzylcarboxyamide)-2'-deoxyuridine
<220> FEATURE:
<221> NAME/KEY: misc_feature
<222> LOCATION: (23)..(25)
<223> OTHER INFORMATION: 5-(N-benzylcarboxyamide)-2'-deoxyuridine
<220> FEATURE:
<221> NAME/KEY: misc_feature
<222> LOCATION: (31)..(32)
<223> OTHER INFORMATION: 5-(N-benzylcarboxyamide)-2'-deoxyuridine
<220> FEATURE:
<221> NAME/KEY: misc_feature
<222> LOCATION: (34)..(34)
```

<223> OTHER INFORMATION: 5-(N-benzylcarboxyamide)-2'-deoxyuridine

<400> SEQUENCE: 24
cgggacacan gaggacnngg ggnnnagccg nngnggcaca gagaagaaac            50

<210> SEQ ID NO 25
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: 5-(N-benzylcarboxyamide)-2'-deoxyuridine
<220> FEATURE:
<221> NAME/KEY: misc_feature
<222> LOCATION: (16)..(17)
<223> OTHER INFORMATION: 5-(N-benzylcarboxyamide)-2'-deoxyuridine
<220> FEATURE:
<221> NAME/KEY: misc_feature
<222> LOCATION: (22)..(24)
<223> OTHER INFORMATION: 5-(N-benzylcarboxyamide)-2'-deoxyuridine
<220> FEATURE:
<221> NAME/KEY: misc_feature
<222> LOCATION: (30)..(31)
<223> OTHER INFORMATION: 5-(N-benzylcarboxyamide)-2'-deoxyuridine
<220> FEATURE:
<221> NAME/KEY: misc_feature
<222> LOCATION: (33)..(33)
<223> OTHER INFORMATION: 5-(N-benzylcarboxyamide)-2'-deoxyuridine

<400> SEQUENCE: 25
gggacacang aggacnnggg gnnnagccgn ngnggcacag agaagaaaca            50

<210> SEQ ID NO 26
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 5-(N-benzylcarboxyamide)-2'-deoxyuridine
<220> FEATURE:
<221> NAME/KEY: misc_feature
<222> LOCATION: (15)..(16)
<223> OTHER INFORMATION: 5-(N-benzylcarboxyamide)-2'-deoxyuridine
<220> FEATURE:
<221> NAME/KEY: misc_feature
<222> LOCATION: (21)..(26)
<223> OTHER INFORMATION: 5-(N-benzylcarboxyamide)-2'-deoxyuridine
<220> FEATURE:
<221> NAME/KEY: misc_feature
<222> LOCATION: (29)..(30)
<223> OTHER INFORMATION: 5-(N-benzylcarboxyamide)-2'-deoxyuridine
<220> FEATURE:
<221> NAME/KEY: misc_feature
<222> LOCATION: (32)..(32)
<223> OTHER INFORMATION: 5-(N-benzylcarboxyamide)-2'-deoxyuridine

<400> SEQUENCE: 26
ggacacanga ggacnngggg nnnagccgnn gnggcacaga agaaacaa            50

<210> SEQ ID NO 27
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)

<223> OTHER INFORMATION: 5-(N-benzylcarboxyamide)-2'-deoxyuridine
<220> FEATURE:
<221> NAME/KEY: misc_feature
<222> LOCATION: (14)..(15)
<223> OTHER INFORMATION: 5-(N-benzylcarboxyamide)-2'-deoxyuridine
<220> FEATURE:
<221> NAME/KEY: misc_feature
<222> LOCATION: (20)..(22)
<223> OTHER INFORMATION: 5-(N-benzylcarboxyamide)-2'-deoxyuridine
<220> FEATURE:
<221> NAME/KEY: misc_feature
<222> LOCATION: (28)..(29)
<223> OTHER INFORMATION: 5-(N-benzylcarboxyamide)-2'-deoxyuridine
<220> FEATURE:
<221> NAME/KEY: misc_feature
<222> LOCATION: (31)..(31)
<223> OTHER INFORMATION: 5-(N-benzylcarboxyamide)-2'-deoxyuridine

<400> SEQUENCE: 27
gacacangag gacnnggggn nnagccgnng nggcacagag aagaaacaag         50

<210> SEQ ID NO 28
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (13)..(14)
<223> OTHER INFORMATION: 5-(N-benzylcarboxyamide)-2'-deoxyuridine
<220> FEATURE:
<221> NAME/KEY: misc_feature
<222> LOCATION: (19)..(21)
<223> OTHER INFORMATION: 5-(N-benzylcarboxyamide)-2'-deoxyuridine
<220> FEATURE:
<221> NAME/KEY: misc_feature
<222> LOCATION: (27)..(28)
<223> OTHER INFORMATION: 5-(N-benzylcarboxyamide)-2'-deoxyuridine
<220> FEATURE:
<221> NAME/KEY: misc_feature
<222> LOCATION: (30)..(30)
<223> OTHER INFORMATION: 5-(N-benzylcarboxyamide)-2'-deoxyuridine

<400> SEQUENCE: 28
acacangagg acnnggggnn nagccgnngn ggcacagaga agaaacaaga         50

<210> SEQ ID NO 29
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 5-(N-benzylcarboxyamide)-2'-deoxyuridine
<220> FEATURE:
<221> NAME/KEY: misc_feature
<222> LOCATION: (12)..(13)
<223> OTHER INFORMATION: 5-(N-benzylcarboxyamide)-2'-deoxyuridine
<220> FEATURE:
<221> NAME/KEY: misc_feature
<222> LOCATION: (18)..(20)
<223> OTHER INFORMATION: 5-(N-benzylcarboxyamide)-2'-deoxyuridine
<220> FEATURE:
<221> NAME/KEY: misc_feature
<222> LOCATION: (26)..(27)
<223> OTHER INFORMATION: 5-(N-benzylcarboxyamide)-2'-deoxyuridine
<220> FEATURE:
<221> NAME/KEY: misc_feature
<222> LOCATION: (29)..(29)

<223> OTHER INFORMATION: 5-(N-benzylcarboxyamide)-2'-deoxyuridine

<400> SEQUENCE: 29
cacangagga cnngggggnnn agccgnngng gcacagagaa gaaacaagac         50

<210> SEQ ID NO 30
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 5-(N-benzylcarboxyamide)-2'-deoxyuridine
<220> FEATURE:
<221> NAME/KEY: misc_feature
<222> LOCATION: (11)..(12)
<223> OTHER INFORMATION: 5-(N-benzylcarboxyamide)-2'-deoxyuridine
<220> FEATURE:
<221> NAME/KEY: misc_feature
<222> LOCATION: (17)..(19)
<223> OTHER INFORMATION: 5-(N-benzylcarboxyamide)-2'-deoxyuridine
<220> FEATURE:
<221> NAME/KEY: misc_feature
<222> LOCATION: (25)..(26)
<223> OTHER INFORMATION: 5-(N-benzylcarboxyamide)-2'-deoxyuridine
<220> FEATURE:
<221> NAME/KEY: misc_feature
<222> LOCATION: (28)..(28)
<223> OTHER INFORMATION: 5-(N-benzylcarboxyamide)-2'-deoxyuridine

<400> SEQUENCE: 30
acangaggac nngggggnnna gccgnngngg cacagagaag aaacaagacc         50

<210> SEQ ID NO 31
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 31
tgcagcggga cacangagga cnnggggnnn agccgnngng         40

<210> SEQ ID NO 32
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)

```
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 32
gcagcgggac acangaggac nngggggnnna gccgnngng                                   39

<210> SEQ ID NO 33
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: 5-(N-benzylcarboxyamide)-2'-deoxyuridine
<220> FEATURE:
<221> NAME/KEY: misc_feature
<222> LOCATION: (20)..(21)
<223> OTHER INFORMATION: 5-(N-benzylcarboxyamide)-2'-deoxyuridine
<220> FEATURE:
<221> NAME/KEY: misc_feature
<222> LOCATION: (26)..(28)
<223> OTHER INFORMATION: 5-(N-benzylcarboxyamide)-2'-deoxyuridine
<220> FEATURE:
<221> NAME/KEY: misc_feature
<222> LOCATION: (34)..(35)
<223> OTHER INFORMATION: 5-(N-benzylcarboxyamide)-2'-deoxyuridine
<220> FEATURE:
<221> NAME/KEY: misc_feature
<222> LOCATION: (37)..(37)
<223> OTHER INFORMATION: 5-(N-benzylcarboxyamide)-2'-deoxyuridine

<400> SEQUENCE: 33
cagcgggaca cangaggacn ngggggnnnag ccgnngng                                    38

<210> SEQ ID NO 34
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (19)..(20)
<223> OTHER INFORMATION: 5-(N-benzylcarboxyamide)-2'-deoxyuridine
<220> FEATURE:
<221> NAME/KEY: misc_feature
<222> LOCATION: (25)..(27)
<223> OTHER INFORMATION: 5-(N-benzylcarboxyamide)-2'-deoxyuridine
<220> FEATURE:
<221> NAME/KEY: misc_feature
<222> LOCATION: (33)..(34)
<223> OTHER INFORMATION: 5-(N-benzylcarboxyamide)-2'-deoxyuridine
<220> FEATURE:
<221> NAME/KEY: misc_feature
<222> LOCATION: (36)..(36)
```

```
<223> OTHER INFORMATION: 5-(N-benzylcarboxyamide)-2'-deoxyuridine

<400> SEQUENCE: 34
agcgggacac angaggacnn ggggnnnagc cgnngng                              37

<210> SEQ ID NO 35
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (18)..(19)
<223> OTHER INFORMATION: 5-(N-benzylcarboxyamide)-2'-deoxyuridine
<220> FEATURE:
<221> NAME/KEY: misc_feature
<222> LOCATION: (24)..(26)
<223> OTHER INFORMATION: 5-(N-benzylcarboxyamide)-2'-deoxyuridine
<220> FEATURE:
<221> NAME/KEY: misc_feature
<222> LOCATION: (32)..(33)
<223> OTHER INFORMATION: 5-(N-benzylcarboxyamide)-2'-deoxyuridine
<220> FEATURE:
<221> NAME/KEY: misc_feature
<222> LOCATION: (35)..(35)
<223> OTHER INFORMATION: 5-(N-benzylcarboxyamide)-2'-deoxyuridine

<400> SEQUENCE: 35
gcgggacaca ngaggacnng gggnnnagcc gnngng                               36

<210> SEQ ID NO 36
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: 5-(N-benzylcarboxyamide)-2'-deoxyuridine
<220> FEATURE:
<221> NAME/KEY: misc_feature
<222> LOCATION: (17)..(18)
<223> OTHER INFORMATION: 5-(N-benzylcarboxyamide)-2'-deoxyuridine
<220> FEATURE:
<221> NAME/KEY: misc_feature
<222> LOCATION: (23)..(25)
<223> OTHER INFORMATION: 5-(N-benzylcarboxyamide)-2'-deoxyuridine
<220> FEATURE:
<221> NAME/KEY: misc_feature
<222> LOCATION: (31)..(32)
<223> OTHER INFORMATION: 5-(N-benzylcarboxyamide)-2'-deoxyuridine
<220> FEATURE:
<221> NAME/KEY: misc_feature
<222> LOCATION: (34)..(34)
<223> OTHER INFORMATION: 5-(N-benzylcarboxyamide)-2'-deoxyuridine

<400> SEQUENCE: 36
cgggacacan gaggacnngg ggnnnagccg nngng                                35

<210> SEQ ID NO 37
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
```

-continued

<223> OTHER INFORMATION: 5-(N-benzylcarboxyamide)-2'-deoxyuridine
<220> FEATURE:
<221> NAME/KEY: misc_feature
<222> LOCATION: (16)..(17)
<223> OTHER INFORMATION: 5-(N-benzylcarboxyamide)-2'-deoxyuridine
<220> FEATURE:
<221> NAME/KEY: misc_feature
<222> LOCATION: (22)..(24)
<223> OTHER INFORMATION: 5-(N-benzylcarboxyamide)-2'-deoxyuridine
<220> FEATURE:
<221> NAME/KEY: misc_feature
<222> LOCATION: (30)..(31)
<223> OTHER INFORMATION: 5-(N-benzylcarboxyamide)-2'-deoxyuridine
<220> FEATURE:
<221> NAME/KEY: misc_feature
<222> LOCATION: (33)..(33)
<223> OTHER INFORMATION: 5-(N-benzylcarboxyamide)-2'-deoxyuridine

<400> SEQUENCE: 37
gggacacang aggacnnggg gnnnagccgn ngng         34

<210> SEQ ID NO 38
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 5-(N-benzylcarboxyamide)-2'-deoxyuridine
<220> FEATURE:
<221> NAME/KEY: misc_feature
<222> LOCATION: (15)..(16)
<223> OTHER INFORMATION: 5-(N-benzylcarboxyamide)-2'-deoxyuridine
<220> FEATURE:
<221> NAME/KEY: misc_feature
<222> LOCATION: (21)..(23)
<223> OTHER INFORMATION: 5-(N-benzylcarboxyamide)-2'-deoxyuridine
<220> FEATURE:
<221> NAME/KEY: misc_feature
<222> LOCATION: (29)..(30)
<223> OTHER INFORMATION: 5-(N-benzylcarboxyamide)-2'-deoxyuridine
<220> FEATURE:
<221> NAME/KEY: misc_feature
<222> LOCATION: (32)..(32)
<223> OTHER INFORMATION: 5-(N-benzylcarboxyamide)-2'-deoxyuridine

<400> SEQUENCE: 38
ggacacanga ggacnngggg nnnagccgnn gng         33

<210> SEQ ID NO 39
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (14)..(15)
<223> OTHER INFORMATION: 5-(N-benzylcarboxyamide)-2'-deoxyuridine
<220> FEATURE:
<221> NAME/KEY: misc_feature
<222> LOCATION: (20)..(22)
<223> OTHER INFORMATION: 5-(N-benzylcarboxyamide)-2'-deoxyuridine
<220> FEATURE:
<221> NAME/KEY: misc_feature
<222> LOCATION: (28)..(29)
<223> OTHER INFORMATION: 5-(N-benzylcarboxyamide)-2'-deoxyuridine
<220> FEATURE:
<221> NAME/KEY: misc_feature
<222> LOCATION: (31)..(31)

-continued

<223> OTHER INFORMATION: 5-(N-benzylcarboxyamide)-2'-deoxyuridine

<400> SEQUENCE: 39
gacacangag gacnnggggn nnagccgnng ng                                    32

<210> SEQ ID NO 40
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (13)..(14)
<223> OTHER INFORMATION: 5-(N-benzylcarboxyamide)-2'-deoxyuridine
<220> FEATURE:
<221> NAME/KEY: misc_feature
<222> LOCATION: (19)..(21)
<223> OTHER INFORMATION: 5-(N-benzylcarboxyamide)-2'-deoxyuridine
<220> FEATURE:
<221> NAME/KEY: misc_feature
<222> LOCATION: (27)..(28)
<223> OTHER INFORMATION: 5-(N-benzylcarboxyamide)-2'-deoxyuridine
<220> FEATURE:
<221> NAME/KEY: misc_feature
<222> LOCATION: (30)..(30)
<223> OTHER INFORMATION: 5-(N-benzylcarboxyamide)-2'-deoxyuridine

<400> SEQUENCE: 40
acacangagg acnnggggnn nagccgnngn g                                     31

<210> SEQ ID NO 41
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 5-(N-benzylcarboxyamide)-2'-deoxyuridine
<220> FEATURE:
<221> NAME/KEY: misc_feature
<222> LOCATION: (12)..(13)
<223> OTHER INFORMATION: 5-(N-benzylcarboxyamide)-2'-deoxyuridine
<220> FEATURE:
<221> NAME/KEY: misc_feature
<222> LOCATION: (18)..(20)
<223> OTHER INFORMATION: 5-(N-benzylcarboxyamide)-2'-deoxyuridine
<220> FEATURE:
<221> NAME/KEY: misc_feature
<222> LOCATION: (26)..(27)
<223> OTHER INFORMATION: 5-(N-benzylcarboxyamide)-2'-deoxyuridine
<220> FEATURE:
<221> NAME/KEY: misc_feature
<222> LOCATION: (29)..(29)
<223> OTHER INFORMATION: 5-(N-benzylcarboxyamide)-2'-deoxyuridine

<400> SEQUENCE: 41
cacangagga cnngggggnnn agccgnngng                                      30

<210> SEQ ID NO 42
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)

```
<223> OTHER INFORMATION: 5-(N-benzylcarboxyamide)-2'-deoxyuridine
<220> FEATURE:
<221> NAME/KEY: misc_feature
<222> LOCATION: (11)..(12)
<223> OTHER INFORMATION: 5-(N-benzylcarboxyamide)-2'-deoxyuridine
<220> FEATURE:
<221> NAME/KEY: misc_feature
<222> LOCATION: (17)..(19)
<223> OTHER INFORMATION: 5-(N-benzylcarboxyamide)-2'-deoxyuridine
<220> FEATURE:
<221> NAME/KEY: misc_feature
<222> LOCATION: (25)..(26)
<223> OTHER INFORMATION: 5-(N-benzylcarboxyamide)-2'-deoxyuridine
<220> FEATURE:
<221> NAME/KEY: misc_feature
<222> LOCATION: (28)..(28)
<223> OTHER INFORMATION: 5-(N-benzylcarboxyamide)-2'-deoxyuridine

<400> SEQUENCE: 42
acangaggac nngggnnna gccgnngng                                          29

<210> SEQ ID NO 43
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (9)..(10)
<223> OTHER INFORMATION: 5-(N-benzylcarboxyamide)-2'-deoxyuridine
<220> FEATURE:
<221> NAME/KEY: misc_feature
<222> LOCATION: (15)..(17)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (26)..(26)
<223> OTHER INFORMATION: 5-(N-benzylcarboxyamide)-2'-deoxyuridine

<400> SEQUENCE: 43
angaggacnn gggnnnagc cgnngng                                            27

<210> SEQ ID NO 44
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-(N-benzylcarboxyamide)-2'-deoxyuridine
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (14)..(16)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (25)..(25)
```

<223> OTHER INFORMATION: 5-(N-benzylcarboxyamide)-2'-deoxyuridine

<400> SEQUENCE: 44
ngaggacnng gggnnnagcc gnngng          26

<210> SEQ ID NO 45
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: a C, G, or Independently selected from a
      modified nucleotide, specifically a modified pyrimidine
<220> FEATURE:
<221> NAME/KEY: misc_feature
<222> LOCATION: (3)..(3)
<223> OTHER INFORMATION: Independently selected from a modified
      nucleotide, specifically a modified pyrimidine
<220> FEATURE:
<221> NAME/KEY: misc_feature
<222> LOCATION: (5)..(5)
<223> OTHER INFORMATION: an A or G
<220> FEATURE:
<221> NAME/KEY: misc_feature
<222> LOCATION: (8)..(8)
<223> OTHER INFORMATION: an A or G
<220> FEATURE:
<221> NAME/KEY: misc_feature
<222> LOCATION: (9)..(9)
<223> OTHER INFORMATION: a C or G
<220> FEATURE:
<221> NAME/KEY: misc_feature
<222> LOCATION: (10)..(10)
<223> OTHER INFORMATION: Independently selected from a modified
      nucleotide, specifically a modified pyrimidine
<220> FEATURE:
<221> NAME/KEY: misc_feature
<222> LOCATION: (11)..(11)
<223> OTHER INFORMATION: Independently selected from a modified
      nucleotide, specifically a modified pyrimidine, or T
<220> FEATURE:
<221> NAME/KEY: misc_feature
<222> LOCATION: (16)..(17)
<223> OTHER INFORMATION: Independently selected from a modified
      nucleotide, specifically a modified pyrimidine
<220> FEATURE:
<221> NAME/KEY: misc_feature
<222> LOCATION: (18)..(18)
<223> OTHER INFORMATION: Independently selected from a modified
      nucleotide, specifically a modified pyrimidine, or T
<220> FEATURE:
<221> NAME/KEY: misc_feature
<222> LOCATION: (20)..(20)
<223> OTHER INFORMATION: an A, G, or Independently selected from a
      modified nucleotide, specifically a modified pyrimidine
<220> FEATURE:
<221> NAME/KEY: misc_feature
<222> LOCATION: (24)..(25)
<223> OTHER INFORMATION: Independently selected from a modified
      nucleotide, specifically a modified pyrimidine
<220> FEATURE:
<221> NAME/KEY: misc_feature
<222> LOCATION: (26)..(26)
<223> OTHER INFORMATION: an A or G
<220> FEATURE:
<221> NAME/KEY: misc_feature
<222> LOCATION: (27)..(27)
<223> OTHER INFORMATION: Independently selected from a modified
      nucleotide, specifically a modified pyrimidine

<400> SEQUENCE: 45
nangnggnnn ngggggnnnan ccgnnnng          28

```
<210> SEQ ID NO 46
<211> LENGTH: 85
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(68)
<223> OTHER INFORMATION: n is a, c, g, or t

<400> SEQUENCE: 46 tttttttgg tcttgtttct tctctgtgnn nnnnnnnnn nnnnnnnnnn nnnnnnnnnn      60
nnnnnnnnca ggcagacggt cactc                                         85

<210> SEQ ID NO 47
<211> LENGTH: 25
<212> TYPE: DNA
<213> ORGANISM: Artificial Sequence
<220> FEATURE:
<223> OTHER INFORMATION: Synthetic

<400> SEQUENCE: 47
atatatatga gtgaccgtct gcctg                                         25

<210> SEQ ID NO 48
<211> LENGTH: 28
<212> TYPE: DNA
<213> ORGANISM: Artificial Sequence
<220> FEATURE:
<223> OTHER INFORMATION: Synthetic

<400> SEQUENCE: 48 tttttttgg tcttgtttct tctctgtg                                       28

<210> SEQ ID NO 49
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: 5-(N-benzylcarboxamide)-2'-deoxyuridine
<220> FEATURE:
<221> NAME/KEY: misc_feature
<222> LOCATION: (20)..(21)
<223> OTHER INFORMATION: 5-(N-benzylcarboxamide)-2'-deoxyuridine
<220> FEATURE:
<221> NAME/KEY: misc_feature
<222> LOCATION: (26)..(28)
<223> OTHER INFORMATION: 5-(N-benzylcarboxamide)-2'-deoxyuridine
<220> FEATURE:
<221> NAME/KEY: misc_feature
<222> LOCATION: (34)..(35)
<223> OTHER INFORMATION: 5-(N-benzylcarboxamide)-2'-deoxyuridine
<220> FEATURE:
<221> NAME/KEY: misc_feature
<222> LOCATION: (37)..(37)
<223> OTHER INFORMATION: 5-(N-benzylcarboxamide)-2'-deoxyuridine

<400> SEQUENCE: 49
cagcgggaca cangaggacn ngggnnngg ccgnngngg                           39

<210> SEQ ID NO 50
<211> LENGTH: 39
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (13)..(13)
<223> OTHER INFORMATION: 5-(N-benzylcarboxyamide)-2'-deoxyuridine
<220> FEATURE:
<221> NAME/KEY: misc_feature
<222> LOCATION: (20)..(21)
<223> OTHER INFORMATION: 5-(N-benzylcarboxyamide)-2'-deoxyuridine
<220> FEATURE:
<221> NAME/KEY: misc_feature
<222> LOCATION: (26)..(28)
<223> OTHER INFORMATION: 5-(N-benzylcarboxyamide)-2'-deoxyuridine
<220> FEATURE:
<221> NAME/KEY: misc_feature
<222> LOCATION: (34)..(35)
<223> OTHER INFORMATION: 5-(N-benzylcarboxyamide)-2'-deoxyuridine
<220> FEATURE:
<221> NAME/KEY: misc_feature
<222> LOCATION: (37)..(37)
<223> OTHER INFORMATION: 5-(N-benzylcarboxyamide)-2'-deoxyuridine

<400> SEQUENCE: 50
cagcgggaca cangaggacn ngggnnnag ccgnngngc                             39

<210> SEQ ID NO 51
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (22)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 51
gcagcgggac acangaggac angggnnna gccgnngngg                            40

<210> SEQ ID NO 52
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (22)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
```

```
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 52
gcagcgggac acangaggac cngggggnnna gccgnngngg                               40

<210> SEQ ID NO 53
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 53
gcggcgggac acangaggac nngggggnnna gccgnngngg                               40

<210> SEQ ID NO 54
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(15)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 54
gcagcgggac acannaggac nngggggnnna gccgnngngg                               40

<210> SEQ ID NO 55
<211> LENGTH: 40
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 55
gcagcggaac acangaggac nngggnnna gccgnngngg                              40

<210> SEQ ID NO 56
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 56
gcagcggnac acangaggac nngggnnna gccgnngngg                              40

<210> SEQ ID NO 57
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: 5-(N-benzylcarboxyamide)-2'-deoxyuridine
<220> FEATURE:
<221> NAME/KEY: misc_feature
<222> LOCATION: (20)..(21)
<223> OTHER INFORMATION: 5-(N-benzylcarboxyamide)-2'-deoxyuridine
<220> FEATURE:
<221> NAME/KEY: misc_feature
<222> LOCATION: (25)..(27)
<223> OTHER INFORMATION: 5-(N-benzylcarboxyamide)-2'-deoxyuridine
```

```
<220> FEATURE:
<221> NAME/KEY: misc_feature
<222> LOCATION: (33)..(34)
<223> OTHER INFORMATION: 5-(N-benzylcarboxyamide)-2'-deoxyuridine
<220> FEATURE:
<221> NAME/KEY: misc_feature
<222> LOCATION: (36)..(36)
<223> OTHER INFORMATION: 5-(N-benzylcarboxyamide)-2'-deoxyuridine

<400> SEQUENCE: 57
cagcgggaca cangaggacn ngggnnnagc cgnngnggca                              40

<210> SEQ ID NO 58
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 58
ncagcgggac acangaggac nngggnnna gccgnngngg                               40

<210> SEQ ID NO 59
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 59
gcagcgggac acangaggac nngggggnnna gccgnngngg                             40
```

```
<210> SEQ ID NO 60
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (32)..(32)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 60
gcagcgggac acangaggac nngggannna gncgnngngg                40

<210> SEQ ID NO 61
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 61
gcagcgggac acangaggac nngggannna gccanngngg                40

<210> SEQ ID NO 62
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
```

```
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (34)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 62
gcagcgggac acangaggac nngggnnna gccnnngngg                40

<210> SEQ ID NO 63
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 63
gcagcgngac anangaggac nngggggnnna gccgnngngg                40

<210> SEQ ID NO 64
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
```

-continued

```
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 64
gcagcgggac acangaggac nngggnnna gccgnngnag                              40

<210> SEQ ID NO 65
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 65
gnagcgggac acangaggac nngggnnna accgnngngg                              40

<210> SEQ ID NO 66
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine
```

-continued

<400> SEQUENCE: 66
gnagcgggac acangggac nngggggnnna accgnngngg                40

<210> SEQ ID NO 67
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 67
gaagcgggac acangaggac nngggggnnna accgnngngg                40

<210> SEQ ID NO 68
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 68
gcagcgggac acangaggac nngaggnnna accgnngngg                40

<210> SEQ ID NO 69
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine -continued

```
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 69
gcagcgggac acangaggac nngggngnnna accgnngngg                              40

<210> SEQ ID NO 70
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (18)..(18)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(28)
<223> OTHER INFORMATION: 5-(N-benzylcarboxyamide)-2'-deoxyuridine
<220> FEATURE:
<221> NAME/KEY: misc_feature
<222> LOCATION: (34)..(35)
<223> OTHER INFORMATION: 5-(N-benzylcarboxyamide)-2'-deoxyuridine
<220> FEATURE:
<221> NAME/KEY: misc_feature
<222> LOCATION: (37)..(37)
<223> OTHER INFORMATION: 5-(N-benzylcarboxyamide)-2'-deoxyuridine

<400> SEQUENCE: 70
gcagcgggac acangagnac nngggngnnaa ccgnngnggc                              40

<210> SEQ ID NO 71
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(28)
<223> OTHER INFORMATION: 5-(N-benzylcarboxyamide)-2'-deoxyuridine
<220> FEATURE:
<221> NAME/KEY: misc_feature
<222> LOCATION: (34)..(35)
<223> OTHER INFORMATION: 5-(N-benzylcarboxyamide)-2'-deoxyuridine
```

```
<220> FEATURE:
<221> NAME/KEY: misc_feature
<222> LOCATION: (37)..(37)
<223> OTHER INFORMATION: 5-(N-benzylcarboxyamide)-2'-deoxyuridine

<400> SEQUENCE: 71
gcagcgggac acangaggac nngggggnnaa ccgnngnggc                            40

<210> SEQ ID NO 72
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 72
gcagcgggac acangaggac nngggggnnna accgnngngn                            40

<210> SEQ ID NO 73
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(39)
<223> OTHER INFORMATION: 5-(N-benzylcarboxyamide)-2'-deoxyuridine

<400> SEQUENCE: 73
gaagcgggac acangaggac nngggggnnna gccgnngnng                            40

<210> SEQ ID NO 74
<211> LENGTH: 40
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 74
gaagcgggac acangaggac nngggggnnna gccgnngngg                    40

<210> SEQ ID NO 75
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (17)..(17)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 75
gcaacgggac acangangac nngggggnnna gccgnngngg                    40

<210> SEQ ID NO 76
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (17)..(17)
<223> OTHER INFORMATION: 5-(N-benzylcarboxyamide)-2'-deoxyuridine
```

```
<220> FEATURE:
<221> NAME/KEY: misc_feature
<222> LOCATION: (21)..(23)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 76
gcagcgggac acangangac nnngggnnna gccgnnangg                              40

<210> SEQ ID NO 77
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (17)..(17)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 77
gnagcgggac acangangac nngggnnna gccgnngngg                               40

<210> SEQ ID NO 78
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
```

```
<220> FEATURE:
<221> NAME/KEY: misc_feature
<222> LOCATION: (28)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine

<400> SEQUENCE: 78
gnagcgggac acangaggac nnggggnna gccgnngcgg                              40

<210> SEQ ID NO 79
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 79
gnagcgggac acangaggac nngggnnna gccgnngngg                              40

<210> SEQ ID NO 80
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 80
gcagcggggc acangaggac nngggnnna gccgnngngg                              40
```

```
<210> SEQ ID NO 81
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 81
gcagcgggac acangaggac nngggqnnna gcagnnangg                          40

<210> SEQ ID NO 82
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 82
gcagngggac acangaggac nngggqnnna gccgnnangc                          40

<210> SEQ ID NO 83
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
```

<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 83
gcagcgggac acangaggac nngggggnnna gccgnnangc        40

<210> SEQ ID NO 84
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 84
gcagcgggac acangaggac nngggggnnna gccgnngngc        40

<210> SEQ ID NO 85
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

```
<400> SEQUENCE: 85
gcagcgggac acangaggac nngggggnnna gccgnngnga                    40

<210> SEQ ID NO 86
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (18)..(18)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 86
gcagccggac acangagnac nngggggnnna gccgnngngg                    40

<210> SEQ ID NO 87
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (33)..(33)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 87
gcagcnggac acacgaggac nngggggnnna gcngnngngg                    40

<210> SEQ ID NO 88
<211> LENGTH: 40
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 88
gcagcaggac acangaggac nngggnnna gccgnngngg                                40

<210> SEQ ID NO 89
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 89
gcagnaggac acangaggac nngggnnna gccgnngngg                                40

<210> SEQ ID NO 90
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
```

```
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 90
gcagagggac acangaggac nngggqnnna gccgnngngg                              40

<210> SEQ ID NO 91
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 91
gcagngggac acangaggac nngggqnnna gccgnngngg                              40

<210> SEQ ID NO 92
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 5-(N-benzylcarboxyamide)-2'-deoxyuridine
<220> FEATURE:
<221> NAME/KEY: misc_feature
<222> LOCATION: (10)..(10)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
```

```
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 92
gcagngggan acangaggac gnnggggnnn agccgnngng                           40

<210> SEQ ID NO 93
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 93
gnagcgggac acangaggac gnnggggnnn agccgnngng                           40

<210> SEQ ID NO 94
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 94
ggagcggggc acangaggac nnggggnnn agccgnngng                            40
```

```
<210> SEQ ID NO 95
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 95
gcagcgggac acangaggac nnggggnnn agccgnngng                40

<210> SEQ ID NO 96
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: 5-(N-benzylcarboxyamide)-2'-deoxyuridine
<220> FEATURE:
<221> NAME/KEY: misc_feature
<222> LOCATION: (15)..(15)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 96
gcagcgggac acnangagga cnnggggnnn aggccgnngn                40

<210> SEQ ID NO 97
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
```

```
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine

<400> SEQUENCE: 97
gcagcgggac acangaggac nnggggnnna accgnn                              36

<210> SEQ ID NO 98
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine

<400> SEQUENCE: 98
gcagcgggac acangaggac nnggggnnna g                                   31

<210> SEQ ID NO 99
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine

<400> SEQUENCE: 99
gcagcgggac acangaggac nngggggnnn agc                                 33

<210> SEQ ID NO 100
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
```

```
<220> FEATURE:
<221> NAME/KEY: misc_feature
<222> LOCATION: (17)..(17)
<223> OTHER INFORMATION: 5-(N-benzylcarboxyamide)-2'-deoxyuridine
<220> FEATURE:
<221> NAME/KEY: misc_feature
<222> LOCATION: (19)..(19)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (29)..(31)
<223> OTHER INFORMATION: 5-(N-benzylcarboxyamide)-2'-deoxyuridine

<400> SEQUENCE: 100
gcagcnggac acangangna cgnnggggnn nagcc                              35

<210> SEQ ID NO 101
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (17)..(17)
<223> OTHER INFORMATION: 5-(N-benzylcarboxyamide)-2'-deoxyuridine
<220> FEATURE:
<221> NAME/KEY: misc_feature
<222> LOCATION: (19)..(19)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (29)..(31)
<223> OTHER INFORMATION: 5-(N-benzylcarboxyamide)-2'-deoxyuridine

<400> SEQUENCE: 101
gcagcnggac acangangna cgnnggggnn nagcc                              35

<210> SEQ ID NO 102
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (15)..(15)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
```

```
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 102
ggaacnagcg nggangggc nngggnnna gccgnnangc                          40

<210> SEQ ID NO 103
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 5-(N-benzylcarboxyamide)-2'-deoxyuridine
<220> FEATURE:
<221> NAME/KEY: misc_feature
<222> LOCATION: (10)..(10)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 103
gaacnagcgn ggangggc nngggnnna gccgnnangc                           40

<210> SEQ ID NO 104
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
```

```
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 104
ggaacnagcg ngangggggc nngggnnna gccgnnangc                        40

<210> SEQ ID NO 105
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-(N-benzylcarboxyamide)-2'-deoxyuridine
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (16)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 105
nggaacnagc gnggangggg gcnnggggnnn agccgnnang                      40

<210> SEQ ID NO 106
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (15)..(15)
<223> OTHER INFORMATION: 5-(N-benzylcarboxyamide)-2'-deoxyuridine
```

```
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 106
ggaacnagcg nggangggggg cnngggggnnn agccannang                    40

<210> SEQ ID NO 107
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (15)..(15)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 107
ggaacnagcg nggangggggg cnngggggnnn agccgnnang                    40

<210> SEQ ID NO 108
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (15)..(15)
<223> OTHER INFORMATION: 5-(N-benzylcarboxyamide)-2'-deoxyuridine
```

```
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 108
ggaacnagcg nggangggggg cnnggagnnn agccgnnang         40

<210> SEQ ID NO 109
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (15)..(15)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 109
ggaacnagcg nggangggg cnngggggnnn aaccgnnang         40

<210> SEQ ID NO 110
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (15)..(15)
<223> OTHER INFORMATION: 5-(N-benzylcarboxyamide)-2'-deoxyuridine
```

```
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 110
gaaacnagcg nggangggggg cnngggggnnn agccgnnang                 40

<210> SEQ ID NO 111
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (15)..(15)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 111
ggaacnagcg nggangggggg cnngggggnnn agccgnngng                 40

<210> SEQ ID NO 112
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (15)..(15)
<223> OTHER INFORMATION: 5-(N-benzylcarboxyamide)-2'-deoxyuridine
```

```
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 112
ggagcnagcg nggangggga cnnggggnnn agccgnngng                40

<210> SEQ ID NO 113
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (15)..(15)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 113
ggaacnagca cggangggggg cnngggggnnn agccgnnang                40

<210> SEQ ID NO 114
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (15)..(15)
<223> OTHER INFORMATION: 5-(N-benzylcarboxyamide)-2'-deoxyuridine
```

-continued

```
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (32)..(32)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 114
ggaacnagcg nggangggggg cnngggggnnn anccgnnana                40

<210> SEQ ID NO 115
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (15)..(15)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (27)..(28)
<223> OTHER INFORMATION: 5-(N-benzylcarboxyamide)-2'-deoxyuridine
<220> FEATURE:
<221> NAME/KEY: misc_feature
<222> LOCATION: (31)..(31)
<223> OTHER INFORMATION: 5-(N-benzylcarboxyamide)-2'-deoxyuridine

<400> SEQUENCE: 115
ggaacnagcg nggangggggg cnngggnnag n                         31

<210> SEQ ID NO 116
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
```

```
<220> FEATURE:
<221> NAME/KEY: misc_feature
<222> LOCATION: (16)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (29)..(31)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 116
gcagaangcg gnanangagg acnnggagnn nagccgnngn                            40

<210> SEQ ID NO 117
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (16)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (29)..(31)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 117
gcagaangcg gnanangagg acnnggggnn nagccgnngn                            40

<210> SEQ ID NO 118
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
```

```
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (16)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (29)..(31)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 118
gcagaangcg gnananggggg acnnggggnn nggccgnngn                   40

<210> SEQ ID NO 119
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (16)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (29)..(31)
<223> OTHER INFORMATION: 5-(N-benzylcarboxyamide)-2'-deoxyuridine
<220> FEATURE:
<221> NAME/KEY: misc_feature
<222> LOCATION: (33)..(33)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 119
gcagaangcg gnananggggg gcnnggggnn nanccgnngn                   40
```

<210> SEQ ID NO 120
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (16)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (29)..(31)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 120
gcagaangcg gnananggggg gcnnggggnn nagccanngn                                40

<210> SEQ ID NO 121
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (16)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (29)..(31)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine

```
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 121
gcagaangag gnanangagg acnnggggnn nagccgnngn                              40

<210> SEQ ID NO 122
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (16)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (29)..(31)
<223> OTHER INFORMATION: 5-(N-benzylcarboxyamide)-2'-deoxyuridine
<220> FEATURE:
<221> NAME/KEY: misc_feature
<222> LOCATION: (33)..(33)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 122
gcagaangcg gnanangggg gcnnggggnn nanccgnnan                              40

<210> SEQ ID NO 123
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (16)..(16)
<223> OTHER INFORMATION: 5-(N-benzylcarboxyamide)-2'-deoxyuridine
```

```
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (29)..(31)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 123
gcagaangcg gnananggggg gcnnggggnn nagccgnnan                    40

<210> SEQ ID NO 124
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (16)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(25)
<223> OTHER INFORMATION: 5-(N-benzylcarboxyamide)-2'-deoxyuridine
<220> FEATURE:
<221> NAME/KEY: misc_feature
<222> LOCATION: (29)..(31)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 124
gcagaangcg gnanangggg gcnnngggnn nagccgnnan                     40

<210> SEQ ID NO 125
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
```

```
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (16)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (30)..(32)
<223> OTHER INFORMATION: 5-(N-benzylcarboxyamide)-2'-deoxyuridine
<220> FEATURE:
<221> NAME/KEY: misc_feature
<222> LOCATION: (38)..(39)
<223> OTHER INFORMATION: 5-(N-benzylcarboxyamide)-2'-deoxyuridine

<400> SEQUENCE: 125
gcagaangcg gnananggggg acnnggggggn nnagccgnng                              40

<210> SEQ ID NO 126
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (17)..(17)
<223> OTHER INFORMATION: 5-(N-benzylcarboxyamide)-2'-deoxyuridine
<220> FEATURE:
<221> NAME/KEY: misc_feature
<222> LOCATION: (24)..(25)
<223> OTHER INFORMATION: 5-(N-benzylcarboxyamide)-2'-deoxyuridine
<220> FEATURE:
<221> NAME/KEY: misc_feature
<222> LOCATION: (30)..(32)
<223> OTHER INFORMATION: 5-(N-benzylcarboxyamide)-2'-deoxyuridine
<220> FEATURE:
<221> NAME/KEY: misc_feature
<222> LOCATION: (38)..(39)
<223> OTHER INFORMATION: 5-(N-benzylcarboxyamide)-2'-deoxyuridine

<400> SEQUENCE: 126
gcagaangcg gnanagnggg ggcnnggggn nnagccgnna                               40

<210> SEQ ID NO 127
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-(N-benzylcarboxyamide)-2'-deoxyuridine
<220> FEATURE:
<221> NAME/KEY: misc_feature
<222> LOCATION: (8)..(8)
<223> OTHER INFORMATION: 5-(N-benzylcarboxyamide)-2'-deoxyuridine
```

```
<220> FEATURE:
<221> NAME/KEY: misc_feature
<222> LOCATION: (13)..(13)
<223> OTHER INFORMATION: 5-(N-benzylcarboxyamide)-2'-deoxyuridine
<220> FEATURE:
<221> NAME/KEY: misc_feature
<222> LOCATION: (15)..(15)
<223> OTHER INFORMATION: 5-(N-benzylcarboxyamide)-2'-deoxyuridine
<220> FEATURE:
<221> NAME/KEY: misc_feature
<222> LOCATION: (17)..(17)
<223> OTHER INFORMATION: 5-(N-benzylcarboxyamide)-2'-deoxyuridine
<220> FEATURE:
<221> NAME/KEY: misc_feature
<222> LOCATION: (24)..(25)
<223> OTHER INFORMATION: 5-(N-benzylcarboxyamide)-2'-deoxyuridine
<220> FEATURE:
<221> NAME/KEY: misc_feature
<222> LOCATION: (30)..(32)
<223> OTHER INFORMATION: 5-(N-benzylcarboxyamide)-2'-deoxyuridine
<220> FEATURE:
<221> NAME/KEY: misc_feature
<222> LOCATION: (34)..(34)
<223> OTHER INFORMATION: 5-(N-benzylcarboxyamide)-2'-deoxyuridine

<400> SEQUENCE: 127
ngcagaangc ggnananggg ggcnnggggn nnanccg                                 37

<210> SEQ ID NO 128
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (4)..(4)
<223> OTHER INFORMATION: 5-(N-benzylcarboxyamide)-2'-deoxyuridine
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (18)..(19)
<223> OTHER INFORMATION: 5-(N-benzylcarboxyamide)-2'-deoxyuridine
<220> FEATURE:
<221> NAME/KEY: misc_feature
<222> LOCATION: (24)..(25)
<223> OTHER INFORMATION: 5-(N-benzylcarboxyamide)-2'-deoxyuridine
<220> FEATURE:
<221> NAME/KEY: misc_feature
<222> LOCATION: (28)..(28)
<223> OTHER INFORMATION: 5-(N-benzylcarboxyamide)-2'-deoxyuridine
<220> FEATURE:
<221> NAME/KEY: misc_feature
<222> LOCATION: (32)..(33)
<223> OTHER INFORMATION: 5-(N-benzylcarboxyamide)-2'-deoxyuridine
<220> FEATURE:
<221> NAME/KEY: misc_feature
<222> LOCATION: (35)..(35)
<223> OTHER INFORMATION: 5-(N-benzylcarboxyamide)-2'-deoxyuridine

<400> SEQUENCE: 128
gngncacnng ngggagnng gggnngancc gnngnccgcc                               40

<210> SEQ ID NO 129
<211> LENGTH: 40
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (4)..(4)
<223> OTHER INFORMATION: 5-(N-benzylcarboxyamide)-2'-deoxyuridine
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (18)..(19)
<223> OTHER INFORMATION: 5-(N-benzylcarboxyamide)-2'-deoxyuridine
<220> FEATURE:
<221> NAME/KEY: misc_feature
<222> LOCATION: (24)..(25)
<223> OTHER INFORMATION: 5-(N-benzylcarboxyamide)-2'-deoxyuridine
<220> FEATURE:
<221> NAME/KEY: misc_feature
<222> LOCATION: (28)..(28)
<223> OTHER INFORMATION: 5-(N-benzylcarboxyamide)-2'-deoxyuridine
<220> FEATURE:
<221> NAME/KEY: misc_feature
<222> LOCATION: (32)..(33)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine

<400> SEQUENCE: 129
gngncacnng ngggagnng gggnngancc gnngnncgcc                    40

<210> SEQ ID NO 130
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (4)..(4)
<223> OTHER INFORMATION: 5-(N-benzylcarboxyamide)-2'-deoxyuridine
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (18)..(19)
<223> OTHER INFORMATION: 5-(N-benzylcarboxyamide)-2'-deoxyuridine
<220> FEATURE:
<221> NAME/KEY: misc_feature
<222> LOCATION: (24)..(25)
<223> OTHER INFORMATION: 5-(N-benzylcarboxyamide)-2'-deoxyuridine
<220> FEATURE:
<221> NAME/KEY: misc_feature
<222> LOCATION: (28)..(28)
<223> OTHER INFORMATION: 5-(N-benzylcarboxyamide)-2'-deoxyuridine
```

```
<220> FEATURE:
<221> NAME/KEY: misc_feature
<222> LOCATION: (32)..(33)
<223> OTHER INFORMATION: 5-(N-benzylcarboxyamide)-2'-deoxyuridine
<220> FEATURE:
<221> NAME/KEY: misc_feature
<222> LOCATION: (35)..(37)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 130
gngncacnng ngggggagnng gggnngancc gnngnnncgn                    40

<210> SEQ ID NO 131
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (4)..(4)
<223> OTHER INFORMATION: 5-(N-benzylcarboxyamide)-2'-deoxyuridine
<220> FEATURE:
<221> NAME/KEY: misc_feature
<222> LOCATION: (8)..(8)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (18)..(19)
<223> OTHER INFORMATION: 5-(N-benzylcarboxyamide)-2'-deoxyuridine
<220> FEATURE:
<221> NAME/KEY: misc_feature
<222> LOCATION: (24)..(25)
<223> OTHER INFORMATION: 5-(N-benzylcarboxyamide)-2'-deoxyuridine
<220> FEATURE:
<221> NAME/KEY: misc_feature
<222> LOCATION: (28)..(28)
<223> OTHER INFORMATION: 5-(N-benzylcarboxyamide)-2'-deoxyuridine
<220> FEATURE:
<221> NAME/KEY: misc_feature
<222> LOCATION: (32)..(33)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 131
gngncacncg nggggagnng gggnngancc gnngnncgcn                     40

<210> SEQ ID NO 132
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
```

```
<220> FEATURE:
<221> NAME/KEY: misc_feature
<222> LOCATION: (4)..(4)
<223> OTHER INFORMATION: 5-(N-benzylcarboxyamide)-2'-deoxyuridine
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (18)..(19)
<223> OTHER INFORMATION: 5-(N-benzylcarboxyamide)-2'-deoxyuridine
<220> FEATURE:
<221> NAME/KEY: misc_feature
<222> LOCATION: (24)..(25)
<223> OTHER INFORMATION: 5-(N-benzylcarboxyamide)-2'-deoxyuridine
<220> FEATURE:
<221> NAME/KEY: misc_feature
<222> LOCATION: (28)..(28)
<223> OTHER INFORMATION: 5-(N-benzylcarboxyamide)-2'-deoxyuridine
<220> FEATURE:
<221> NAME/KEY: misc_feature
<222> LOCATION: (33)..(33)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 132
gngncacnng ngggggagnng gggnngancc aangnncgcn                             40

<210> SEQ ID NO 133
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (4)..(4)
<223> OTHER INFORMATION: 5-(N-benzylcarboxyamide)-2'-deoxyuridine
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (18)..(19)
<223> OTHER INFORMATION: 5-(N-benzylcarboxyamide)-2'-deoxyuridine
<220> FEATURE:
<221> NAME/KEY: misc_feature
<222> LOCATION: (24)..(25)
<223> OTHER INFORMATION: 5-(N-benzylcarboxyamide)-2'-deoxyuridine
<220> FEATURE:
<221> NAME/KEY: misc_feature
<222> LOCATION: (28)..(28)
<223> OTHER INFORMATION: 5-(N-benzylcarboxyamide)-2'-deoxyuridine
<220> FEATURE:
<221> NAME/KEY: misc_feature
<222> LOCATION: (32)..(33)
<223> OTHER INFORMATION: 5-(N-benzylcarboxyamide)-2'-deoxyuridine
```

```
<220> FEATURE:
<221> NAME/KEY: misc_feature
<222> LOCATION: (35)..(37)
<223> OTHER INFORMATION: 5-(N-benzylcarboxyamide)-2'-deoxyuridine

<400> SEQUENCE: 133
gngncacnng ngggggagnng gggnngancc gnngnnncgc                                40

<210> SEQ ID NO 134
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (4)..(4)
<223> OTHER INFORMATION: 5-(N-benzylcarboxyamide)-2'-deoxyuridine
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (18)..(20)
<223> OTHER INFORMATION: 5-(N-benzylcarboxyamide)-2'-deoxyuridine
<220> FEATURE:
<221> NAME/KEY: misc_feature
<222> LOCATION: (24)..(25)
<223> OTHER INFORMATION: 5-(N-benzylcarboxyamide)-2'-deoxyuridine
<220> FEATURE:
<221> NAME/KEY: misc_feature
<222> LOCATION: (27)..(27)
<223> OTHER INFORMATION: 5-(N-benzylcarboxyamide)-2'-deoxyuridine
<220> FEATURE:
<221> NAME/KEY: misc_feature
<222> LOCATION: (29)..(29)
<223> OTHER INFORMATION: 5-(N-benzylcarboxyamide)-2'-deoxyuridine
<220> FEATURE:
<221> NAME/KEY: misc_feature
<222> LOCATION: (33)..(34)
<223> OTHER INFORMATION: 5-(N-benzylcarboxyamide)-2'-deoxyuridine
<220> FEATURE:
<221> NAME/KEY: misc_feature
<222> LOCATION: (37)..(39)
<223> OTHER INFORMATION: 5-(N-benzylcarboxyamide)-2'-deoxyuridine

<400> SEQUENCE: 134
gngncacnng nggggagnnn gggnngnanc cgnncgnnnc                                 40

<210> SEQ ID NO 135
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: 5-(N-benzylcarboxyamide)-2'-deoxyuridine
<220> FEATURE:
<221> NAME/KEY: misc_feature
<222> LOCATION: (20)..(20)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
```

```
<220> FEATURE:
<221> NAME/KEY: misc_feature
<222> LOCATION: (29)..(31)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 135
ggcgacgcgc acagnggggn agnnggggnn naaccgnngn                                40

<210> SEQ ID NO 136
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (19)..(19)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(30)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 136
ggcgacgcgc gcanagggna gnnggggnnn aaccgnngnc                                40

<210> SEQ ID NO 137
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: 5-(N-benzylcarboxyamide)-2'-deoxyuridine
<220> FEATURE:
<221> NAME/KEY: misc_feature
<222> LOCATION: (18)..(18)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
```

```
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 137
gcgacgcgcg cangggnag nnggggnnna acggnngncg                           40

<210> SEQ ID NO 138
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: 5-(N-benzylcarboxyamide)-2'-deoxyuridine
<220> FEATURE:
<221> NAME/KEY: misc_feature
<222> LOCATION: (16)..(17)
<223> OTHER INFORMATION: 5-(N-benzylcarboxyamide)-2'-deoxyuridine
<220> FEATURE:
<221> NAME/KEY: misc_feature
<222> LOCATION: (22)..(24)
<223> OTHER INFORMATION: 5-(N-benzylcarboxyamide)-2'-deoxyuridine
<220> FEATURE:
<221> NAME/KEY: misc_feature
<222> LOCATION: (30)..(31)
<223> OTHER INFORMATION: 5-(N-benzylcarboxyamide)-2'-deoxyuridine
<220> FEATURE:
<221> NAME/KEY: misc_feature
<222> LOCATION: (33)..(33)
<223> OTHER INFORMATION: 5-(N-benzylcarboxyamide)-2'-deoxyuridine

<400> SEQUENCE: 138
gaccaacang aggacnnggg gnnnagccgn ngnggcacag                          40

<210> SEQ ID NO 139
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: 5-(N-benzylcarboxyamide)-2'-deoxyuridine
<220> FEATURE:
<221> NAME/KEY: misc_feature
<222> LOCATION: (16)..(17)
<223> OTHER INFORMATION: 5-(N-benzylcarboxyamide)-2'-deoxyuridine
<220> FEATURE:
<221> NAME/KEY: misc_feature
<222> LOCATION: (22)..(24)
<223> OTHER INFORMATION: 5-(N-benzylcarboxyamide)-2'-deoxyuridine
<220> FEATURE:
<221> NAME/KEY: misc_feature
<222> LOCATION: (30)..(31)
<223> OTHER INFORMATION: 5-(N-benzylcarboxyamide)-2'-deoxyuridine
<220> FEATURE:
<221> NAME/KEY: misc_feature
<222> LOCATION: (33)..(34)
<223> OTHER INFORMATION: 5-(N-benzylcarboxyamide)-2'-deoxyuridine

<400> SEQUENCE: 139
gaccaacang aggacnnggg gnnnagccgn ngnngcacag                          40

<210> SEQ ID NO 140
<211> LENGTH: 40
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (10)..(10)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (19)..(20)
<223> OTHER INFORMATION: 5-(N-benzylcarboxyamide)-2'-deoxyuridine
<220> FEATURE:
<221> NAME/KEY: misc_feature
<222> LOCATION: (25)..(27)
<223> OTHER INFORMATION: 5-(N-benzylcarboxyamide)-2'-deoxyuridine
<220> FEATURE:
<221> NAME/KEY: misc_feature
<222> LOCATION: (33)..(34)
<223> OTHER INFORMATION: 5-(N-benzylcarboxyamide)-2'-deoxyuridine
<220> FEATURE:
<221> NAME/KEY: misc_feature
<222> LOCATION: (36)..(36)
<223> OTHER INFORMATION: 5-(N-benzylcarboxyamide)-2'-deoxyuridine

<400> SEQUENCE: 140
gggaagcgan angaggacnn ggggnnnagc cgnngnggca                              40

<210> SEQ ID NO 141
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (19)..(20)
<223> OTHER INFORMATION: 5-(N-benzylcarboxyamide)-2'-deoxyuridine
<220> FEATURE:
<221> NAME/KEY: misc_feature
<222> LOCATION: (25)..(27)
<223> OTHER INFORMATION: 5-(N-benzylcarboxyamide)-2'-deoxyuridine
<220> FEATURE:
<221> NAME/KEY: misc_feature
<222> LOCATION: (29)..(29)
<223> OTHER INFORMATION: 5-(N-benzylcarboxyamide)-2'-deoxyuridine
<220> FEATURE:
<221> NAME/KEY: misc_feature
<222> LOCATION: (33)..(34)
<223> OTHER INFORMATION: 5-(N-benzylcarboxyamide)-2'-deoxyuridine
<220> FEATURE:
<221> NAME/KEY: misc_feature
<222> LOCATION: (36)..(36)
<223> OTHER INFORMATION: 5-(N-benzylcarboxyamide)-2'-deoxyuridine

<400> SEQUENCE: 141
gggaagcgan angaggagnn ggggnnnanc cgnngncaac                              40

<210> SEQ ID NO 142
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 5-(N-benzylcarboxyamide)-2'-deoxyuridine
```

```
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (31)..(31)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 142
ggagnaggga aaanggggag nngggnnna nccgnngnca                              40

<210> SEQ ID NO 143
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: 5-(N-benzylcarboxyamide)-2'-deoxyuridine
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(21)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (31)..(31)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 143
ganngcngga ggangggag ngggggnnna nccgnngnca                              40

<210> SEQ ID NO 144
<211> LENGTH: 40
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (3)..(4)
<223> OTHER INFORMATION: 5-(N-benzylcarboxyamide)-2'-deoxyuridine
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (31)..(31)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 144
ganngcngga ggangggggag nngggggnnna nccgnngnca                           40

<210> SEQ ID NO 145
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: 5-(N-benzylcarboxyamide)-2'-deoxyuridine
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 145
ganngcngga ggangaggac nngggggnnna gccgnngngg                            40

<210> SEQ ID NO 146
<211> LENGTH: 40
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (22)..(22)
<223> OTHER INFORMATION: 5-(N-benzylcarboxyamide)-2'-deoxyuridine
<220> FEATURE:
<221> NAME/KEY: misc_feature
<222> LOCATION: (27)..(29)
<223> OTHER INFORMATION: 5-(N-benzylcarboxyamide)-2'-deoxyuridine
<220> FEATURE:
<221> NAME/KEY: misc_feature
<222> LOCATION: (35)..(36)
<223> OTHER INFORMATION: 5-(N-benzylcarboxyamide)-2'-deoxyuridine
<220> FEATURE:
<221> NAME/KEY: misc_feature
<222> LOCATION: (38)..(38)
<223> OTHER INFORMATION: 5-(N-benzylcarboxyamide)-2'-deoxyuridine

<400> SEQUENCE: 146
gccggggccg cnangaggac angggnnna gccgnngngg                    40

<210> SEQ ID NO 147
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(12)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (16)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (29)..(31)
<223> OTHER INFORMATION: 5-(N-benzylcarboxyamide)-2'-deoxyuridine
<220> FEATURE:
<221> NAME/KEY: misc_feature
<222> LOCATION: (37)..(38)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 147
gcagaangcg ananangggg gcnnggggnn nagccgnnan                    40

<210> SEQ ID NO 148
<211> LENGTH: 40
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (28)..(29)
<223> OTHER INFORMATION: 5-(N-benzylcarboxyamide)-2'-deoxyuridine
<220> FEATURE:
<221> NAME/KEY: misc_feature
<222> LOCATION: (36)..(37)
<223> OTHER INFORMATION: 5-(N-benzylcarboxyamide)-2'-deoxyuridine
<220> FEATURE:
<221> NAME/KEY: misc_feature
<222> LOCATION: (39)..(39)
<223> OTHER INFORMATION: 5-(N-benzylcarboxyamide)-2'-deoxyuridine

<400> SEQUENCE: 148
ggnggcacac nggnggggggg cnnggggnng agccgnnang                          40

<210> SEQ ID NO 149
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: 5-(N-benzylcarboxyamide)-2'-deoxyuridine
<220> FEATURE:
<221> NAME/KEY: misc_feature
<222> LOCATION: (13)..(15)
<223> OTHER INFORMATION: 5-(N-benzylcarboxyamide)-2'-deoxyuridine
<220> FEATURE:
<221> NAME/KEY: misc_feature
<222> LOCATION: (21)..(22)
<223> OTHER INFORMATION: 5-(N-benzylcarboxyamide)-2'-deoxyuridine
<220> FEATURE:
<221> NAME/KEY: misc_feature
<222> LOCATION: (24)..(24)
<223> OTHER INFORMATION: 5-(N-benzylcarboxyamide)-2'-deoxyuridine

<400> SEQUENCE: 149
gaggacnngg ggnnnagccg nngng                                           25

<210> SEQ ID NO 150
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: 5-(N-benzylcarboxyamide)-2'-deoxyuridine
<220> FEATURE:
<221> NAME/KEY: misc_feature
<222> LOCATION: (12)..(14)
<223> OTHER INFORMATION: 5-(N-benzylcarboxyamide)-2'-deoxyuridine
```

```
<220> FEATURE:
<221> NAME/KEY: misc_feature
<222> LOCATION: (20)..(21)
<223> OTHER INFORMATION: 5-(N-benzylcarboxyamide)-2'-deoxyuridine
<220> FEATURE:
<221> NAME/KEY: misc_feature
<222> LOCATION: (23)..(23)
<223> OTHER INFORMATION: 5-(N-benzylcarboxyamide)-2'-deoxyuridine

<400> SEQUENCE: 150
aggacnnggg gnnnagccgn ngng                                              24

<210> SEQ ID NO 151
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: 5-(N-benzylcarboxyamide)-2'-deoxyuridine
<220> FEATURE:
<221> NAME/KEY: misc_feature
<222> LOCATION: (11)..(13)
<223> OTHER INFORMATION: 5-(N-benzylcarboxyamide)-2'-deoxyuridine
<220> FEATURE:
<221> NAME/KEY: misc_feature
<222> LOCATION: (19)..(20)
<223> OTHER INFORMATION: 5-(N-benzylcarboxyamide)-2'-deoxyuridine
<220> FEATURE:
<221> NAME/KEY: misc_feature
<222> LOCATION: (22)..(22)
<223> OTHER INFORMATION: 5-(N-benzylcarboxyamide)-2'-deoxyuridine

<400> SEQUENCE: 151
ggacnngggg nnnagccgnn gng                                               23

<210> SEQ ID NO 152
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 5-(N-benzylcarboxyamide)-2'-deoxyuridine
<220> FEATURE:
<221> NAME/KEY: misc_feature
<222> LOCATION: (10)..(12)
<223> OTHER INFORMATION: 5-(N-benzylcarboxyamide)-2'-deoxyuridine
<220> FEATURE:
<221> NAME/KEY: misc_feature
<222> LOCATION: (18)..(19)
<223> OTHER INFORMATION: 5-(N-benzylcarboxyamide)-2'-deoxyuridine
<220> FEATURE:
<221> NAME/KEY: misc_feature
<222> LOCATION: (21)..(21)
<223> OTHER INFORMATION: 5-(N-benzylcarboxyamide)-2'-deoxyuridine

<400> SEQUENCE: 152
gacnnggggn nnagccgnng ng                                                22

<210> SEQ ID NO 153
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: 5-(N-benzylcarboxyamide)-2'-deoxyuridine
```

```
<220> FEATURE:
<221> NAME/KEY: misc_feature
<222> LOCATION: (9)..(11)
<223> OTHER INFORMATION: 5-(N-benzylcarboxyamide)-2'-deoxyuridine
<220> FEATURE:
<221> NAME/KEY: misc_feature
<222> LOCATION: (17)..(18)
<223> OTHER INFORMATION: 5-(N-benzylcarboxyamide)-2'-deoxyuridine
<220> FEATURE:
<221> NAME/KEY: misc_feature
<222> LOCATION: (20)..(20)
<223> OTHER INFORMATION: 5-(N-benzylcarboxyamide)-2'-deoxyuridine

<400> SEQUENCE: 153 acnngggggnn nagccgnngn g                                              21

<210> SEQ ID NO 154
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: a C, G, or Independently selected from a
      modified nucleotide, specifically a modified pyrimidine
<220> FEATURE:
<221> NAME/KEY: misc_feature
<222> LOCATION: (3)..(3)
<223> OTHER INFORMATION: Independently selected from a modified
      nucleotide, specifically a modified pyrimidine
<220> FEATURE:
<221> NAME/KEY: misc_feature
<222> LOCATION: (5)..(5)
<223> OTHER INFORMATION: an A or G
<220> FEATURE:
<221> NAME/KEY: misc_feature
<222> LOCATION: (8)..(8)
<223> OTHER INFORMATION: an A or G
<220> FEATURE:
<221> NAME/KEY: misc_feature
<222> LOCATION: (9)..(9)
<223> OTHER INFORMATION: a C or G
<220> FEATURE:
<221> NAME/KEY: misc_feature
<222> LOCATION: (10)..(10)
<223> OTHER INFORMATION: any base or no base
<220> FEATURE:
<221> NAME/KEY: misc_feature
<222> LOCATION: (11)..(11)
<223> OTHER INFORMATION: Independently selected from a modified
      nucleotide, specifically a modified pyrimidine
<220> FEATURE:
<221> NAME/KEY: misc_feature
<222> LOCATION: (12)..(12)
<223> OTHER INFORMATION: Independently selected from a modified
      nucleotide, specifically a modified pyrimidine, or T
<220> FEATURE:
<221> NAME/KEY: misc_feature
<222> LOCATION: (17)..(17)
<223> OTHER INFORMATION: any base or no base
<220> FEATURE:
<221> NAME/KEY: misc_feature
<222> LOCATION: (18)..(19)
<223> OTHER INFORMATION: Independently selected from a modified
      nucleotide, specifically a modified pyrimidine
<220> FEATURE:
<221> NAME/KEY: misc_feature
<222> LOCATION: (20)..(20)
<223> OTHER INFORMATION: Independently selected from a modified
      nucleotide, specifically a modified pyrimidine, or T
<220> FEATURE:
<221> NAME/KEY: misc_feature
<222> LOCATION: (22)..(22)
<223> OTHER INFORMATION: an A, G, or Independently selected from a
      modified nucleotide, specifically a modified pyrimidine
<220> FEATURE:
```

```
<221> NAME/KEY: misc_feature
<222> LOCATION: (26)..(27)
<223> OTHER INFORMATION: Independently selected from a modified
      nucleotide, specifically a modified pyrimidine
<220> FEATURE:
<221> NAME/KEY: misc_feature
<222> LOCATION: (28)..(28)
<223> OTHER INFORMATION: an A or G
<220> FEATURE:
<221> NAME/KEY: misc_feature
<222> LOCATION: (29)..(29)
<223> OTHER INFORMATION: Independently selected from a modified
      nucleotide, specifically a modified pyrimidine

<400> SEQUENCE: 154
nangnggnnn nngggggnnnn anccgnnnng                                      30

<210> SEQ ID NO 155
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: a C, G, or Independently selected from a
      modified nucleotide, specifically a modified pyrimidine
<220> FEATURE:
<221> NAME/KEY: misc_feature
<222> LOCATION: (3)..(3)
<223> OTHER INFORMATION: Independently selected from a modified
      nucleotide, specifically a modified pyrimidine
<220> FEATURE:
<221> NAME/KEY: misc_feature
<222> LOCATION: (5)..(5)
<223> OTHER INFORMATION: an A or G
<220> FEATURE:
<221> NAME/KEY: misc_feature
<222> LOCATION: (8)..(8)
<223> OTHER INFORMATION: an A or G
<220> FEATURE:
<221> NAME/KEY: misc_feature
<222> LOCATION: (9)..(9)
<223> OTHER INFORMATION: a C or G
<220> FEATURE:
<221> NAME/KEY: misc_feature
<222> LOCATION: (10)..(10)
<223> OTHER INFORMATION: any base or no base
<220> FEATURE:
<221> NAME/KEY: misc_feature
<222> LOCATION: (11)..(12)
<223> OTHER INFORMATION: Independently selected from a modified
      nucleotide, specifically a modified pyrimidine
<220> FEATURE:
<221> NAME/KEY: misc_feature
<222> LOCATION: (17)..(17)
<223> OTHER INFORMATION: any base or no base
<220> FEATURE:
<221> NAME/KEY: misc_feature
<222> LOCATION: (18)..(20)
<223> OTHER INFORMATION: Independently selected from a modified
      nucleotide, specifically a modified pyrimidine
<220> FEATURE:
<221> NAME/KEY: misc_feature
<222> LOCATION: (22)..(22)
<223> OTHER INFORMATION: an A, G, or Independently selected from a
      modified nucleotide, specifically a modified pyrimidine
<220> FEATURE:
<221> NAME/KEY: misc_feature
<222> LOCATION: (26)..(27)
<223> OTHER INFORMATION: Independently selected from a modified
      nucleotide, specifically a modified pyrimidine
<220> FEATURE:
<221> NAME/KEY: misc_feature
<222> LOCATION: (28)..(28)
<223> OTHER INFORMATION: an A or G
<220> FEATURE:
```

<221> NAME/KEY: misc_feature
<222> LOCATION: (29)..(29)
<223> OTHER INFORMATION: Independently selected from a modified
      nucleotide, specifically a modified pyrimidine

<400> SEQUENCE: 155
nangnggnnn nngggggnnnn anccgnnnng         30

<210> SEQ ID NO 156
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (14)..(16)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (25)..(25)
<223> OTHER INFORMATION: 5-(N-benzylcarboxyamide)-2'-deoxyuridine

<400> SEQUENCE: 156
tgaggacnng gggnnnagcc gnngng         26

<210> SEQ ID NO 157
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-(N-benzylcarboxyamide)-2'-deoxyuridine
<220> FEATURE:
<221> NAME/KEY: misc_feature
<222> LOCATION: (9)..(9)
<223> OTHER INFORMATION: 5-(N-benzylcarboxyamide)-2'-deoxyuridine
<220> FEATURE:
<221> NAME/KEY: misc_feature
<222> LOCATION: (14)..(16)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (25)..(25)
<223> OTHER INFORMATION: 5-(N-benzylcarboxyamide)-2'-deoxyuridine

<400> SEQUENCE: 157
ngaggactng gggnnnagcc gnngng         26

<210> SEQ ID NO 158
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-(N-benzylcarboxyamide)-2'-deoxyuridine

```
<220> FEATURE:
<221> NAME/KEY: misc_feature
<222> LOCATION: (8)..(8)
<223> OTHER INFORMATION: 5-(N-benzylcarboxyamide)-2'-deoxyuridine
<220> FEATURE:
<221> NAME/KEY: misc_feature
<222> LOCATION: (14)..(16)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (25)..(25)
<223> OTHER INFORMATION: 5-(N-benzylcarboxyamide)-2'-deoxyuridine

<400> SEQUENCE: 158
ngaggacntg gggnnnagcc gnngng                                         26

<210> SEQ ID NO 159
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-(N-benzylcarboxyamide)-2'-deoxyuridine
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (15)..(16)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (25)..(25)
<223> OTHER INFORMATION: 5-(N-benzylcarboxyamide)-2'-deoxyuridine

<400> SEQUENCE: 159
ngaggacnng gggtnnagcc gnngng                                         26

<210> SEQ ID NO 160
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-(N-benzylcarboxyamide)-2'-deoxyuridine
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (16)..(16)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
```

```
<220> FEATURE:
<221> NAME/KEY: misc_feature
<222> LOCATION: (25)..(25)
<223> OTHER INFORMATION: 5-(N-benzylcarboxyamide)-2'-deoxyuridine

<400> SEQUENCE: 160
ngaggacnng gggntnagcc gnngng                                               26

<210> SEQ ID NO 161
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-(N-benzylcarboxyamide)-2'-deoxyuridine
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (14)..(15)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (25)..(25)
<223> OTHER INFORMATION: 5-(N-benzylcarboxyamide)-2'-deoxyuridine

<400> SEQUENCE: 161
ngaggacnng gggnntagcc gnngng                                               26

<210> SEQ ID NO 162
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-(N-benzylcarboxyamide)-2'-deoxyuridine
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (14)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(23)
<223> OTHER INFORMATION: 5-(N-benzylcarboxyamide)-2'-deoxyuridine
<220> FEATURE:
<221> NAME/KEY: misc_feature
<222> LOCATION: (25)..(25)
<223> OTHER INFORMATION: 5-(N-benzylcarboxyamide)-2'-deoxyuridine

<400> SEQUENCE: 162
ngaggacnng gggnnnagcc gtngng                                               26

<210> SEQ ID NO 163
<211> LENGTH: 26
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(1)
<223> OTHER INFORMATION: 5-(N-benzylcarboxyamide)-2'-deoxyuridine
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (14)..(16)
<223> OTHER INFORMATION: 5-(N-benzylcarboxyamide)-2'-deoxyuridine
<220> FEATURE:
<221> NAME/KEY: misc_feature
<222> LOCATION: (22)..(22)
<223> OTHER INFORMATION: 5-(N-benzylcarboxyamide)-2'-deoxyuridine
<220> FEATURE:
<221> NAME/KEY: misc_feature
<222> LOCATION: (25)..(25)
<223> OTHER INFORMATION: 5-(N-benzylcarboxyamide)-2'-deoxyuridine

<400> SEQUENCE: 163
ngaggacnng gggnnnagcc gntgng                                   26

<210> SEQ ID NO 164
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-(N-benzylcarboxyamide)-2'-deoxyuridine
<220> FEATURE:
<221> NAME/KEY: misc_feature
<222> LOCATION: (8)..(9)
<223> OTHER INFORMATION: 5-(N-benzylcarboxyamide)-2'-deoxyuridine
<220> FEATURE:
<221> NAME/KEY: misc_feature
<222> LOCATION: (14)..(16)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine

<400> SEQUENCE: 164
ngaggacnng gggnnnagcc gnngtg                                   26

<210> SEQ ID NO 165
<211> LENGTH: 20
<212> TYPE: DNA
<213> ORGANISM: Artificial Sequence
<220> FEATURE:
<223> OTHER INFORMATION: Synthetic

<400> SEQUENCE: 165
ggtcttgttt cttctctgtg                                          20

<210> SEQ ID NO 166
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 5-(N-benzylcarboxyamide)-2'-deoxyuridine
<220> FEATURE:
<221> NAME/KEY: misc_feature
<222> LOCATION: (10)..(10)
<223> OTHER INFORMATION: 5-(N-benzylcarboxyamide)-2'-deoxyuridine
```

```
<220> FEATURE:
<221> NAME/KEY: misc_feature
<222> LOCATION: (16)..(17)
<223> OTHER INFORMATION: 5-(N-benzylcarboxyamide)-2'-deoxyuridine
<220> FEATURE:
<221> NAME/KEY: misc_feature
<222> LOCATION: (24)..(25)
<223> OTHER INFORMATION: 5-(N-benzylcarboxyamide)-2'-deoxyuridine
<220> FEATURE:
<221> NAME/KEY: misc_feature
<222> LOCATION: (27)..(27)
<223> OTHER INFORMATION: 5-(N-benzylcarboxyamide)-2'-deoxyuridine

<400> SEQUENCE: 166
cangaggacn tggggnntag ccgnngng                                           28

<210> SEQ ID NO 167
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (9)..(9)
<223> OTHER INFORMATION: 5-(N-benzylcarboxyamide)-2'-deoxyuridine
<220> FEATURE:
<221> NAME/KEY: misc_feature
<222> LOCATION: (15)..(16)
<223> OTHER INFORMATION: 5-(N-benzylcarboxyamide)-2'-deoxyuridine
<220> FEATURE:
<221> NAME/KEY: misc_feature
<222> LOCATION: (23)..(24)
<223> OTHER INFORMATION: 5-(N-benzylcarboxyamide)-2'-deoxyuridine
<220> FEATURE:
<221> NAME/KEY: misc_feature
<222> LOCATION: (26)..(26)
<223> OTHER INFORMATION: 5-(N-benzylcarboxyamide)-2'-deoxyuridine

<400> SEQUENCE: 167
angaggacnt ggggnntagc cgnngng                                            27

<210> SEQ ID NO 168
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-(N-benzylcarboxyamide)-2'-deoxyuridine
<220> FEATURE:
<221> NAME/KEY: misc_feature
<222> LOCATION: (8)..(8)
<223> OTHER INFORMATION: 5-(N-benzylcarboxyamide)-2'-deoxyuridine
<220> FEATURE:
<221> NAME/KEY: misc_feature
<222> LOCATION: (14)..(15)
<223> OTHER INFORMATION: 5-(N-benzylcarboxyamide)-2'-deoxyuridine
<220> FEATURE:
<221> NAME/KEY: misc_feature
<222> LOCATION: (22)..(23)
<223> OTHER INFORMATION: 5-(N-benzylcarboxyamide)-2'-deoxyuridine
<220> FEATURE:
<221> NAME/KEY: misc_feature
<222> LOCATION: (25)..(25)
<223> OTHER INFORMATION: 5-(N-benzylcarboxyamide)-2'-deoxyuridine

<400> SEQUENCE: 168
ngaggacntg gggnntagcc gnngng                                             26
```

```
<210> SEQ ID NO 169
<211> LENGTH: 28
<212> TYPE: DNA
<213> ORGANISM: Artificial Sequence
<220> FEATURE:
<223> OTHER INFORMATION: Synthetic

<400> SEQUENCE: 169
ttttttttgg tcttgtttct tctctgtg                                          28
```

APTAMERS TO β-NGF AND THEIR USE IN TREATING β-NGF MEDIATED DISEASES AND DISORDERS

RELATED APPLICATIONS

This application is a 35 U.S.C. §371 national phase application of PCT/US2011/032017, filed Apr. 12, 2010 (WO 2011/130195). PCT Application Serial No. PCT/US2011/032017 claims the benefit of U.S. Provisional Application Ser. No. 61/323,145, filed Apr. 12, 2010, which is incorporated herein by reference in its entirety.

Incorporated by reference herein in its entirety is the Sequence Listing entitled "Sequence_listing_ST25.txt", created Apr. 1, 2011, size of 126 kilobytes.

FIELD OF THE INVENTION

The present disclosure relates generally to the field of nucleic acids and more particularly to aptamers capable of binding to nerve growth factor, more specifically the β subunit of nerve growth factor ("β-NGF"), and useful as therapeutics for preventing, treating or ameliorating pruritus, pruritic conditions and/or other diseases or conditions in which β-NGF has been implicated. The disclosure further relates to materials and methods for the administration of aptamers capable of binding to β-NGF.

BACKGROUND

The following description provides a summary of information relevant to the present disclosure and is not an admission that any of the information provided or publications referenced herein is prior art to the present disclosure.

Severe itching negatively impacts the quality of life of millions of people every day. Severe itching may be associated with various health conditions, including pruritic skin conditions, such as scabies, eczema, xerosis, psoriasis and urticaria, as well as systemic conditions, including chronic hepatic or renal disease and lymphoma. Similarly, pain is a common occurrence, being one of the major reasons for visits to a physician. Pain may be associated with numerous types of injuries or conditions, and failure to treat acute pain may lead to chronic pain issues, as well as immune and metabolic disorders. In addition to reducing the quality of life for the individual suffering from pruritus and/or pain, there is a significant impact on healthcare budgets, particularly in relation to pruritic skin conditions, as well as, chronic pain disorders. Current efforts to manage or treat pruritus and/or pain are widely recognized as being inadequate.

Neurophysiological research has confirmed the distinctiveness of itch pathways in comparison with those of pain. The itch sensation is perceived and transmitted by dedicated C neurons which are distinct from the nociceptors that process pain sensation (Schmelz, Neurosci. Biobehav. Rev. doi: 10.1016/j.neubiorev.2008.12.004, 2009). The dedicated C neurons then transmit the itch stimulus to a specialized class of dorsal horn neurons projecting to the thalamus (Stander and Schmelz, Eur. J. Pain 10:473, 2006). There is believed to be no special itch receptor on peripheral nerve endings and the specificity of itch C neurons is based on their spinal connections to the itch pathway. Differences are observed in the brain activation patterns between itch and pain, such as an absence of detectable activation of the thalamic and somatosensory cortex of the parietal lobe from itch sensation (Yosipovitch et al., Lancet 361:690, 2003).

Pain is generally classified as either acute or chronic. Acute pain is commonly a response to tissue damage, characterized as short-lived and resolves as the initial damage heals. Chronic pain is persistent and may have no apparent association with a traumatic event. Pain may further be classified based on the mechanistic origin of the pain and includes nociceptive and non-nociceptive. Nociceptive pain is mediated by specific receptors (nociceptive receptors) that are activated by a specific stimulus (injury, inflammation, chemical, etc). Nociceptive pain may further be classified as somatic or visceral. Somatic pain occurs in tissues such as skin, muscle, joints, bones, or ligaments. Somatic pain is generally sharp and localized. Current treatments include use of opioids and non-steroidal anti-inflammatory drugs (NSAIDS). Visceral pain occurs in internal organs. It is frequently a poorly localized pain and is generally treated with opioids.

Non-nociceptive pain may be further broken down into neuropathic or sympathetic. Neuropathic pain may arise in the peripheral or central nervous system. Neuropathic pain may be associated with degenerative conditions, inflammation, or infectious diseases. This type of pain results in hypersensitivity (hyperalgesia) and is frequently described as shooting or burning. Treatment options include N-methyl-D-aspartate (NMDA) antagonists, anti-arrhthymics, anti-convulsants, or anti-depressants. Neuropathic pain is frequently resistant to conventional analgesics. Sympathetic pain arises in the sympathetic nervous system as well as the peripheral and central nervous systems and is generally associated with some type of injury. The site of injury may show increased hypersensitivity and abnormal temperature. Treatment generally involves a multi-drug regimen including sympathetic nerve blocks, vasodilatation, anti-convulsives, anti-arrhthymics, and anti-depressants.

Routine and prolonged treatment of pain with opioid analgesics is not recommended because of the concern for potential addiction, side effects, tolerance, and dependency on the opioid. Opioid side effects can include nausea, vomiting, constipation, respiratory depression, etc. With many current treatments there exists a lack of efficacy, serious side effects, and inability of drug delivery methods to help in adequate pain control. These issues support the need for better pain control therapeutics.

Although itch and pain are clearly distinct sensations, there are important interactions between itch and pain. It is well known that itch can be reduced by the painful sensation caused by scratching. Yet, analgesics, such as opioids, by acting to diminish pain sensations, can actually enhance itch sensation. Thus, some therapeutics for pain can exacerbate itch symptoms further supporting the need for better therapeutics with the potential to treat both itch and pain.

Nerve growth factor (NGF) is one of a family of neurotrophic cytokines or neurotrophins. Neurotrophins play a key role in the development and maintenance of both the peripheral and central nervous system by controlling cell survival, differentiation, and apoptosis. In addition to these nervous system functions, NGF has also been shown to increase the release of histamine, the production of mast cells, and the growth and differentiation of B lymphocytes. NGF has also been shown to modulate the basophilic production of certain lipid mediators. The apoptosis of neutrophils may also be suppressed by NGF. All of these factors suggest a role for NGF in the immune system as well as the nervous system.

The NGF beta chain (β-NGF) is solely responsible for the nerve growth stimulating activity of NGF. In the cell, β-NGF exists as a dimer and binds to two types of cell surface receptors in neuronal and non-neuronal cells. The tertiary structure of the protein is based on three cystine disulfides and two anti-parallel, β-strands. The amino acid homology of the human, mouse, and rat proteins are about 90%. β-NGF, like all of the neurotrophins, binds to the p75 cell receptor with nM affinity. β-NGF also binds to one of the tyrosine kinase receptors (Trk) in particular, TrkA, with pM affinity. Reaction with the p75 receptor can induce cell death while binding to TrkA promotes cell survival. β-NGF binding to TrkA leads to phosphorylation of the receptor and internal cellular proteins. β-NGF is internalized by receptor-mediated endocytosis. Trk receptors are found in a wide range of non-neuronal tissues.

Nerve growth factor (NGF) released from keratinocytes in the skin is one of the major mediators that increase dermal nerve density and affect morphology by, among other things, promoting sprouting of nerve fibers (Schmelz, Neurosci. Biobehav. Rev. doi:10.1016/j.neubiorev.2008.12.004, 2009). Patients with chronic pruritus have been found to exhibit increased intradermal nerve fiber density. Further, NGF has been found to increase sensitivity of peripheral neurons by, among other things, triggering the receptor of NGF, tyrosine kinase TrkA (Stander and Schmelz, Eur. J. Pain 10:473, 2006).

The importance of NGF in mediating pruritus as well as pain is exhibited in the high concentrations of NGF measured in atopic conditions, which may be symptomized by both pruritus and pain. Patients with atopic dermatitis have greatly increased serum levels of NGF which positively correlate with the severity of the condition. Patients with contact dermatitis have higher local NGF concentrations and patients with prurigo nodularis also exhibit higher NGF levels and TrkA activation levels (Schmelz, Neurosci. Biobehav. Rev. doi:10.1016/j.neubiorev.2008.12.004, 2009).

The effects of anti-NGF antibodies administered systemically by intraperitoneal injection on symptoms in a mouse model for atopic dermatitis having been studied and results "suggest that anti-NGF antibodies block the effects of NGF on the periphery of the nervous system and suppress epidermal innervations, dermatitis and scratching behavior" (Takano et al. J. Pharmacol Sci 99:277:284, 2005). Yet, the study found that anti-NGF antibodies did not alter serum NGF levels, did not decrease the NGF concentration in the skin areas tested, and did not completely suppress scratching behavior. Thus, a need to more completely reduce or eliminate itching associated with atopic dermatitis remains.

A growing body of evidence indicates that NGF functions as a mediator of certain pain states. It has been shown that anti-NGF antibodies can produce a sustained thermal and chemical analgesic effect, as well as block the hyperalgesia which develops from carrageenan-induced inflammation (McMahon et al., Nat. Med. 1:774, 1995). Studies of a small molecule NGF receptor antagonist for blockading the bioactivity of NGF have indicated an analgesic effect on neuropathic and inflammatory pain states (Owolabi et al., J. Pharmacol. Exp. Ther. 289:1271, 1999)). In the Owolabi et al. study, the analgesic effect of the small molecule NGF activity inhibitor may be less than that of morphine depending on the route of administration. Since opioids, such as morphine, have many unwanted side-effects, a need remains for providing analgesia in the variety of pain states mediated by NGF which allows flexibility in effective administration.

SUMMARY

The present disclosure provides various aptamers that bind to the beta subunit of nerve growth factor, referred to individually herein as a "β-NGF aptamer", and methods for using such β-NGF aptamers to treat β-NGF mediated diseases and disorders, including the treatment of pain and pruritus and pruritic conditions. Included are pharmaceutical compositions or formulations comprised of a β-NGF aptamer or a pharmaceutically acceptable salt thereof and at least one pharmaceutically acceptable carrier.

The compositions of the present disclosure can be prepared in any suitable pharmaceutically acceptable dosage form. The formulations and dosages described herein are designed to maximize clinical efficacy in the treatment of various conditions, such as pain and pruritus and pruritic conditions, while simultaneously decreasing or minimizing adverse side effects.

The present disclosure further provides methods for preventing, treating or ameliorating a disease or condition mediated by β-NGF, the methods comprising administering a β-NGF aptamer or a pharmaceutical composition of the β-NGF aptamer to a vertebrate, specifically a mammal, more specifically a human. Specifically, the present disclosure provides methods for treating, preventing or ameliorating pain and pruritus and pruritic conditions. In some aspects, the β-NGF mediated disease or condition is one in which β-NGF activity may directly or indirectly lead to pruritus at some stage of the disease. In some embodiments the disease or condition to be treated, prevented or ameliorated is dermatitis or eczema. In other embodiments, the disease or condition to be treated, prevented or ameliorated is atopic dermatitis.

In one embodiment, a therapeutic effect (e.g., treating, preventing or ameliorating pain and pruritus and pruritic conditions) may be achieved by administering a β-NGF aptamer such that the aptamer is exposed to, and can bind to, β-NGF regardless of the method of delivery of the aptamer to the patient being treated. In a related embodiment, the therapeutic effect may be achieved by the administration of the β-NGF aptamer such that it is exposed to, and binds to, β-NGF and thereby prevents or reduces the binding of β-NGF to one or more of its various cell receptors. In one embodiment, the cell receptor is p75. In another embodiment, the cell receptor is a Trk receptor. In yet another embodiment, the cell receptor is TrkA. In yet another embodiment, the β-NGF aptamer prevents or reduces the level of phosphorylation of the β-NGF receptor and other internal cellular proteins.

The provided methods encompass administration of the β-NGF aptamer in association with one or more secondary active agents. Such administration can be sequential or in a combination composition.

In another aspect, the present disclosure provides an in vitro diagnostic method comprising contacting a β-NGF aptamer with a sample suspected of comprising β-NGF. In another aspect, the present disclosure provides an in vivo diagnostic method comprising providing a suitably labeled β-NGF aptamer, injecting the aptamer into an individual suspected of having β-NGF-mediated disease or disorder, and detecting the labeled aptamer for the purpose of diagnosing or evaluating the health status of the individual. The label used will be selected in accordance with the imaging modality to be used.

BRIEF DESCRIPTION OF THE DRAWINGS

FIGS. 2A and 2B depict aptamer consensus sequences identified using 454 sequencing for aptamer 2426-66 (SEQ ID NO: 1).

FIG. 3 illustrates dimerization strategy #1 for a β-NGF aptamer.

DETAILED DESCRIPTION

Figure 1:
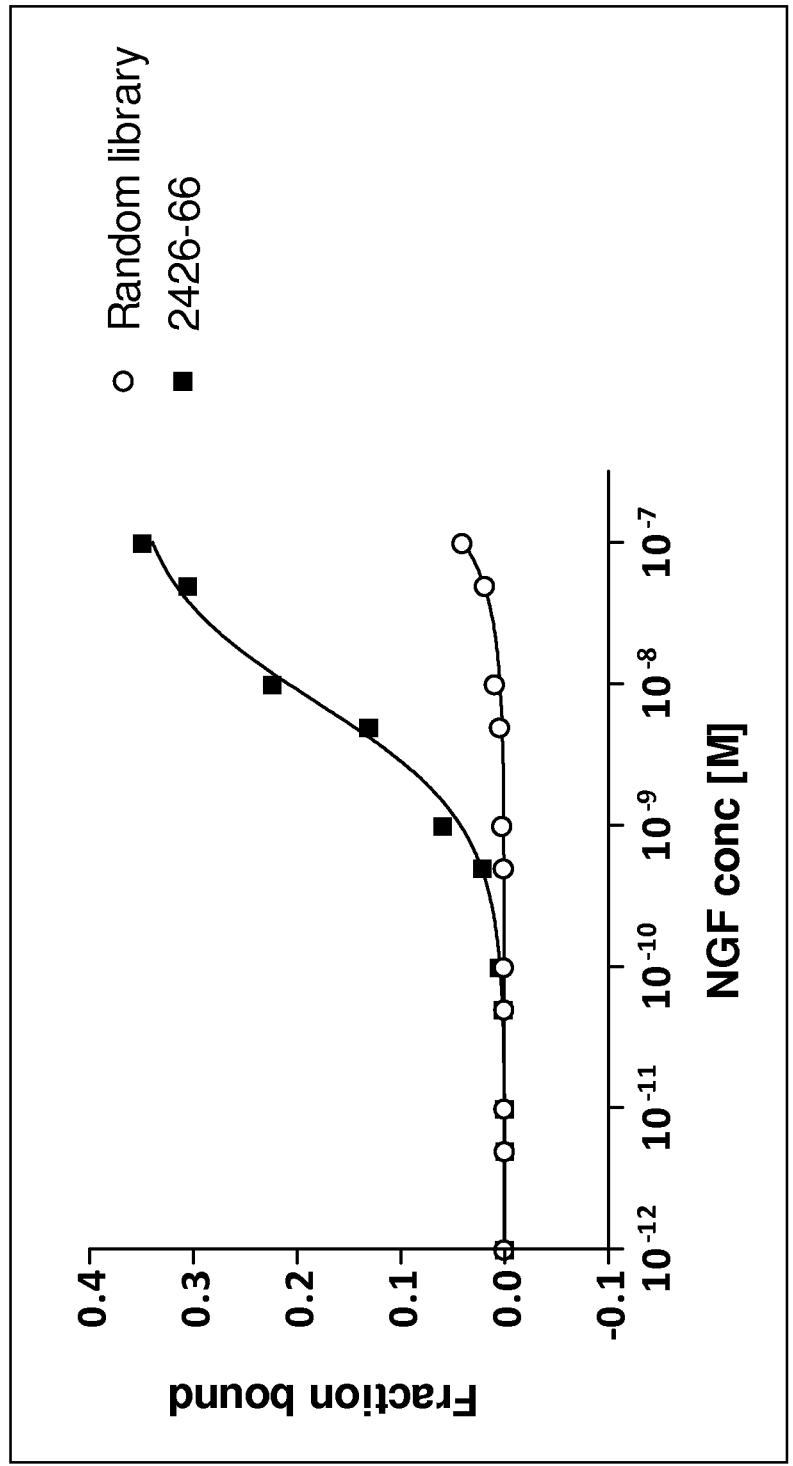
FIG. 1 illustrates the binding curves for aptamer 2426-66 (■) (SEQ ID NO: 1) compared to the random library (○).

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described.

Unless defined otherwise, technical and scientific terms used herein have the same meaning as commonly understood by one of ordinary skill in the art(s) to which this invention belongs. Although any methods, devices, and materials similar or equivalent to those described herein can be used in the practice or testing of the invention, the preferred methods, devices and materials are now described.

All publications, published patent documents, and patent applications cited in this disclosure are indicative of the level of skill in the art(s) to which the disclosure pertains. All publications, published patent documents, and patent applications cited herein are hereby incorporated by reference to the same extent as though each individual publication, published patent document, or patent application was specifically and individually indicated as being incorporated by reference.

As used in this disclosure, including the appended claims, the singular forms "a," "an," and "the" include plural references, unless the content clearly dictates otherwise, and are used interchangeably with "at least one" and "one or more." Thus, reference to "an aptamer" includes mixtures of aptamers, and the like.

As used herein, the term "about" represents an insignificant modification or variation of the numerical value such that the basic function of the item to which the numerical value relates is unchanged.

The term "each" when used herein to refer to a plurality of items is intended to refer to at least two of the items. It need not require that all of the items forming the plurality satisfy an associated additional limitation.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

As used herein, the term "nucleotide" refers to a ribonucleotide or a deoxyribonucleotide, or a modified form thereof, as well as an analog thereof. Nucleotides include species that include purines (e.g., adenine, hypoxanthine, guanine, and their derivatives and analogs) as well as pyrimidines (e.g., cytosine, uracil, thymine, and their derivatives and analogs).

As used herein, "nucleic acid," "oligonucleotide," and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included. The terms "polynucleotide," "oligonucleotide," and "nucleic acid" include double- or single-stranded molecules as well as triple-helical molecules. Nucleic acid, oligonucleotide, and polynucleotide are broader terms than the term aptamer and, thus, the terms nucleic acid, oligonucleotide, and polynucleotide include polymers of nucleotides that are aptamers but the terms nucleic acid, oligonucleotide, and polynucleotide are not limited to aptamers.

As used herein, the terms "modify", "modified", "modification", and any variations thereof, when used in reference to an oligonucleotide, means that at least one of the four constituent nucleotide bases (i.e., A, G, T/U, and C) of the oligonucleotide is an analog or ester of a naturally occurring nucleotide. In some embodiments, the modified nucleotide confers nuclease resistance to the oligonucleotide. A pyrimidine with a substitution at the C-5 position is an example of a modified nucleotide. Modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in one embodiment ranging from about 10 to about 80 kDa, PEG polymers in another embodiment ranging from about 20 to about 60 kDa, or other hydrophilic or hydrophobic biological or synthetic polymers. In one embodiment, modifications are of the C-5 position of pyrimidines. These modifications can be produced through an amide linkage directly at the C-5 position or by other types of linkages.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

Figure 10:
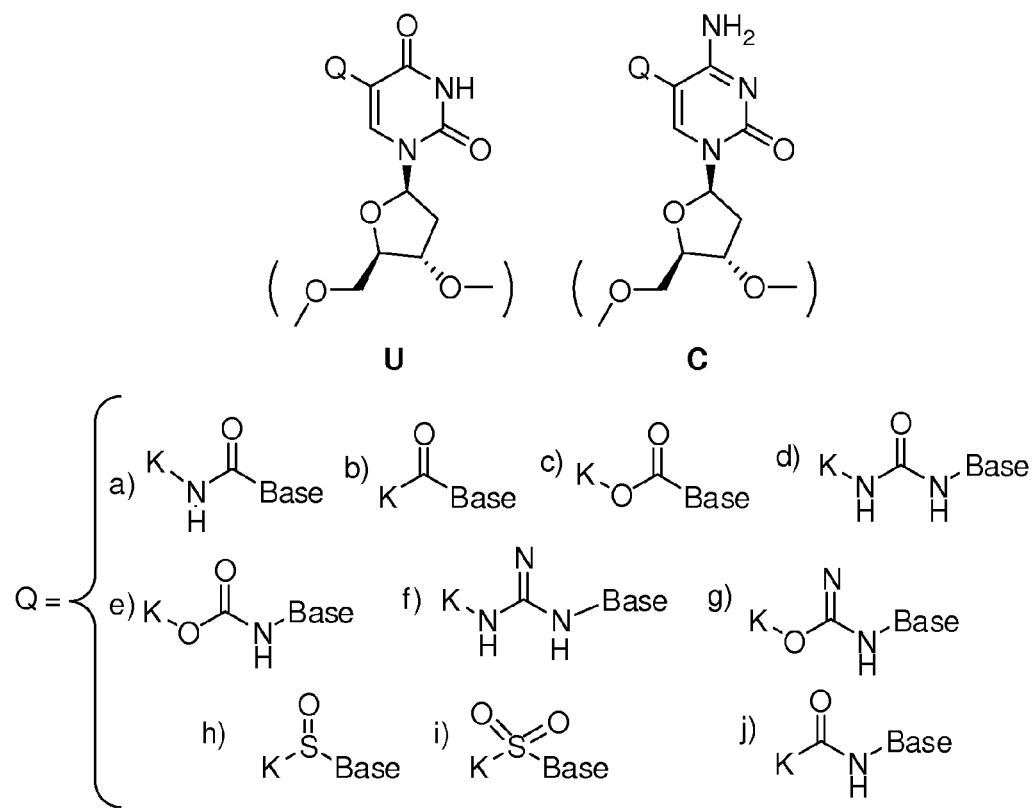
FIG. 10 depicts C-5 pyrimidine modifications used to prepare the aptamers described herein.
Figure 10:
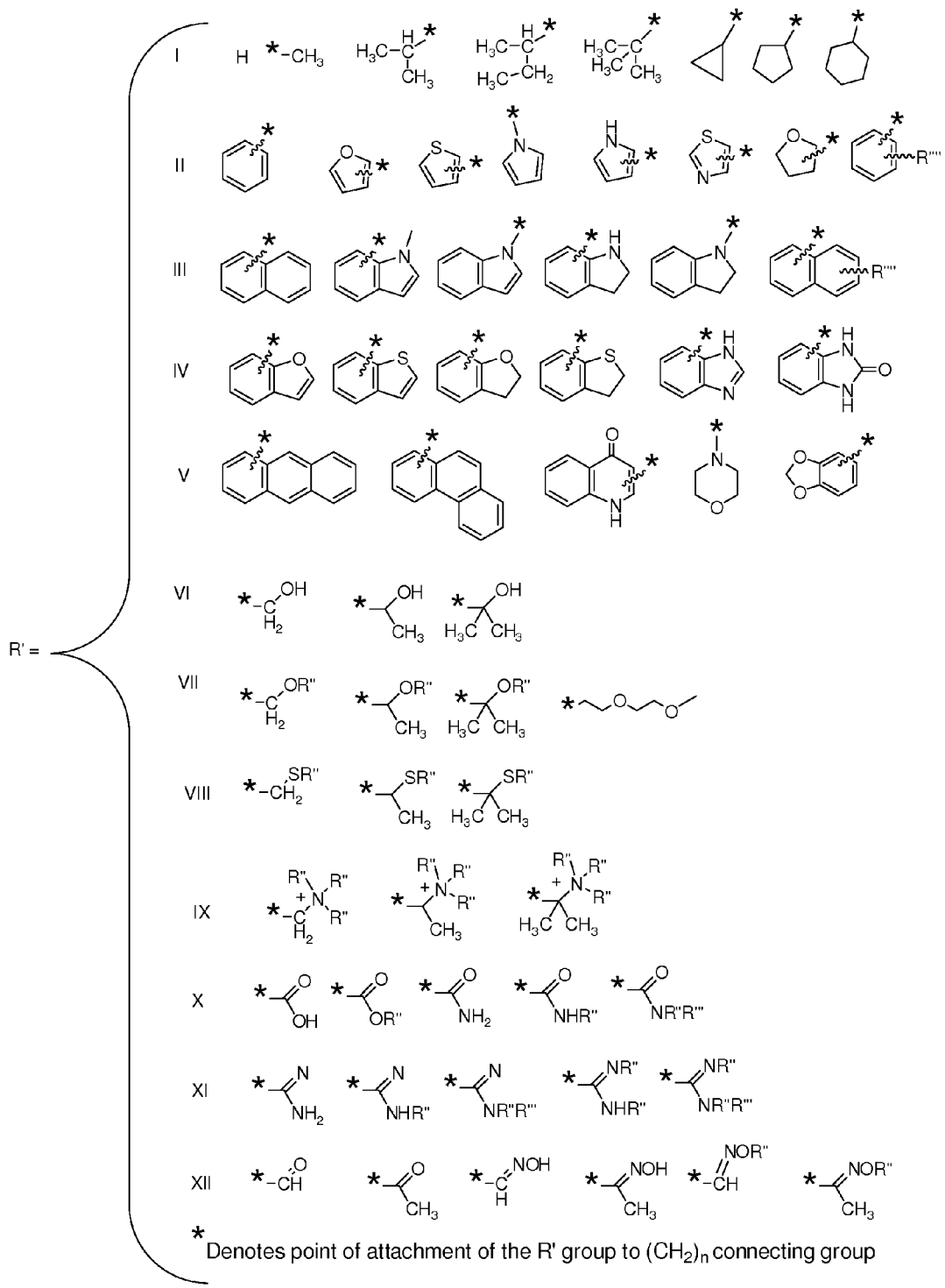

As used herein, the term "C-5 modified pyrimidine" refers to a pyrimidine with a modification at the C-5 position including, but not limited to, those moieties illustrated in FIG. 10. Examples of a C-5 modified pyrimidine include those described in U.S. Pat. Nos. 5,719,273 and 5,945,527, as well as, U.S. Provisional Application Ser. No. 61/264,545, filed Nov. 25, 2009, entitled "Nuclease Resistant Oligonucleotides." Examples of a C-5 modification include substitution of deoxyuridine at the C-5 position with a substituent independently selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), and isobutylcarboxyamide (alternatively isobutylaminocarbonyl) (iBu) as illustrated immediately below.

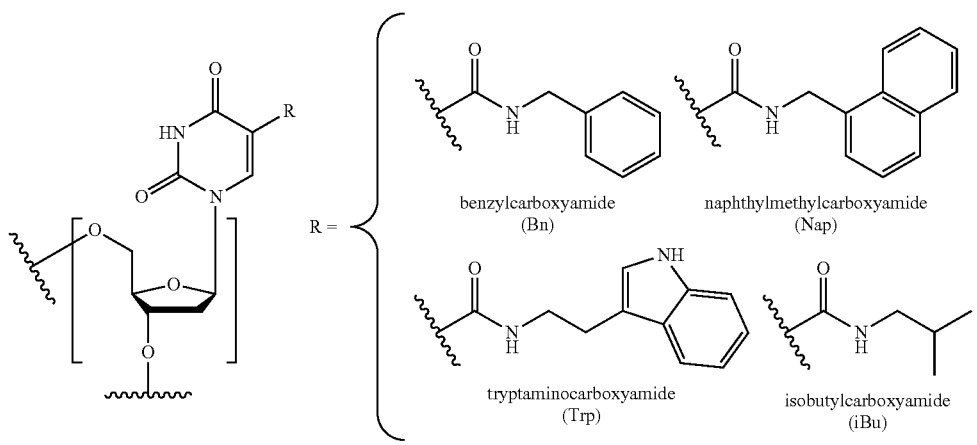

Chemical modifications of a C-5 modified pyrimidine can also be combined with, singly or in any combination, 2'-position sugar modifications, modifications at exocyclic amines, and substitution of 4-thiouridine and the like.

Representative C-5 modified pyrimidines include: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine or 5-(N-[1-(2,3-dihydroxypropyl)]carboxyamide)-2'-deoxyuridine).

If present, a modification to the nucleotide structure can be imparted before or after assembly of a polymer. A sequence of nucleotides can be interrupted by non-nucleotide components. A polynucleotide can be further modified after polymerization, such as by conjugation with a labeling component.

As used herein, the term "at least one pyrimidine," when referring to modifications of a nucleic acid, refers to one, several, or all pyrimidines in the nucleic acid, indicating that any or all occurrences of any or all of C, T, or U in a nucleic acid may be modified or not.

As used herein, "nucleic acid ligand," "aptamer," and "clone" are used interchangeably to refer to a non-naturally occurring nucleic acid that has a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule. In one embodiment, the action is specific binding affinity for a target molecule, such target molecule being a three dimensional chemical structure other than a polynucleotide that binds to the nucleic acid ligand through a mechanism which is independent of Watson/Crick base pairing or triple helix formation, wherein the aptamer is not a nucleic acid having the known physiological function of being bound by the target molecule. Aptamers to a given target include nucleic acids that are identified from a candidate mixture of nucleic acids, where the aptamer is a ligand of the target, by a method comprising: (a) contacting the candidate mixture with the target, wherein nucleic acids having an increased affinity to the target relative to other nucleic acids in the candidate mixture can be partitioned from the remainder of the candidate mixture; (b) partitioning the increased affinity nucleic acids from the remainder of the candidate mixture; and (c) amplifying the increased affinity nucleic acids to yield a ligand-enriched mixture of nucleic acids, whereby aptamers of the target molecule are identified. It is recognized that affinity interactions are a matter of degree; however, in this context, the "specific binding affinity" of an aptamer for its target means that the aptamer binds to its target generally with a much higher degree of affinity than it binds to other, non-target, components in a mixture or sample. An "aptamer" or "nucleic acid ligand" is a set of copies of one type or species of nucleic acid molecule that has a particular nucleotide sequence. An aptamer can include any suitable number of nucleotides. "Aptamers" refer to more than one such set of molecules. Different aptamers can have either the same or different numbers of nucleotides. Aptamers may be DNA or RNA and may be single stranded, double stranded, or contain double stranded or triple stranded regions.

As used herein, "protein" is used synonymously with "peptide," "polypeptide," or "peptide fragment." A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "modulate" means to alter, either by increasing or decreasing, the level of a peptide or polypeptide, or to alter, either by increasing or decreasing, the stability or activity of a peptide or a polypeptide. The term "inhibit" means to decrease the level of a peptide or a polypeptide or to decrease the stability or activity of a peptide or a polypeptide. As described herein, the protein which is modulated or inhibited is β-NGF.

As used herein, the term "bioactivity" indicates an effect on one or more cellular or extracellular process (e.g., via binding, signaling, etc.) which can impact physiological or pathophysiological processes.

As used herein, the terms "nerve growth factor," "NGF," and "β-NGF" refer to the beta subunit of nerve growth factor and variants thereof that retain at least part of the activity of NGF. As used herein, NGF includes all mammalian species of native sequence NGF, including human, canine, feline, murine, primate, equine, and bovine.

As used herein, "NGF receptor" refers to a polypeptide that is bound by or activated by NGF. NGF receptors include the TrkA receptor and the p75 receptor of any mammalian species, including, but are not limited to, human, canine, feline, murine, equine, primate, and bovine.

A "β-NGF aptamer" is an aptamer that is capable of binding to and modifying the activity of β-NGF. As used herein, a "β-NGF aptamer" refers to an aptamer which is able to bind to β-NGF and/or inhibit β-NGF biological activity and/or downstream pathway(s) mediated by NGF signaling.

As used herein, "disease or medical condition mediated by β-NGF" refers to diseases or medical conditions in which β-NGF activity may directly or indirectly lead to pain or pruritus at some stage in the disease process, including any of the diseases or medical conditions listed in Table 7. Thus, treatment with a β-NGF aptamer inhibits the pain or pruritus that occurs due to β-NGF activity in these diseases or medical conditions. The aptamer to β-NGF may further block the binding of β-NGF to one or more of its receptors.

As used herein, "pain" refers to acute pain, chronic pain, nociceptive pain, visceral pain, somatic pain, non-nociceptive pain, neuropathic pain, sympathetic pain, or to pain related to β-NGF mediated inflammation processes.

The term "pruritus" refers to itching which can range from a mild sensation to an intense sensation of itching pain. The itching may accompany primary skin disease or may be a symptom of systemic disease—sometimes the only symptom. Skin diseases in which itching can be most severe include, among others, scabies, pediculosis, insect bites, xerosis, urticaria, atopic dermatitis, contact dermatitis, lichen planus, miliaria and dermatitis herpetiformis. Systemic causes of pruritus include chronic hepatic or renal disease and lymphoma.

The terms "skin disorder" and "skin disease" refer to any disease or condition that affects or involves the skin, including skin conditions such as atopic dermatitis, ichthyosis, xeroderma, seborrheic dermatitis, allergic contact dermatitis, alopecia, pemphigus, dermatitis herpetiformis, psoriasis, candidiasis, acne, dermatophytosis, diaper rash, cradle cap, eczema, hookworm and skin damage from, e.g., wounds, burns, and fecal and urinary incontinence.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to, such sterile liquids as water and oils.

A "pharmaceutically acceptable salt" or "salt" of a β-NGF aptamer is a product of the disclosed compound that contains an ionic bond and is typically produced by reacting the disclosed compound with either an acid or a base, suitable for administering to an individual. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising a β-NGF aptamer in a form suitable for administration to an individual. A pharmaceutical composition is typically formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

As used herein, the term "therapeutically effective amount" generally means the amount necessary to ameliorate at least one symptom of a disorder or condition to be prevented, reduced, or treated as described herein. The phrase "therapeutically effective amount" as it relates to the β-NGF aptamers of the present disclosure means the aptamer dosage that provides the specific pharmacological response for which the aptamer is administered in a significant number of individuals in need of such treatment. It is emphasized that a therapeutically effective amount of an aptamer that is administered to a particular individual in a particular instance will not always be effective in treating the conditions/diseases described herein, even though such dosage is deemed to be a therapeutically effective amount by those of skill in the art.

The SELEX Method

The terms "SELEX" and "SELEX process" are used interchangeably herein to refer generally to a combination of (1) the selection of nucleic acids that interact with a target molecule in a desirable manner, for example binding with high affinity to a protein, with (2) the amplification of those selected nucleic acids. The SELEX process can be used to identify aptamers with high affinity to a specific target molecule or biomarker.

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands." The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-NH$_2$), 2'-fluoro (2'-F), and/or 2'-O-methyl (2'-OMe). See also, U.S. Patent Application Publication No. 20090098549, entitled "SELEX and PHOTOSELEX," which describes nucleic acid libraries having expanded physical and chemical properties and their use in SELEX and photoSELEX.

U.S. Provisional Application Ser. No. 61/264,545, filed Nov. 25, 2009, entitled "Nuclease Resistant Oligonucleotides," describes methods for producing oligonucleotides with improved nuclease resistance. The nuclease resistant oligonucleotides include at least one pyrimidine modified at the C-5 position with a group selected from those set forth in FIG. 10. In various embodiments, the modifications include substitution of deoxyuridine at the C-5 position with a substituent independently selected from: benzylcarboxyamide (Bn), naphthylmethylcarboxyamide (Nap), tryptaminocarboxyamide (Trp), and isobutylcarboxyamide as illustrated above.

SELEX can also be used to identify aptamers that have desirable off-rate characteristics. See U.S. Patent Publication No. 20090004667, entitled "Method for Generating Aptamers with Improved Off-Rates," which describes improved SELEX methods for generating aptamers that can bind to target molecules. Methods for producing aptamers and photoaptamers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates dissociate and do not reform, while complexes with slow dissociation rates remain intact. Additionally, the methods include the use of modified nucleotides in the production of candidate nucleic acid mixtures to generate aptamers with improved off-rate performance (see U.S. Patent Publication No. 20090098549, entitled "SELEX and PhotoSELEX").

"Target" or "target molecule" or "target" refers herein to any compound upon which a nucleic acid can act in a desirable manner A target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc., without limitation. Virtually any chemical or biological effector may be a suitable target. Molecules of any size can serve as targets. A target can also be modified in certain ways to enhance the likelihood or strength of an interaction between the target and the nucleic acid. A target can also include any minor variation of a particular compound or molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule" or "target" is a set of copies of one type or species of molecule or multimolecular structure that is capable of binding to an aptamer. "Target molecules" or "targets" refer to more than one such set of molecules. Embodiments of the SELEX process in which the target is a peptide are described in U.S. Pat. No. 6,376,190, entitled "Modified SELEX Processes Without Purified Protein." In the instant case, the target is β-NGF.

Aptamers

The aptamers of the instant disclosure were identified using the improved SELEX method for identifying aptamers having slow off-rates as described in Example 1, which describes a representative method for the selection and production of a DNA aptamer to β-NGF. The form of β-NGF used in the selection process was a recombinant human protein and was isolated as the monomeric form of the protein with a molecular weight of 13.2 kD. In solution the monomer forms a dimer. Using this method, the DNA aptamer to β-NGF designated as aptamer 2426-66 (SEQ ID NO: 1) was identified.

Using aptamer 2426-66 (SEQ ID NO: 1), studies were conducted to identify the minimum sequence length required to maintain strong affinity for β-NGF as described in Example 2. Minimizing the sequence length allows for more reproducible aptamer synthesis in a chemical process and potentially aids in adsorption through the skin as well as incorporation into a pharmaceutical formulation. The truncation studies led to the identification of aptamers having a number of truncated sequences that were also avid binders to β-NGF, with $K_d$ values up to about 30 nM. These sequences include SEQ ID NOS: 1, 2, 9-44, and 149 (Tables 3 and 4). In particular aptamer 2426-66-50 (SEQ ID NO: 2; Table 4), a 28-mer having a $K_d$ of 1.4 nM for β-NGF was identified.

Additional sequencing studies were conducted on the sequence pool from which 2426-66 (SEQ ID NO: 1) was selected. The sequencing method used was 454 Sequencing. This is a large-scale, high throughput method that uses parallel pyrosequencing. The method provides unbiased sample preparation and very accurate sequence analysis. In this method, biotinylated DNA fragments are captured on streptavidin beads and then amplified by PCR. The unbiotinylated strand is released from the bead and used as a single stranded template DNA library. This library is then amplified by PCR. Each bead then contains amplified, clonal copies of the DNA fragments. This library of beads is then used in an enzymatic sequencing process. The sequencing data was used to identify a consensus sequence for a β-NGF aptamer. Furthermore, nucleotide substitution studies described in Example 3 led to the discovery that seven of nine BndU positions in the consensus sequence were desirable for β-NGF binding, but two BndU positions could be replaced with dT with no loss of binding activity. The consensus sequence is shown in FIG. 2A, along with a graphic representation of the nucleotide frequency at each position relative to the 2426-66 (SEQ ID NO: 1) aptamer. As illustrated in FIG. 2A, the consensus sequence is:

```
                                   (SEQ ID NO: 45)
BAZGRGGRSZWGGGGZZWADCCGZZRZG
``` wherein

B is selected from any nucleotide other than A;

R is independently selected from an A or G;

S is selected from a C or G;

W is independently selected from a Z or T;

D is selected from any nucleotide other than C; and

Z is independently selected from a modified nucleotide, specifically a modified pyrimidine.

In one aspect, B is selected from a C, G or Z; D is selected from an A, G or Z and R, S, W and Z are as defined above.

In another aspect, the consensus sequence is:

```
                                    (SEQ ID NO: 3)
BAZGRGGRSZZGGGGZZZADCCGZZRZG
``` wherein B, R, S, D and Z are as defined above.

In some embodiments, Z is a modified uridine. In other embodiments, Z is C-5 modified pyrimidine as defined above. In yet other embodiments, Z is a C-5 modified pyrimidine independently selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-β-methyluridine, 5-(N-tryptaminocarboxyamide)-2'-fluorouridine, 5-(N-[1-(3-trimethylamonium) propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine and 5-(N-[1-(2,3-dihydroxypropyl)]carboxyamide)-2'-deoxyuridine). In other embodiments, Z is 5-(N-benzylcarboxyamide)-2'-deoxyuridine (BndU). Any of these nucleotide modifications are anticipated to be equally effective in promoting high affinity binding to β-NGF and providing a slow off rate.

As used herein, "consensus sequence", when used in reference to a series of related nucleic acids, refers to a nucleotide sequence that reflects the most common choice of base at each position in the sequence where the series of related nucleic acids has been subjected to intensive mathematical and/or sequence analysis.

The present disclosure provides β-NGF aptamers identified using the SELEX method and listed in Tables 3 and 4 (SEQ ID NOS: 1, 2, 9-44 and 149). Aptamers to β-NGF that are substantially homologous to any of the listed aptamers and that have a substantially similar ability to bind β-NGF as that of an aptamer selected from the group of aptamers set forth in Tables 3 and 4 (SEQ ID NOS: 1, 2, 9-44 and 149) are also encompassed by the present disclosure. Further, aptamers to β-NGF that have substantially the same structural form as the aptamers identified herein and that have a substantially similar ability to bind β-NGF as that of an aptamer selected from the group of aptamers set forth in Tables 3 and 4 (SEQ ID NOS: 1, 2, 9-44 and 149) are also encompassed by the present disclosure.

In one aspect, the present disclosure provides an aptamer that specifically binds to β-NGF and includes a primary nucleic acid sequence. In one embodiment, the primary nucleic acid sequence is selected from SEQ ID NOS: 1, 2, 9-44 and 149. In other embodiments, the primary nucleic acid sequence is selected such that it is at least about 75% identical, at least about 80% identical, at least about 85% identical, at least about 90% identical, or at least about 95% identical to a primary nucleic acid sequence selected from SEQ ID NOS: 1, 2, 9-44 and 149.

The terms "sequence identity", "percent sequence identity", "percent identity", "% identical", "% identity", and variations thereof, when used in the context of two or more nucleic acid sequences, are used interchangeably to refer to two or more sequences or subsequences that are the same or have a specified percentage of nucleotides that are the same, when compared and aligned for maximum correspondence, as measured using a sequence comparison algorithm or by visual inspection. For sequence comparisons, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith and Waterman, Adv. Appl. Math., 2:482, 1981, by the homology alignment algorithm of Needleman and Wunsch, J. Mol. Biol., 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel, F. M. et al., Current Protocols in Molecular Biology, pub. by Greene Publishing Assoc. and Wiley-Interscience (1987)).

One example of an algorithm that is suitable for determining percent sequence identity is the algorithm used in the basic local alignment search tool (hereinafter "BLAST"), see, e.g. Altschul et al., J. Mol. Biol. 215:403-410, 1990 and Altschul et al., Nucleic Acids Res., 15:3389-3402, 1997. Software for performing BLAST analyses is publicly available through the National Center for Biotechnology Information (hereinafter "NCBI"). The default parameters used in determining sequence identity using the software available from NCBI, e.g., BLASTN (for nucleotide sequences) are described in McGinnis et al., Nucleic Acids Res., 32:W20-W25, 2004.

As used herein, when describing the percent identity of a nucleic acid, such as a β-NGF aptamer, the sequence of which is at least, for example, about 95% identical to a reference nucleotide sequence, it is intended that the nucleic acid sequence is identical to the reference sequence except that the nucleic acid sequence may include up to five point mutations per each 100 nucleotides of the reference nucleic acid sequence. In other words, to obtain a desired nucleic acid sequence, the sequence of which is at least about 95% identical to a reference nucleic acid sequence, up to 5% of the nucleotides in the reference sequence may be deleted or substituted with another nucleotide, or some number of nucleotides up to 5% of the total number of nucleotides in the reference sequence may be inserted into the reference sequence (referred to herein as an insertion). These mutations of the reference sequence to generate the desired sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be any one of the entire nucleotide sequences shown in SEQ ID NOS: 1, 2, 9-44 and 149, or any fragment of any of these sequences.

In one aspect, each of the consensus sequences of SEQ ID NO: 45 or SEQ ID NO: 3 can be modified to include at least one insertion. In one embodiment, the consensus sequences of either SEQ ID NO: 45 or SEQ ID NO: 3 is modified such that one nucleotide (N) is inserted into the consensus sequence between bases 9 and 10. In another embodiment, the consensus sequence of either SEQ ID NO: 45 or SEQ ID NO: 3 is modified such that one nucleotide (N) is inserted into the consensus sequence between bases 15 and 16. In another embodiment, the consensus sequences of either SEQ ID NO: 45 or SEQ ID NO: 3 is modified such that one nucleotide (N) is inserted into the consensus sequence between bases 9 and 10 and an additional nucleotide (N) is inserted into the consensus sequence between bases 15 and 16. These embodiments are as illustrated as follows:

```
                                              (SEQ ID NO: 154)
BAZGRGGRSN(0-1)ZWGGGGN(0-1)ZZWADCCGZZRZG (SEQ ID NO: 155)
BAZGRGGRSN(0-1)ZZGGGGN(0-1)ZZZADCCGZZRZG
``` wherein B, R, S, D and Z are as defined above and N is independently selected from any naturally occurring or modified nucleotide (A, C, G, or T).

In another aspect, the present disclosure provides a β-NGF aptamer that, upon binding β-NGF, modulates a β-NGF function. In various embodiments, the aptamer modulates a β-NGF function in vivo. In various embodiments, the β-NGF aptamer includes a sequence of contiguous nucleotides that are identical to a sequence of contiguous nucleotides included in any of SEQ ID NOS: 1, 2, 9-44 and 149. In various embodiments, the sequence of contiguous nucleotides in the β-NGF aptamer can include any number of nucleotides that are identical to the same number of nucleotides in a sequence of contiguous nucleotides included in any of SEQ ID NOS: 1, 2, 9-44 and 149. In various embodiments, the sequence of contiguous nucleotides in the β-NGF aptamer includes a sequence of from about 4 to about 30 contiguous nucleotides that are identical to a sequence of from about 4 to about 30 contiguous nucleotides included in any of SEQ ID NOS: 1, 2, 9-44 and 149. In an exemplary embodiment, the β-NGF aptamer includes a sequence of 30 contiguous nucleotides that are identical to a sequence of 30 contiguous nucleotides included in any of SEQ ID NOS: 1, 2, 9-44 and 149. In another exemplary embodiment, the β-NGF aptamer includes a sequence of 20 contiguous nucleotides that are identical to a sequence of 20 contiguous nucleotides included in any of SEQ ID NOS: 1, 2, 9-44 and 149. In yet another exemplary embodiment, the β-NGF aptamer includes a sequence of 8 contiguous nucleotides that are identical to a sequence of 8 contiguous nucleotides included in any of SEQ ID NOS: 1, 2, 9-44 and 149. In yet another exemplary embodiment, the β-NGF aptamer includes a sequence of 4 contiguous nucleotides that are identical to a sequence of 4 contiguous nucleotides included in any of SEQ ID NOS: 1, 2, 9-44 and 149.

In one embodiment, the β-NGF aptamer is SEQ ID NO: 1. In another embodiment, the β-NGF aptamer is SEQ ID NO: 2. In yet another embodiment, the β-NGF aptamer is derived from the consensus sequence of SEQ ID NO: 3. In other embodiments, the β-NGF aptamer is any of SEQ ID NOS: 9-44 and 149. In one embodiment, the β-NGF aptamer is at least about 95% identical, at least about 90% identical, at least about 85% identical, at least about 80% identical, or at least about 75% identical to any of SEQ ID NOS: 1, 2, 9-44 and 149. In another embodiment, the β-NGF aptamer includes a sequence from any of SEQ ID NOS: 1, 2, 9-44 and 149 and fragments of any of these.

The β-NGF aptamer can contain any number of nucleotides in addition to the β-NGF binding region. In various embodiments, the β-NGF aptamer can include up to about 100 nucleotides, up to about 95 nucleotides, up to about 90 nucleotides, up to about 85 nucleotides, up to about 80 nucleotides, up to about 75 nucleotides, up to about 70 nucleotides, up to about 65 nucleotides, up to about 60 nucleotides, up to about 55 nucleotides, up to about 50 nucleotides, up to about 45 nucleotides, up to about 40 nucleotides, up to about 35 nucleotides, up to about 30 nucleotides, up to about 25 nucleotides, and up to about 20 nucleotides.

In yet another embodiment, the β-NGF aptamer is selected from an aptamer that has similar binding characteristics and ability to treat β-NGF associated pain or pruritus and pruritic conditions as an aptamer selected from the group consisting of SEQ ID NOS: 1, 2, 9-44 and 149.

The β-NGF aptamer can be selected to have any suitable dissociation constant ($K_d$) for β-NGF. In an exemplary embodiment, the β-NGF aptamer has a dissociation constant ($K_d$) for β-NGF of about 10 nM or less. In another exemplary embodiment, the β-NGF aptamer has a dissociation constant ($K_d$) for β-NGF of about 15 nM or less. In yet another exemplary embodiment, the β-NGF aptamer has a dissociation constant ($K_d$) for β-NGF of about 20 nM or less. In yet another exemplary embodiment, the β-NGF aptamer has a dissociation constant ($K_d$) for β-NGF of about 25 nM or less. A suitable dissociation constant can be determined with a binding assay using a multi-point titration and fitting the equation y=(max−min)(Protein)/($K_d$+Protein)+min as described in Example 1, below. It is to be understood that the determination of dissociation constants is highly dependent upon the conditions under which they are measured and thus these numbers may vary significantly with respect to factors such as equilibration time, etc. In other embodiments, the β-NGF aptamer is an aptamer with a $K_d$ that is less than or equal to the $K_d$ of an aptamer selected from SEQ ID NOS: 1, 2, 9-44 and 149.

Figure 4:
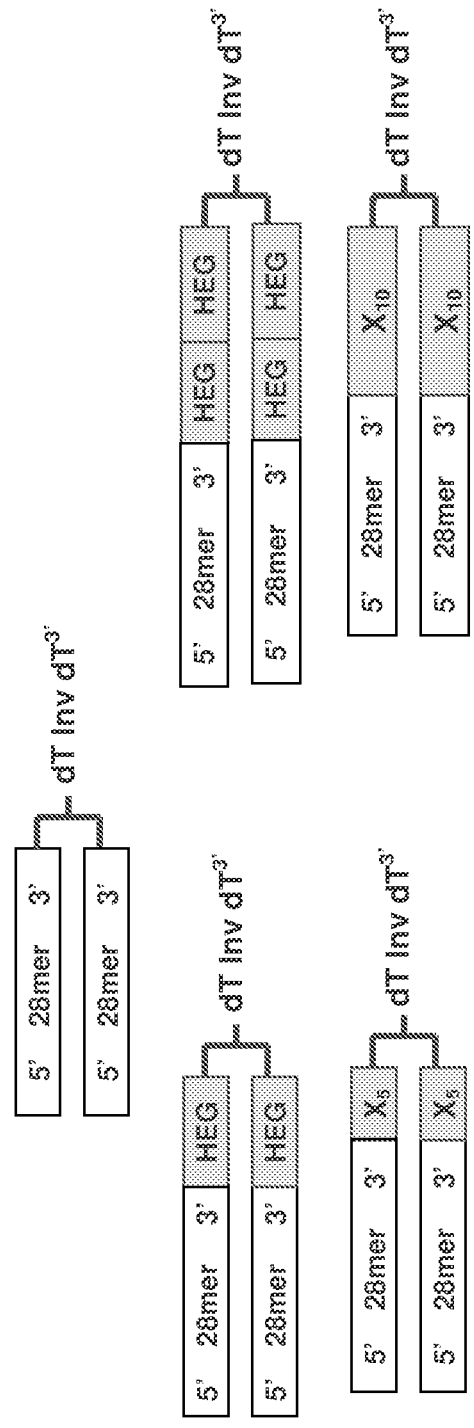
FIG. 4 illustrates dimerization strategy #2 for a β-NGF aptamer.

Aptamer 2426-66 (SEQ ID NO: 1) binds in a 1:1 stoichiometry with β-NGF monomer. Since the β-NGF forms a tight homodimer that is required for reaction with its target receptors, a more efficient inhibition of β-NGF activity might be achieved by using a dimeric or other multimeric form of the 2426-66 aptamer. Thus, in another embodiment, the β-NGF aptamer is a multimerization of any combination of the above sequences. FIGS. 3 and 4 illustrate potential approaches to the dimerization of the 2426-66 aptamer. The same strategies could be applied to any aptamer sequence with the appropriate binding characteristics for β-NGF. Similar approaches could also be used to create multimeric aptamers with as many copies of the aptamer sequence as desired. In this case, the 2426-66-50 (SEQ ID NO: 2) sequence of the truncated aptamer is used, but the full length 2426-66 sequence could also be utilized. FIG. 3 illustrates a head to tail construct of two 2426-66 sequences with either, one or more, hexaethylene glycol (HEG) or abasic sugar phosphates as linkers between the two sections of the new aptamer sequence. FIG. 4 depicts a dimerization of the 2426-66 sequence through the use of a branched phosphoramidite optionally including either hexaethylene glycol (HEG) or abasic sugar phosphates as linkers.

Pharmaceutical Compositions Including a β-NGF Aptamer

The present disclosure encompasses pharmaceutical compositions that include at least one aptamer to β-NGF and at least one pharmaceutically acceptable carrier. Suitable carriers are described in "Remington: The Science and Practice of Pharmacy, Twenty-first Edition," published by Lippincott Williams & Wilkins, which is incorporated herein by reference. Pharmaceutical compositions that include at least one aptamer to β-NGF and at least one pharmaceutically acceptable carrier may also include one or more active agents that is not a β-NGF inhibitor.

The aptamers described herein can be utilized in any pharmaceutically acceptable dosage form, including but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the aptamers described herein can be formulated: (a) for administration selected from any of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from any of liquid dispersions, gels, aerosols, ointments, creams, tablets, sachets and capsules; (c) into a dosage form selected from any of lyophilized formulations, dry powders, fast melt formulations, controlled release formulations, delayed release formulations, extended release formulations, pulsatile release formulations, and mixed immediate release and controlled release formulations; or (d) any combination thereof.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition should be sterile and should be fluid to the extent that easy syringability exists. The pharmaceutical composition should be stable under the conditions of manufacture and storage and should be preserved against the contaminating action of microorganisms such as bacteria and fungi. The term "stable", as used herein, means remaining in a state or condition that is suitable for administration to a patient.

The carrier can be a solvent or dispersion medium, including, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent (e.g., a β-NGF aptamer) in the required amount in an appropriate solvent with one or a combination of ingredients enumerated above, as required, followed by filtered sterilization. Generally, dispersions are prepared by incorporating at least one β-NGF aptamer into a sterile vehicle that contains a basic dispersion medium and any other required ingredient. In the case of sterile powders for the preparation of sterile injectable solutions, exemplary methods of preparation include vacuum drying and freeze-drying, both of which will yield a powder of the β-NGF aptamer plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the β-NGF aptamer can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from a pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the β-NGF aptamer is formulated for topical administration. As used herein "topical administration" refers to the delivery of a β-NGF aptamer to an animal by contacting, directly or otherwise, a formulation comprising the β-NGF aptamer to all or a portion of the skin (epidermis) of an animal. The term encompasses several routes of administration including, but not limited to, topical and transdermal. A common requirement for these modes of administration is efficient delivery to the target tissue or stratum. In one aspect, topical administration is used as a means to penetrate the epidermis and dermis and ultimately achieve systemic delivery of the β-NGF aptamer. In another aspect, topical administration is used as a means to selectively deliver the β-NGF aptamer to the epidermis or dermis of an animal, or to specific strata thereof.

For topical administration, the β-NGF aptamer may be formulated into pharmaceutically acceptable ointments, creams, lotions, eye ointments, eye drops, ear drops, impregnated dressings, and aerosols, medicated powders, medicated adhesives, foams, and may contain appropriate conventional additives or excipients, including, for example, preservatives or solvents to assist drug penetration, and emollients in ointments, gels, and creams. Such topical formulations may also contain compatible conventional carriers, for example ethanol or oleyl alcohol for lotions. Such carriers may constitute from about 1% to about 98% by weight of the formulation; more usually, such carriers will constitute up to about 80% by weight of the formulation. Specific formulations for the topical delivery of aptamers are described in U.S. Pat. No. 6,841,539 and U.S. Publication No. 20050096287. The dosage delivered in a topical formulation is designed to accommodate the continuous delivery mode.

In one embodiment, a β-NGF aptamer is prepared with a carrier that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the β-NGF aptamer may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

In some cases, it may be especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of a β-NGF aptamer calculated to produce the desired therapeutic effect in association with the required pharmaceutical carrier. The specification for the dosage unit forms of the β-NGF aptamers described herein are dictated by and directly dependent on the unique characteristics of the particular β-NGF aptamer and the particular therapeutic effect to be achieved, and the limitations inherent in the art of compounding such an active agent for the treatment of individuals.

Pharmaceutical compositions comprising at least one β-NGF aptamer can include one or more pharmaceutical excipients. Examples of such excipients include, but are not limited to, binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel® PH101 and Avicel® PH102, silicified microcrystalline cellulose (Pro-Solv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In various embodiments, the formulations described herein are substantially pure. As used herein, "substantially pure" means the active ingredient (β-NGF aptamer) is the predominant species present (i.e., on a molar basis it is more abundant than any other individual species in the composition). In one embodiment, a substantially purified fraction is a composition wherein the active ingredient comprises at least about 50 percent (on a molar basis) of all macromolecular species present. Generally, a substantially pure composition will include more than about 80% of all macromolecular species present in the composition. In various embodiments, a substantially pure composition will include at least about 85%, at least about 90%, at least about 95%, or at least about 99% of all macromolecular species present in the composition. In various embodiments, the active ingredient is purified to essential homogeneity (contaminant species cannot be detected in the composition by conventional detection methods) wherein the composition consists essentially of a single macromolecular species.

Kits Comprising β-NGF Aptamer Compositions

The present disclosure provides kits comprising any of the β-NGF aptamers described herein. Such kits can comprise, for example, (1) at least one β-NGF aptamer; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus.

Methods of Treatment

The present disclosure provides methods of preventing or treating (e.g., alleviating one or more symptoms of) medical conditions through the use of a β-NGF aptamer. The methods comprise administering a therapeutically effective amount of a β-NGF aptamer to a patient in need thereof. The described aptamers can also be used for prophylactic therapy. In some embodiments the β-NGF aptamer is administered topically.

The β-NGF aptamer used in methods of treatment can be: (1) a novel β-NGF aptamer prepared by the methods described herein, or a pharmaceutically acceptable salt thereof, or a prodrug thereof.

The individual or patient can be any animal (domestic, livestock or wild), including, but not limited to, cats, dogs, horses, pigs and cattle, and preferably human patients. As used herein, the terms patient, individual, and subject may be used interchangeably.

As used herein, "treating" describes the management and care of a patient for the purpose of treating a disease, condition, or disorder and includes the administration of a β-NGF aptamer to prevent the onset of the symptoms or complications of a disease, condition or disorder; to alleviate symptoms or complications of the disease, condition, or disorder; or to eliminate the presence of the disease, condition or disorder in the patient. More specifically, "treating" includes reversing, attenuating, alleviating, minimizing, suppressing or halting at least one deleterious symptom or effect of a disease (disorder) state, disease progression, disease causative agent (e.g., bacteria or viruses), or other abnormal condition. Treatment is generally continued as long as symptoms and/or pathology ameliorate.

In various embodiments, the disclosed compositions (including topical formulations) and methods are used to treat dermatitis, which is often characterized as a superficial inflammation or rash of the skin characterized by redness, edema, oozing, crusting, scaling, and sometimes vesicles. Pruritis (itching) is common in dermatitis. Eczema is a term often used interchangeably with dermatitis. Examples of dermatitis or eczema include, for example, atopic dermatitis (also called infantile or flexural eczema), contact dermatitis (including allergic and irritant), xerotic eczema (also referred to as asteatotic eczema, craquele or craquelatum, winter itch, or pruritis hiemalis), exfoliative dermatitis, hand and foot dermatitis, neurodermatitis (e.g., lichen simplex chronicus), seborrheic dermatitis (cradle cap in infants, dandruff), discoid eczema (also referred to as nummular eczema, exudative eczema, microbial eczema), dyshydrosis, venous eczema (gravitationa eczema, stasis dermatitis, varicose eczema stasis dermatitis, dermatitis herpetiformis (Duhring's Disease), autoeczematization (also referred to as id reaction, autosensitization), cercarial dermatitis (e.g., swimmer's itch or duck itch), urushiol-induced contact dermatitis, which is also called toxicodendron dermatitis and rhus dermatitis (e.g., poison oak, poison ivy, sumac), solar dermatitis, and housewife eczema.

In one embodiment, the disclosed compounds or pharmaceutically acceptable salts thereof, or prodrugs, can be administered in combination with other treatments that improve or eradicate itching. Compositions including the disclosed β-NGF aptamers may contain, for example, more than one aptamer, e.g., an IgE, IL-6, and/or PAR2 aptamer and a β-NGF aptamer. In some examples, a β-NGF aptamer composition containing one or more aptamers is administered in combination with another useful anti-pruritic composition, such as, for example, an anti-histamine, an analgesic, an anticholinergics, a non-steroid anti-inflammation drug, a steroid, an anti-oxidant agent, a vitamin, a leukotriene modifier, an interleukin antagonist, a mast cell inhibitor, an anti-IgE antibody, a selective serotonin reuptake inhibitor, a 5-hydroxytryptamine receptor antagonist, an antibiotic, a calcineurin inhibitor, a histone deacetylase inhibitor, gabapentin or naloxone, in which active ingredients are present in free form or in the form of a pharmaceutically acceptable salt and, optionally, at least one pharmaceutically acceptable carrier, for systemic or topical use or administration simultaneously, separately, or sequentially, or the like. In general, the currently available dosage forms of the known therapeutic agents for use in such combinations will be suitable.

"Combination therapy" (or "co-therapy") includes the administration of a β-NGF aptamer composition and at least one second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present disclosure. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dose having a fixed ratio of each therapeutic agent or in multiple, single doses for each of the therapeutic agents.

The dosage regimen utilizing the β-NGF aptamers is selected in accordance with a variety of factors, including, for example, type, species, age, weight, sex and medical condition of the patient; the severity of the condition to be treated; the route of administration; the renal and hepatic function of the patient; and the particular β-NGF aptamer or salt thereof employed. An ordinarily skilled physician or veterinarian can readily determine and prescribe the effective amount of the composition required to prevent, counter or arrest the progress of the condition.

In general, the dosage, i.e., the therapeutically effective amount, ranges from about 1 µg to about 100 mg/kg body weight of the subject being treated, per day.

Efficacy

Figure 5:
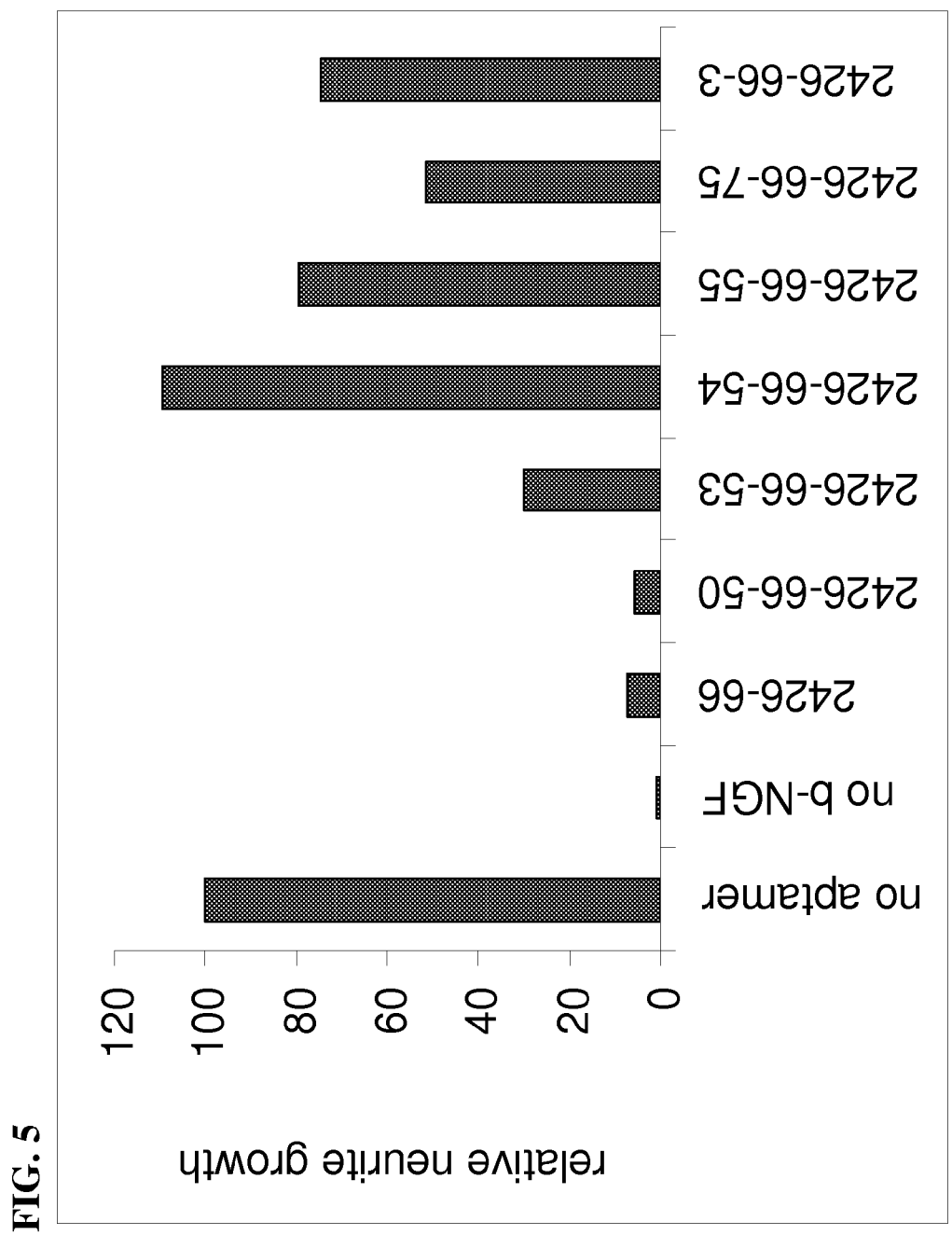
FIG. 5 illustrates graphically the ability of various aptamers to inhibit human β-NGF induced differentiation of PC12 cells as tested in the neurite growth assay described in Example 4.
Figure 7:
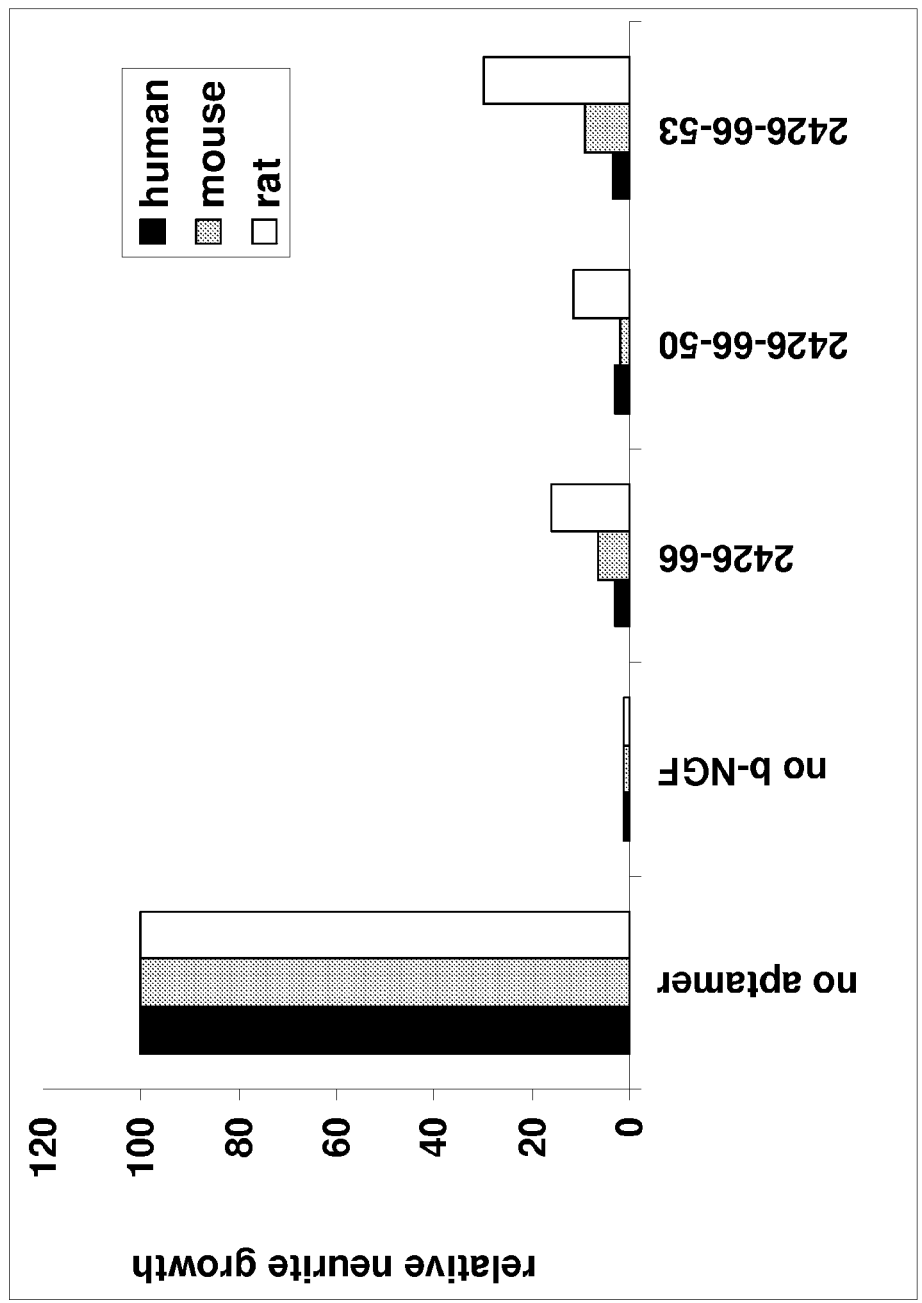
FIG. 7 illustrates graphically the inhibition of human β-NGF, mouse β-NGF and rat β-NGF mediated neurite growth by aptamer 2426-66 (SEQ ID NO: 1) and truncated variants 2426-66-50 (SEQ ID NO: 2) and 2426-66-53 (SEQ ID NO: 43). All three aptamers inhibited mouse β-NGF nearly as effectively as human β-NGF, and inhibited rat β-NGF to a lesser extent.
Figure 8:
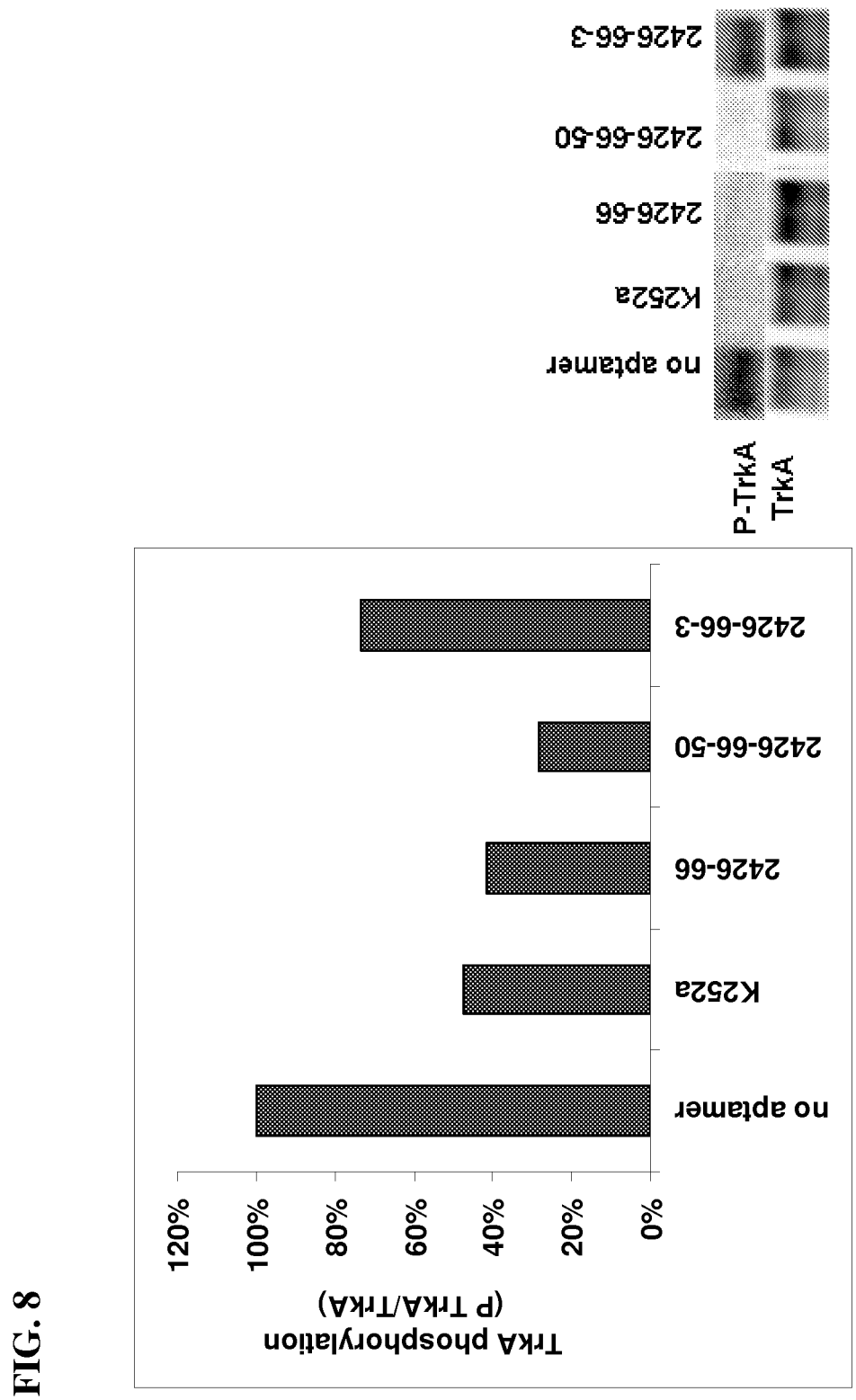
FIG. 8 illustrates graphically the results of a TrkA phosphorylation assay using aptamers 2426-66 (SEQ ID NO: 1) and truncated variants 2426-66-50 (SEQ ID NO: 2) and 2426-66-3 (SEQ ID NO: 5).
Figure 9:
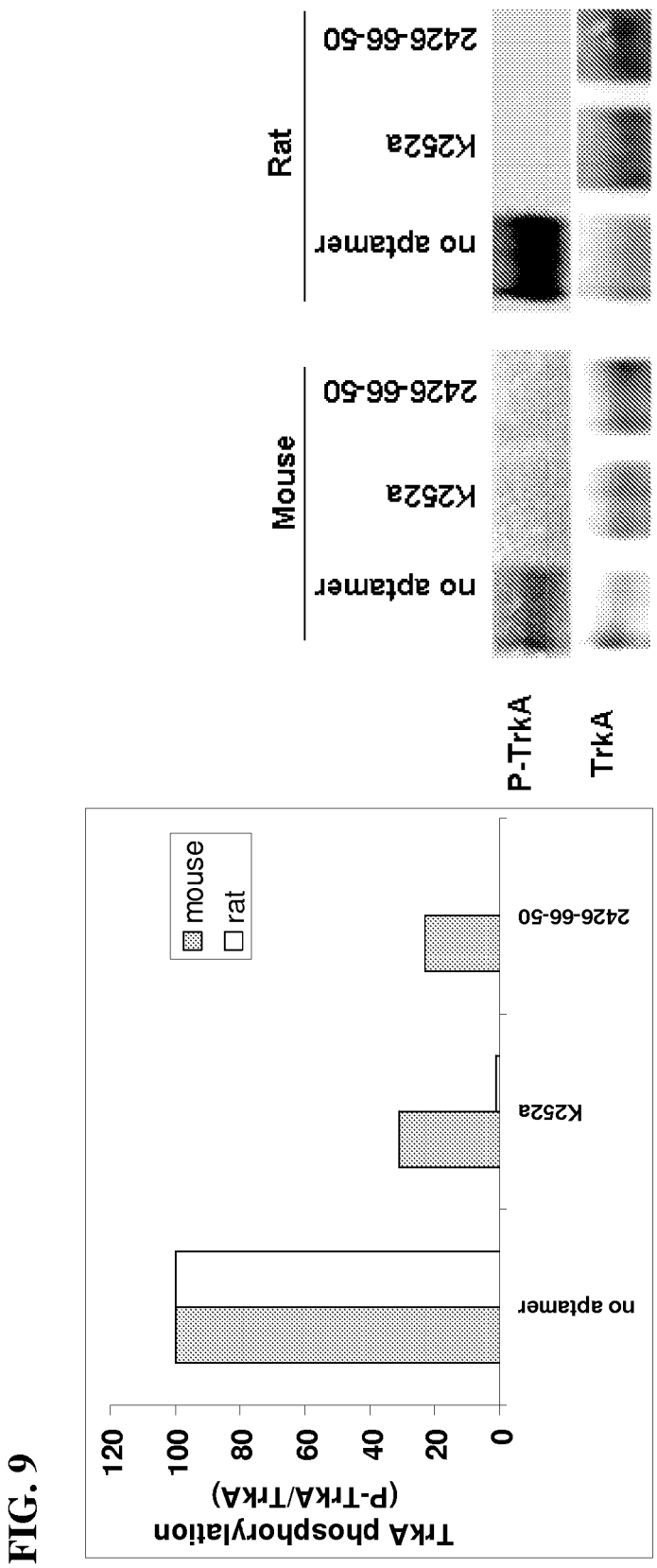
FIG. 9 illustrates graphically a TrkA phosphorylation assay for truncated aptamer 2426-66-50 (SEQ ID NO: 2) using mouse and rate β-NGF.

Example 4 illustrates the ability of various β-NGF aptamers and truncated variants thereof to inhibit human β-NGF mediated neurite growth (FIGS. 5-7) and to inhibit TrkA phosphorylation by β-NGF (FIGS. 8 and 9).

Figure 11:
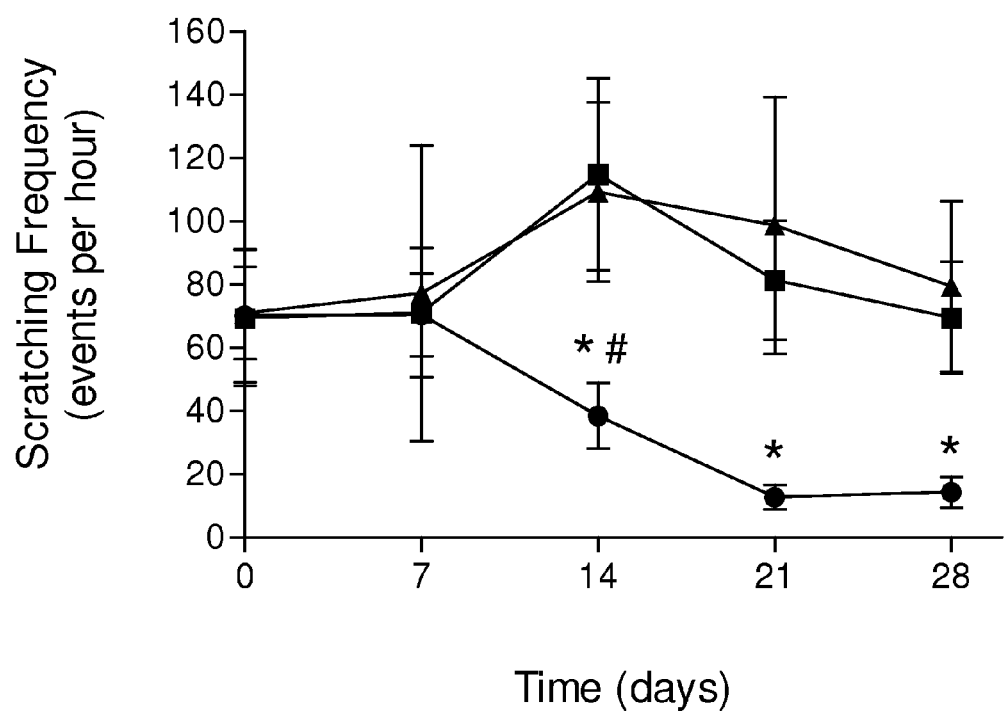
FIG. 11 illustrates graphically the reduction of scratching frequency over four weeks in diseased mice treated with aptamer 2426-66-50 (SEQ ID NO: 2) (●), but not in untreated mice (■) or mice treated with hydrophilic ointment (HO) (▲), as described in Example 5. Statistically significant differences ($p<0.05$) were observed between aptamer treatment and no treatment (*), or aptamer treatment and HO treatment (#), as determined by t-test.

Example 5 illustrates the efficacy of β-NGF aptamers in reducing scratching frequency and improving the clinical skin condition by administering aptamer 2426-66-50 (SEQ ID NO: 2) to diseased mice. With reference to FIG. 11, it can be seen that scratching frequency decreased steadily from day 14-28 in mice treated with aptamer 2426-66-50 (●), in contrast no change was observed in untreated mice (■) or mice treated with hydrophilic ointment (HO) (▲). Likewise, with reference to FIG. 12, it can be seen that clinical skin condition improved over 4 weeks in diseased mice treated with aptamer 2426-66-50 (SEQ ID NO: 2) (●), and, as with scratching frequency, there was no improvement in untreated mice (■) or mice treated with HO (▲).

EXAMPLES

The following examples are provided for illustrative purposes only and are not intended to limit the scope of the invention as defined by the appended claims. All examples described herein were carried out using standard techniques, which are well known and routine to those of skill in the art. Routine molecular biology techniques described in the following examples can be carried out as described in standard laboratory manuals, such as Sambrook et al., Molecular Cloning: A Laboratory Manual, 3rd. ed., Cold Spring Harbor Laboratory Press, Cold Spring Harbor, N.Y., (2001).

Example 1

Aptamer Selection and Sequences

A. Preparation of Candidate Mixtures

A candidate mixture of partially randomized ssDNA oligonucleotides was prepared by polymerase extension of a DNA primer annealed to a biotinylated ssDNA template as shown in Table 1. The candidate mixture contained a 40 nucleotide randomized cassette containing dATP, dGTP, dCTP and BndUTP (5-(N-benzylcarboxyamide-2'-deoxyuridine triphosphate).

4.8 nmol of Primer 1 (SEQ ID NO:165) possessing a unique chromophore, nitroazidoaniline (ANA, designated as X in the sequence) at the 5' terminus and 4 nmol of Template 1 (SEQ ID NO: 46) possessing two biotin residues (designated as B' in the sequence) and 40 randomized positions (A, C, G, or T) (designated as N in the sequence) were combined in 100 µL 1×KOD DNA Polymerase Buffer (Novagen), heated to 95° C. for 8 minutes, and cooled on ice. The 100 µL primer:template mixture was added to a 400 µL extension reaction containing 1×KOD DNA Polymerase Buffer, 0.125 U/µL KOD XL DNA Polymerase, and 0.5 mM each dATP, dCTP, dGTP, and BndUTP, and incubated at 70° C. for 30 minutes. Double-stranded product was captured via the template strand biotins by adding 1 mL streptavidin-coated magnetic beads (MagnaBind Streptavidin, Pierce, 5 mg/mL in 3 M NaCl containing 0.05% TWEEN-20) and incubating at 25° C. for 10 minutes with mixing. Beads were washed three times with 0.75 mL SB17T Buffer (40 mM HEPES, pH 7.5, 125 mM NaCl, 5 mM KCl, 5 mM $MgCl_2$, 0.05% TWEEN-20). The aptamer strand was eluted from the beads with 1.2 mL 20 mM NaOH, neutralized with 0.3 mL 80 mM HCl, and buffered with 15 µL 1 M HEPES, pH 7.5. The candidate mixtures was concentrated with a Centricon-30 to approximately 0.2 mL, and quantified by UV absorbance spectroscopy.

TABLE 1

Sequences of SELEX Template and Primers

| Oligonucleotide Designation | Sequence (5'→ 3') | SEQ ID NO: |
|---|---|---|
| Template 1 | AB'AB'TTTTTTTTGGTCTTGTTTCTTCTC TGTG-(N)$_{40}$-CAGGCAGACGGTCACTC | 46 |
| Primer 1 | XGGTCTTGTTTCTTCTCTGTG | 165 |
| Primer 2 | ATATATATGAGTGACCGTCTGCCTG | 47 |
| Primer 3 | AB'AB'TTTTTTTTGGTCTTGTTTCTTCTC TGTG | 48 |
| Primer 4 | TTTTTTTTGGTCTTGTTTCTTCTCTGTG | 169 |

B. Preparation of Target Protein

Untagged human β-NGF (R&D Systems) was biotinylated by covalent coupling of NHS-PEO4-biotin (Pierce) to lysines residues. Protein (300 pmol in 50 µL) was exchanged into SB17T with a Sephadex G-25 microspin column NHS-PEO4-biotin was added to 1.5 mM and the reaction was incubated at 4° C. for 16 hours. Unreacted NHS-PEO4-biotin was removed with a Sephadex G-25 microspin column.

C. Immobilization of Target Protein

Target protein was immobilized on MyOne-SA paramagnetic beads (MyOne SA, Invitrogen, or hereinafter referred to as SA beads) for Round 1 of SELEX. β-NGF was diluted to 0.2 mg/mL in 0.5 mL SB17T and added to 0.5 mL SA beads (pre-washed twice with 20 mM NaOH and once with SB17T). The mixture was rotated for 30 minutes at 25° C. and stored at 4° C. until use.

D. Aptamer Selection with Slow Off-Rate Enrichment Process and Photocrosslinking Selections were performed with the candidate mixture, comparing binding between samples with target protein (signal S) and samples without target protein (background B). The first three rounds were performed with selection for affinity (no photocrosslinking); the second and third included slow off-rate enrichment process. Rounds four through nine included both slow off-rate enrichment process and photocrosslinking.

For each sample, a 90 μL DNA mixture was prepared in SB17T with 10-20 pmoles candidate mixture (56 pmoles in the first round) and 56 pmoles reverse primer. Samples were heated to 95° C. for 3 minutes and cooled to 37° C. at a rate of 0.1 C/second. Samples were combined with 10 μL protein competitor mixture (0.1% HSA, 10 μM casein, and 10 μM prothrombin in SB17T), added to 0.5 mg SA beads and incubated at 37° C. for 5 minutes with mixing. Beads were removed by magnetic separation.

Binding reactions were performed by adding 10 μL target protein (0.5 μM in SB17T) or SB17T to 40 μL DNA mixtures and incubating at 37° C. for 30 min. The slow-off rate enrichment process was employed in three different ways. In rounds two and three, samples were diluted 20-fold by adding 950 μL SB17T (preheated to 37° C.), and incubated at 37° C. for 15 minutes prior to capturing complexes. In rounds four and five, samples were diluted 20-fold by adding 950 μL SB17T (preheated to 37° C.), and incubated at 37° C. for 30 minutes prior to crosslinking. In rounds six and seven, samples were diluted 20-fold by adding 950 μL SB17T (preheated to 37° C.). 50 μL of each diluted sample was diluted again by transferring to 950 μL SB17T containing 10 mM dextran sulfate (5 kDa) (preheated to 37° C.) to give an overall 400-fold dilution, and incubated at 37° C. for 60 minutes prior to crosslinking. In rounds eight and nine, samples were diluted 20-fold by adding 950 μL SB17T (preheated to 37° C.), and 50 μL of each sample was diluted again by transferring to 950 μL SB17T (preheated to 37° C.) to give 400-fold dilution. Finally, 50 μL of each 400-fold diluted sample was diluted again by transferring to 950 μL SB17T containing 10 mM dextran sulfate (5 kDa) (preheated to 37° C.) to give an overall 8000-fold dilution, and incubated at 37° C. for 60 minutes prior to crosslinking. When photocrosslinking was employed, the 1 mL binding reactions after the slow off-rate enrichment process were irradiated from above with an array of 470 nm LEDs for 60 seconds prior to complex capture.

Complexes were captured on SA beads via protein biotins by adding 0.25 mg MyOne-SA beads (Invitrogen) and incubating at 25° C. for 15 minutes with mixing. Free DNA was removed by washing the beads five times with SB17T. Unless indicated, all washes were performed by resuspending the beads in 100 μL wash solution, mixing for 30 seconds at 25° C., separating the beads with a magnet, and removing the wash solution. The aptamer strand was eluted from the beads by adding 85 μL 20 mM NaOH, and incubating at 37° C. for 1 minute with mixing. 80 μL aptamer eluate was transferred to a new tube after magnetic separation, neutralized with 20 μL 80 mM HCl, and buffered with 1 μL 0.5 M Tris-HCl, pH 7.5.

When photo-selection was employed complexes were captured as above, and non-crosslinked DNA was removed by washing the beads once with 4 M guanidine-HCl containing 0.05% TWEEN-20 at 50° C. for 10 minutes, once with 20 mM NaOH at 25° C. for 2 minutes, twice with SB17T, and once with 16 mM NaCl. Crosslinked DNA was not removed from the bead surface for the amplification steps.

E. Aptamer Amplification and Purification

Selected aptamer DNA was amplified and quantified by QPCR. 48 μL DNA was added to 12 μL QPCR Mix (5×KOD DNA Polymerase Buffer, 25 mM $MgCl_2$, 10 μM forward PCR primer (Primer 2, SEQ ID NO: 47), 10 μM biotinylated reverse PCR primer (Primer 3, SEQ ID NO: 48), 5×SYBR Green 1, 0.125 U/μL KOD XL DNA Polymerase, and 1 mM each dATP, dCTP, dGTP, and dTTP) and thermal cycled in a Bio-Rad MyIQ QPCR instrument with the following protocol: 1 cycle of 99.9° C., 15 sec, 55° C., 10 sec, 68° C., 30 min, 30 cycles of 99.9° C., 15 seconds, 72° C., 1 minute. Quantification was done with the instrument software and the number of copies of DNA selected, with and without target protein, was compared to determine signal/background ratios.

When photo-selection was employed, a cDNA copy of the selected DNA was prepared by primer extension on the bead surface. Washed beads were resuspended in 20 μL cDNA extension mix (Primer Extension Buffer containing 5 μM non-biotinylated reverse PCR primer (Primer 4, SEQ ID NO: 169), 0.5 mM each dATP, dCTP, dGTP, and dTTP, and 0.125 U/μL KOD XL DNA Polymerase) and incubated at 68° C. for 30 minutes with mixing. The beads were washed 3 times with SB17T, and the cDNA strand was eluted from the beads by adding 85 μL 20 mM NaOH, and incubating at 37° C. for 1 minute with mixing. 80 μL aptamer eluate was transferred to a new tube after magnetic separation, neutralized with 20 μL 80 mM HCl, and buffered with 1 μL 0.5 M Tris-HCl, pH 7.5. The cDNA was amplified and quantified by QPCR as above with 30 cycles of 99.9° C., 15 seconds, 72° C., 1 minute.

Following amplification, the PCR product was captured on SA beads via the biotinylated antisense strand. 1.25 mL SA beads (10 mg/mL) were washed twice with 0.5 mL 20 mM NaOH, once with 0.5 mL SB17T, resuspended in 1.25 mL 3 M NaCl+0.05% Tween, and stored at 4° C. 25 μL SA beads (10 mg/mL in 3 M NaClT) were added to 50 μL double-stranded QPCR products and incubated at 25° C. for 5 minutes with mixing. The beads were washed once with SB17T, and the "sense" strand was eluted from the beads by adding 200 μL 20 mM NaOH, and incubating at 37° C. for 1 minute with mixing. The eluted strand was discarded and the beads were washed 3 times with SB17T and once with 16 mM NaCl.

Aptamer sense strand was prepared with the ANA chromophore by primer extension from the immobilized antisense strand. The beads were resuspended in 20 μL primer extension reaction mixture (1× Primer Extension Buffer, 1.5 mM $MgCl_2$, 5 μM forward primer with 5' ANA chromophore (Primer 1, SEQ ID NO: 165), 0.5 mM each dATP, dCTP, dGTP, and BndUTP, and 0.125 U/μL KOD XL DNA Polymerase) and incubated at 68° C. for 30 minutes with mixing. The beads were washed 3 times with SB17T, and the aptamer strand was eluted from the beads by adding 85 μL 20 mM NaOH, and incubating at 37° C. for 1 minute with mixing. 80 μL aptamer eluate was transferred to a new tube after magnetic separation, neutralized with 20 μL 80 mM HCl, and buffered with 5 μL 0.1 M HEPES, pH 7.5.

F. Selection Stringency and Feedback

The relative target protein concentration of the selection step was lowered each round in response to the S/B ratio as follows, where signal S and background B are defined in Section D above:

If $S/B < 10$, $[P]_{(i+1)} = [P]_i$

If $10 \leq S/B < 100$, $[P]_{(i+1)} = [P]_i / 3.2$

If $S/B \geq 100$, $[P]_{(i+1)} = [P]_i / 10$ where [P]=protein concentration and i=current round number.

After each selection round, the convergence state of the enriched DNA mixture was determined. 10 μL double-stranded QPCR product was diluted to 200 μL with 4 mM $MgCl_2$ containing 1×SYBR Green I. Samples were overlaid with 75 μL of silicon oil and analyzed for convergence using a $C_0t$ analysis which measures the hybridization time for complex mixtures of double stranded oligonucleotides. Samples were thermal cycled with the following protocol: 3 cycles of 98° C., 1 minute, 85° C., 1 minute; 1 cycle of 93° C., 1 minute, 85° C., 15 minutes. During the 15 minutes at 85° C., fluorescent images were measured at 5-second intervals. The fluorescence intensity was plotted as a function of log (time), and an increased rate of hybridization with each SELEX round was observed, indicating sequence convergence.

G. Clone Screening Process & Aptamer Identification

The converged pool after nine rounds of SELEX was cloned and sequenced. Selected DNA was PCR amplified with non-biotinylated SELEX primers to create AGCT DNA, purified using a QIAquick 96 PCR Purification Kit (Cat#28181), and purified inserts were cloned using Stratagene PCR-Script Cloning Kit (Cat#211189) as per manufacturer's protocol. The ligated SELEX pools were sent to a sequencing vender (Cogenics, Houston, Tex.) for transformation, array into 96-well plates, DNA prep and sequencing. Sequences for ~42 clones were obtained and analyzed for convergence using custom software that determines sequence counts/copy number and identifies common convergence patterns using a local-alignment algorithm. Sequences with highest representation/copy number in the pool and sequences that were converged to common binding motifs were chosen for downstream screening. Six sequences were chosen for further analysis and were prepared enzymatically using plasmid DNA obtained from Cogenics as template for PCR amplification.

H. Measurement of Equilibrium Binding Constant ($K_d$)

The equilibrium binding constants of the 6 chosen sequences were measured in an affinity assay. Radiolabeled DNA was heated for 3 minutes at 95° C. in SB17T-0.002 (SB17T with TWEEN-20 reduced to 0.002%) and slowly cooled to 37° C. Complexes were formed by mixing a low concentration of radiolabeled DNA (~$1\times10^{-11}$ M) with a range of concentrations of target protein ($1\times10^{-7}$ M to $1\times10^{-12}$ M) in SB17T-0.002, and incubating at 37° C. for 30 minutes. A portion of each reaction was transferred to a nylon membrane and dried to determine total counts in each reaction. Complexes were captured on ZORBAX resin (Agilent), passed through a MultiScreen HV Plate (Millipore) under vacuum, and washed with 200 μL SB17T-0.002 Buffer to separate protein-bound complexes from unbound DNA. The nylon membrane and MultiScreen HV Plate were phosphorimaged and the amount of radioactivity in each sample quantified using a FUJI FLA-3000. The fraction of captured DNA was plotted as a function of protein concentration ($P_t$) and equilibrium binding constants ($K_d$) were determined using $y=(max-min)(P_t)/(K_d+P_t)+min$. Clone 2426-66 (SEQ ID NO: 1, listed in Table 3), a 76-mer, with a $K_d=5\times10^{-9}$ M was selected as the lead clone for further characterization, see FIG. 1.

I. Deep Sequencing of SELEX Pool

To evaluate more completely the sequences within the 2426-66 aptamer family, the enriched pool was sequenced using 454 pyrosequencing technology. The pool DNA was amplified with 454 primers as described above and the PCR product was purified and normalized using a Sequal normalization plate (Invitrogen, Cat# A10510-01). The eluate was run on a gel to confirm the size and purity of each amplicon. The purified PCR product was sequenced at the 454 pyrosequencing facility at the University of Colorado Health Science Center in Aurora Colo.

The 454 sequences were aligned with 2426-66 by CLUSTAL analysis. From the total of 1165 multi-copy sequences, 165 sequences had similar pattern to 2426-66. Based on 5' sequence commonalities in these sequences, they were aligned into three groups. The middle region of sequence was conserved in all three groups. For all the sequences, the percentage identity at each position with 2426-66 was calculated as listed in FIG. 2B. Table 2 lists a number of sequences representative of the 2426-66 aptamer family of sequences, wherein Z' represents a BndU.

TABLE 2

Sequences Representative of the 2426-66 Aptamer*

| Aptamer Designation | Sequence (5'→3') | SEQ ID NO: |
|---|---|---|
| 2426-87 | CAGCGGGACACAZ'GAGGACZ'Z'GGGGZ'Z'Z'GGCCGZ'Z'GZ'GG | 49 |
| 2426-88 | CAGCGGGACACAZ'GAGGACZ'Z'GGGGZ'Z'Z'AGCCGZ'Z'GZ'GC | 50 |
| 2426-1373 | GCAGCGGGACACAZ'GAGGACAZ'GGGGZ'Z'Z'AGCGZ'Z'GZ'GG | 51 |
| 2426-1621 | GCAGCGGGACACAZ'GAGGACCZ'GGGGZ'Z'Z'AGCCGZ'Z'GZ'GG | 52 |
| 2426-1634 | GCGGCGGGACACAZ'GAGGACZ'Z'GGGGZ'Z'Z'AGCCGZ'Z'GZ'GG | 53 |
| 2426-1627 | GCAGCGGGACACAZ'Z'AGGACZ'Z'GGGGZ'Z'Z'AGCCGZ'Z'GZ'GG | 54 |
| 2426-1372 | GCAGCGGAACACAZ'GAGGACZ'Z'GGGGZ'Z'Z'AGCCGZ'Z'GZ'GG | 55 |
| 2426-1387 | GCAGCGGZ'ACACAZ'GAGGACZ'Z'GGGGZ'Z'Z'AGCCGZ'Z'GZ'GG | 56 |
| 2426-1527 | CAGCGGGACACAZ'GAGGACZ'Z'GGGZ'Z'Z'AGCCGZ'Z'GZ'GGCA | 57 |
| 2426-1753 | Z'CAGCGGGACACAZ'GAGGACZ'Z'GGGGZ'Z'Z'AGCCGZ'Z'GZ'GG | 58 |
| 2426-1003 | GCAGCGGGACACAZ'GAGGACZ'Z'GGGGZ'Z'Z'AGCCGZ'Z'GZ'GG | 59 |
| 2426-1626 | GCAGCGGGACACAZ'GAGGACZ'Z'GGGGZ'Z'Z'AGZ'CGZ'Z'GZ'GG | 60 |
| 2426-1380 | GCAGCGGGACACAZ'GAGGACZ'Z'GGGGZ'Z'Z'AGCCAZ'Z'GZ'GG | 61 |
| 2426-1625 | GCAGCGGGACACAZ'GAGGACZ'Z'GGGGZ'Z'Z'AGCCZ'Z'Z'GZ'GG | 62 |
| 2426-1388 | GCAGCGZ'GACAZ'AZ'GAGGACZ'Z'GGGGZ'Z'Z'AGCCGZ'Z'GZ'GG | 63 |
| 2426-1381 | GCAGCGGGACACAZ'GAGGACZ'Z'GGGGZ'Z'Z'AGCCGZ' GZ'AG | 64 |
| 2426-1699 | GZ'AGCGGGACACAZ'GAGGACZ'Z'GGGGZ'Z'Z'AACCGZ'Z'GZ'GG | 65 |
| 2426-1702 | GZ'AGCGGGACACAZ'GGGGACZ'Z'GGGGZ'Z'Z'AACCGZ'Z'GZ'GG | 66 |
| 2426-1265 | GAAGCGGGACACAZ'GAGGACZ'Z'GGGGZ'Z'Z'AACCGZ'Z'GZ'GG | 67 |

TABLE 2-continued

Sequences Representative of the 2426-66 Aptamer*

| Aptamer Designation | Sequence (5'→3') | SEQ ID NO: |
|---|---|---|
| 2426-1374 | GCAGCGGGACACAZ'GAGGACZ'Z'GAGGZ'Z'AACCGZ'Z'GZ'GG | 68 |
| 2426-1377 | GCAGCGGGACACAZ'GAGGACZ'Z'GGGGZ'Z'AACCGZ'Z'GZ'GG | 69 |
| 2426-1384 | GCAGCGGGACACAZ'GAGZ'ACZ'Z'GGGGZ'Z'AACCGZ'Z'GZ'GGC | 70 |
| 2426-1622 | GCAGCGGGACACAZ'GAGGACZ'Z'GGGGZ'Z'AACCGZ'Z'GZ'GGC | 71 |
| 2426-1378 | GCAGCGGGACACAZ'GAGGACZ'Z'GGGGZ'Z'AACCGZ'Z'GZ'GZ' | 72 |
| 2426-1266 | GAAGCGGGACACAZ'GAGGACZ'Z'GGGGZ'Z'AGCCGZ'Z'GZ'Z'G | 73 |
| 2426-1537 | GAAGCGGGACACAZ'GAGGACZ'Z'GGGGZ'Z'AGCCGZ'Z'GZ'GG | 74 |
| 2426-1355 | GCAACGGGACACAZ'GAZ'GACZ'Z'GGGGZ'Z'AGCCGZ'Z'GZ'GG | 75 |
| 2426-1385 | GCAGCGGGACACAZ'GAZ'GACZ'Z'Z'GGGZ'Z'AGCCGZ'Z'AZ'GG | 76 |
| 2426-1701 | GZ'AGCGGGACACAZ'GAZ'GACZ'Z'GGGGZ'Z'AGCCGZ'Z'GZ'GG | 77 |
| 2426-1458 | GZ'AGCGGGACACAZ'GAGGACZ'Z'GGGGGZ'Z'AGCCGZ'Z'GCGG | 78 |
| 2426-1700 | GZ'AGCGGGACACAZ'GAGGACZ'Z'GGGGZ'Z'AGCCGZ'Z'GZ'GG | 79 |
| 2426-1386 | GCAGCGGGGCACAZ'GAGGACZ'Z'GGGGZ'Z'AGCCGZ'Z'GZ'GG | 80 |
| 2426-1623 | GCAGCGGGACACAZ'GAGGACZ'Z'GGGGZ'Z'AGCAGZ'Z'AZ'GG | 81 |
| 2426-1392 | GCAGZ'GGGACACAZ'GAGGACZ'Z'GGGGZ'Z'AGCCGZ'Z'AZ'GC | 82 |
| 2426-1624 | GCAGCGGGACACAZ'GAGGACZ'Z'GGGGZ'Z'AGCCGZ'Z'AZ'GC | 83 |
| 2426-1383 | GCAGCGGGACACAZ'GAGGACZ'Z'GGGGZ'Z'AGCCGZ'Z'GZ'GC | 84 |
| 2426-1382 | GCAGCGGGACACAZ'GAGGACZ'Z'GGGGZ'Z'AGCCGZ'Z'GZ'GA | 85 |
| 2426-1619 | GCAGCCGGACACAZ'GAGZ'ACZ'Z'GGGGZ'Z'AGCCGZ'Z'GZ'GG | 86 |
| 2426-1389 | GCAGCZ'GGACACACGAGGACZ'Z'GGGGZ'Z'AGCZ'GZ'Z'GZ'GG | 87 |
| 2426-1371 | GCAGCAGGACACAZ'GAGGACZ'Z'GGGGZ'Z'AGCCGZ'Z'GZ'GG | 88 |
| 2426-1391 | GCAGZ'AGGACACAZ'GAGGACZ'Z'GGGGZ'Z'AGCCGZ'Z'GZ'GG | 89 |
| 2426-1618 | GCAGAGGGACACAZ'GAGGACZ'Z'GGGGZ'Z'AGCCGZ'Z'GZ'GG | 90 |
| 2426-1629 | GCAGZ'GGGACACAZ'GAGGACZ'Z'GGGGZ'Z'AGCCGZ'Z'GZ'GG | 91 |
| 2426-1393 | GCAGZ'GGGAZ'ACAZ'GAGGACGZ'Z'GGGGZ'Z'Z'AGCCGZ'Z'GZ'G | 92 |
| 2426-1457 | GZ'AGCGGGACACAZ'GAGGACGZ'Z'GGGGZ'Z'Z'AGCCGZ'Z'GZ'G | 93 |
| 2426-1642 | GGAGCGGGGCACAZ'GAGGACZ'Z'GGGGGZ'Z'Z'AGCCGZ'Z'GZ'G | 94 |
| 9999-1044 | GCAGCGGGACACAZ'GAGGACZ'Z'GGGGGZ'Z'Z'AGCCGZ'Z'GZ'G | 95 |
| 2426-1628 | GCAGCGGGACACZ'AZ'GAGGACZ'Z'GGGGZ'Z'Z'AGGCCGZ'Z'GZ' | 96 |
| 2426-1376 | GCAGCGGGACACAZ'GAGGACZ'Z'GGGGZ'Z'Z'AACCGZ'Z' | 97 |
| 2426-1379 | GCAGCGGGACACAZ'GAGGACZ'Z'GGGGZ'Z'Z'AG | 98 |
| 2426-1375 | GCAGCGGGACACAZ'GAGGACZ'Z'GGGGGZ'Z'Z'AGC | 99 |
| 2426-1390 | GCAGCZ'GGACACAZ'GAZ'GZ'ACGZ'Z'GGGGZ'Z'Z'AGCC | 100 |
| 2426-1390 | GCAGCZ'GGACACAZ'GAZ'GZ'ACGZ'Z'GGGGZ'Z'Z'AGCC | 101 |
| 2426-1402 | GGAACZ'AGCGZ'GGAZ'GGGGCZ'Z'GGGGZ'Z'Z'AGCCGZ'Z'AZ'GC | 102 |
| 2426-1531 | GAACZ'AGCGZ'GGAZ'GGGGGCZ'Z'GGGGZ'Z'Z'AGCCGZ'Z'AZ'GC | 103 |
| 2426-1401 | GGAACZ'AGCGZ'GAZ'GGGGGCZ'Z'GGGGZ'Z'Z'AGCCGZ'Z'AZ'GC | 104 |
| 2426-1755 | Z'GGAACZ'AGCGZ'GGAZ'GGGGGCZ'Z'GGGZ'Z'Z'AGCCG Z'Z'AZ'G | 105 |
| 2426-1404 | GGAACZ'AGCGZ'GGAZ'GGGGGCZ'Z'GGGGZ'Z'Z'AGCCAZ'Z'AZ'G | 106 |
| 2426-1009 | GGAACZ'AGCGZ'GGAZ'GGGGGCZ'Z'GGGGZ'Z'Z'AGCCGZ'Z'AZ'G | 107 |
| 2426-1403 | GGAACZ'AGCGZ'GGAZ'GGGGGCZ'Z'GGAGZ'Z'Z'AGCCGZ'Z'AZ'G | 108 |
| 2426-1637 | GGAACZ'AGCGZ'GGAZ'GGGGGCZ'Z'GGGGZ'Z'Z'AACCGZ'Z'AZ'G | 109 |
| 2426-1529 | GAAACZ'AGCGZ'GGAZ'GGGGGCZ'Z'GGGGZ'Z'Z'AGCCGZ'Z'AZ'G | 110 |
| 2426-1638 | GGAACZ'AGCGZ'GGAZ'GGGGGCZ'Z'GGGGZ'Z'Z'AGCCGZ'Z'GZ'G | 111 |
| 2426-1643 | GGAGCZ'AGCGZ'GGAZ'GGGGACZ'Z'GGGGZ'Z'Z'AGCCGZ'Z'GZ'G | 112 |
| 2426-1636 | GGAACZ'AGCACGGAZ'GGGGGCZ'Z'GGGGZ'Z'Z'AGCCGZ'Z'AZ'G | 113 |
| 2426-1405 | GGAACZ'AGCGZ'GGAZ'GGGGGCZ'Z'GGGGZ'Z'Z'AZ'CCGZ'Z'AZ'A | 114 |
| 2426-1406 | GGAACZ'AGCGZ'GGAZ'GGGGGCZ'Z'GGGZ'Z'AGZ' | 115 |
| 2426-1364 | GCAGAAZ'GCGGZ'AZ'AZ'GAGGACZ'Z'GGAGZ'Z'Z'AGCCGZ'Z'GZ' | 116 |

TABLE 2-continued

Sequences Representative of the 2426-66 Aptamer*

| Aptamer Designation | Sequence (5'→3') | SEQ ID NO: |
|---|---|---|
| 2426-1365 | GCAGAAZ'GCGGZ'AZ'AZ'GAGGACZ'Z'GGG GZ'Z'Z'AGCCGZ'Z'GZ' | 117 |
| 2426-1366 | GCAGAAZ'GCGGZ'AZ'AZ'GGGGACZ'Z'GGG GZ'Z'Z'GGCCGZ'Z'GZ' | 118 |
| 2426-1617 | GCAGAAZ'GCGGZ'AZ'AZ'GGGGGCZ'Z'GGG GZ'Z'Z'AZ'CCGZ' Z'GZ' | 119 |
| 2426-1367 | GCAGAAZ'GCGGZ'AZ'AZ'GGGGGCZ'Z'GGG GZ'Z'Z'AGCCAZ'Z'GZ' | 120 |
| 2426-1067 | GCAGAAZ'GAGGZ'AZ'AZ'GAGGACZ'Z'GGG GZ'Z'Z'AGCCGZ'Z'GZ' | 121 |
| 2426-1369 | GCAGAAZ'GCGGZ'AZ'AZ'GGGGGCZ'Z'GGG GZ'Z'Z'AZ'CCGZ'Z'AZ' | 122 |
| 2426-1368 | GCAGAAZ'GCGGZ'AZ'AZ'GGGGGCZ'Z'GGG GZ'Z'Z'AGCCGZ'Z'AZ' | 123 |
| 2426-1370 | GCAGAAZ'GCGGZ'AZ'AZ'GGGGGCZ'Z'Z'GG GZ'Z'Z'AGCCGZ'Z'AZ' | 124 |
| 2426-1616 | GCAGAAZ'GCGGZ'AZ'AZ'GGGGACZ'Z'GGG GGZ'Z'Z'AGCCGZ'Z'G | 125 |
| 2426-1363 | GCAGAAZ'GCGGZ'AZ'AGZ'GGGGGCZ'Z'GG GGZ'Z'Z'AGCCGZ'Z'A | 126 |
| 2426-1519 | Z'GCAGAAZ'GCGGZ'AZ'AZ'GGGGGCZ'Z'GG GGZ'Z'Z'AZ'CCG | 127 |
| 2426-1156 | GZ'GZ'CACZ'Z'GZ'GGGGAGZ'Z'GGGGZ'Z'GA Z'CCGZ'Z'GZ'CCGCC | 128 |
| 2426-1743 | GZ'GZ'CACZ'Z'GZ'GGGGAGZ'Z'GGGGZ'Z'GA Z'CCGZ'Z'GZ'CGCC | 129 |
| 2426-1514 | GZ'GZ'CACZ'Z'GZ'GGGGAGZ'Z'GGGGZ'Z'GA Z'CCGZ'Z'GZ'Z'CGZ' | 130 |
| 2426-1513 | GZ'GZ'CACZ'CGZ'GGGGAGZ'Z'GGGGZ'Z'GA Z'CCGZ'Z'GZ'Z'CGCZ' | 131 |
| 2426-1742 | GZ'GZ'CACZ'Z'GZ'GGGGAGZ'Z'GGGGZ'Z'GA Z'CCAAZ'GZ'Z'CGCZ' | 132 |
| 2426-1744 | GZ'GZ'CACZ'Z'GZ'GGGGAGZ'Z'GGGGZ'Z'GA Z'CCGZ'Z'GZ'Z'Z'CGC | 133 |
| 2426-1157 | GZ'GZ'CACZ'Z'GZ'GGGGAGZ'Z'GGGZ'Z'G Z'AZ'CCGZ'Z'CGZ'Z'Z'C | 134 |
| 2426-1094 | GGCGACGCGCACAGZ'GGGGZ'AGZ'Z'GGG GZ'Z'Z'AACCGZ'Z'GZ' | 135 |
| 2426-1417 | GGCGACGCGCGCAZ'AGGGZ'AGZ'Z'GGGG Z'Z'Z'AACCGZ'Z'GZ'C | 136 |
| 2426-63 | GCGACGCGCACAZ'GGGGZ'AGZ'Z'GGGGZ' Z'Z'AACGGZ'Z'GZ'CG | 137 |
| 2426-1038 | GACCAACAZ'GAGGACZ'Z'GGGGZ'Z'Z'AGC CGZ'Z'GZ'GGCACAG | 138 |
| 2426-1571 | GACCAACAZ'GAGGACZ'Z'GGGGZ'Z'Z'AGC CGZ'Z'GZ'GCACAG | 139 |
| 2426-1100 | GGGAAGCGAZ'AZ'GAGGACZ'Z'GGGG Z'Z'Z'AGCCGZ'Z'GZ'GGCA | 140 |
| 2426-1419 | GGGAAGCGAZ'AZ'GAGGAG Z'Z'GGGGZ'Z'Z'AZ'CCGZ'Z'GZ'CAAC | 141 |
| 2426-1089 | GGAGZ'AGGGAAAAZ'GGGGAGZ'Z'GGGGZ' Z'Z'AZ'CCGZ'Z'GZ'CA | 142 |
| 2426-1064 | GAZ'Z'GCZ'GGA GGA Z'GG GGAGZ'GGGG G Z'Z'Z'AZ' CCGZ'Z' GZ'CA | 143 |
| 2426-1352 | GAZ'Z'GCZ'GGAGGAZ'GGGGAGZ'Z'GGGGZ' Z'Z'AZ'CCGZ'Z'GZ'CA | 144 |
| 2426-1198 | GAZ'Z'GCZ'GGAGGAZ'GAGGACZ'Z'GGGGZ' Z'Z'AGCCGZ'Z'GZ'GG | 145 |
| 2426-1073 | GCCGGGGCCGCZ'AZ'GAGGACAZ'GGGGZ'Z' Z'AGCCGZ'Z'GZ'GG | 146 |
| 2426-1068 | GCAGAAZ'GCGAZ'AZ'AZ'GGGGGCZ'Z'GGG GZ'Z'Z'AGCCGZ'Z'AZ' | 147 |
| 2426-1231 | GGZ'GGCACACZ'GGZ'GGGGGGCZ'Z'GGGG Z'Z'GAGCCGZ'Z'AZ'G | 148 |

*Only the 40N region is shown

Based on this, as noted above, the consensus sequence for binding to β-NGF was determined to be the following sequence:

(SEQ ID NO: 3)
BAZGRGGRSZZGGGGZZZADCCGZZRZG wherein B, Z, R, and S are as defined above. While the consensus sequence is 28 nucleotides in length, a number of the sequences listed in Table 2 had single-base insertions in this consensus. FIG. 2B indicates approximately 91 percent of the sequences had a deletion at position 12, but approximately 7 percent of the sequences had a G or Z at this position, and approximately 95 percent had a deletion at position 19, but approximately 3 percent had a G at this position. This observation suggests insertions in the β-NGF consensus sequence (SEQ ID NO: 3) are tolerated at some positions and these insertions will not inactivate the β-NGF aptamer.

Example 2

Sequence Truncation Studies

β-NGF aptamer 2426-66 (SEQ ID NO: 1) is 76 nucleotides in length with a $K_d=5\times10^{-9}$ M. For most efficient chemical synthesis, it is important to identify the minimal high-affinity aptamer sequence and truncate the aptamer to the smallest size possible. Other advantages are increased tissue penetration and stability against nuclease activity in vivo.

In order to identify the minimal region of aptamer 2426-66 (SEQ ID NO: 1) that retains binding affinity, a series of truncated variants were synthesized representing all possible contiguous 50 nucleotide long sequences present in 2426-66. Sequences of the variants are listed in Table 3, wherein Z' represents BndU and T represents dT. The variants were tested for affinity to β-NGF in the affinity binding assay as described above.

TABLE 3

Sequences of Aptamer 2426-66 and Truncated Variants

| Aptamer Designation | Sequence (5'→ 3') | SEQ ID NO: |
|---|---|---|
| 2426-66 (76-mer) | GAGTGACCGTCTGCCTGCAGCGGGACACAZ'GAGGACZ'Z'GGGGZ'Z'Z'AGCCGZ'Z'GZ'GGCACAGAGAAGAAACAAGACC | 1 |
| 2426-66-2 (50-mer) | GAGTGACCGTCTGCCTGCAGCGGGACACAZ'GAGGACZ'Z'GGGGZ'Z'Z'AGCCG | 4 |
| 2426-66-3 (50-mer) | AGTGACCGTCTGCCTGCAGCGGGACACAZ'GAGGACZ'Z'GGGGZ'Z'Z'AGCCGZ' | 5 |
| 2426-66-4 (50-mer) | GTGACCGTCTGCCTGCAGCGGGACACAZ'GAGGACZ'Z'GGGGZ'Z'Z'AGCCGZ'Z' | 6 |
| 2426-66-5 (50-mer) | TGACCGTCTGCCTGCAGCGGGACACAZ'GAGGACZ'Z'GGGGZ'Z'Z'AGCCGZ'Z'G | 7 |
| 2426-66-6 (50-mer) | GACCGTCTGCCTGCAGCGGGACACAZ'GAGGACZ'Z'GGGGZ'Z'Z'AGCCGZ'Z'GT | 8 |
| 2426-66-7 (50-mer) | ACCGTCTGCCTGCAGCGGGACACAZ'GAGGACZ'Z'GGGGZ'Z'Z'AGCCGZ'Z'GZ'G | 9 |
| 2426-66-8 (50-mer) | CCGTCTGCCTGCAGCGGGACACAZ'GAGGACZ'Z'GGGGZ'Z'Z'AGCCGZ'Z'GZ'GG | 10 |
| 2426-66-9 (50-mer) | CGTCTGCCTGCAGCGGGACACAZ'Z'AGGACZ'Z'GGGGZ'Z'Z'AGCCGZ'Z'GZ'GGC | 11 |
| 2426-66-10 (50-mer) | GTCTGCCTGCAGCGGGACACAZ'GAGGACZ'Z'GGGGZ'Z'Z'AGCCGZ'Z'GZ'GGCA | 12 |
| 2426-66-11 (50-mer) | TCTGCCTGCAGCGGGACACAZ'GAGGACZ'Z'GGGGZ'Z'Z'AGCCGZ'Z'GZ'GGCAC | 13 |
| 2426-66-12 (50-mer) | CTGCCTGCAGCGGGACACAZ'GAGGACZ'Z'GGGGZ'Z'Z'AGCCGZ'Z'GZ'GGCACA | 14 |
| 2426-66-13 (50-mer) | TGCCTGCAGCGGGACACAZ'GAGGACZ'Z'GGGGZ'Z'Z'AGCCGZ'Z'GZ'GGCACAG | 15 |
| 2426-66-14 (50-mer) | GCCTGCAGCGGGACACAZ'GAGGACZ'Z'GGGGZ'Z'Z'AGCCGZ'Z'GZ'GGCACAGA | 16 |
| 2426-66-15 (50-mer) | CCTGCAGCGGGACACAZ'GAGGACZ'Z'GGGGZ'Z'Z'AGCCGZ'Z'GZ'GGCACAGAG | 17 |
| 2426-66-16 (50-mer) | CTGCAGCGGGACACAZ'GAGGACZ'Z'GGGGZ'Z'Z'AGCCGZ'Z'GZ'GGCACAGAGA | 18 |
| 2426-66-17 (50-mer) | TGCAGCGGGACACAZ'GAGGACZ'Z'GGGGZ'Z'Z'AGCCGZ'Z'GZ'GGCACAGAGAA | 19 |
| 2426-66-18 (50-mer) | GCAGCGGGACACAZ'GAGGACZ'Z'GGGGZ'Z'Z'AGCCGZ'Z'GZ'GGCACAGAGAAG | 20 |
| 2426-66-19 (50-mer) | CAGCGGGACACAZ'GAGGACZ'Z'GGGGZ'Z'Z'AGCCGZ'Z'GZ'GGCACAGAGAAGA | 21 |
| 2426-66-20 (50-mer) | AGCGGGACACAZ'GAGGACZ'Z'GGGGZ'Z'Z'AGCCGZ'Z'GZ'GGCACAGAGAAGAA | 22 |
| 2426-66-21 (50-mer) | GCGGGACACAZ'GAGGACZ'Z'GGGGZ'Z'Z'AGCCGZ'Z'GZ'GGCACAGAGAAGAAA | 23 |
| 2426-66-22 (50-mer) | CGGGACACAZ'GAGGACZ'Z'GGGGZ'Z'Z'AGCCGZ'Z'GZ'GGCACAGAGAAGAAAC | 24 |
| 2426-66-23 (50-mer) | GGGACACAZ'GAGGACZ'Z'GGGGZ'Z'Z'AGCCGZ'Z'GZ'GGCACAGAGAAGAAACA | 25 |
| 2426-66-24 (50-mer) | GGACACAZ'GAGGACZ'Z'GGGGZ'Z'Z'AGCCGZ'Z'GZ'GGCACAGAGAAGAAACAA | 26 |
| 2426-66-25 (50-mer) | GACACAZ'GAGGACZ'Z'GGGGZ'Z'Z'AGCCGZ'Z'GZ'GGCACAGAGAAGAAACAAG | 27 |
| 2426-66-26 (50-mer) | ACACAZ'GAGGACZ'Z'GGGGZ'Z'Z'AGCCGZ'Z'GZ'GGCACAGAGAAGAAACAAGA | 28 |
| 2426-66-38 (50-mer) | CACAZ'GAGGACZ'Z'GGGGZ'Z'Z'AGCCGZ'Z'GZ'GGCACAGAGAAGAAACAAGAC | 29 |
| 2426-66-39 (50-mer) | ACAZ'GAGGACZ'Z'GGGGZ'Z'Z'AGCCGZ'Z'GZ'GGCACAGAGAAGAAACAAGACC | 30 |

All variants retained β-NGF binding activity with the exception of variants 2426-66-2 (SEQ ID NO: 4), 2426-66-3 (SEQ ID NO: 5), 2426-66-4 (SEQ ID NO: 6), 2426-66-5 (SEQ ID NO: 7), and 2426-66-6 SEQ ID NO: 8), suggesting the 5' terminal 26 nucleotides (positions 1-26) and 3' terminal 21 nucleotides (positions 56-76) of 2426-66 were not required for binding β-NGF, and all or part of the remaining 29 nucleotide element (positions 27-55) may be sufficient. This hypothesis was tested by synthesizing and measuring binding affinities of a second series of variants of 2426-66 (SEQ ID NO: 1). Sequences of the variants are listed in Table 4, wherein Z' represents BndU and T represents dT. All variants retained β-NGF binding activity with the exception of variants 2426-66-56 (SEQ ID NO: 150), 2426-66-57 (SEQ ID NO: 151), 2426-66-58 (SEQ ID NO: 152), and 2426-66-59 (SEQ ID NO: 153). Variant 2426-66-55 (SEQ ID NO: 149), a 25 mer, was the shortest sequence with β-NGF binding affinity equal to the full-length aptamer 2426-66 (SEQ ID NO: 1). Variant 2426-66-54 (SEQ ID NO: 44), a 26 mer, had affinity for β-NGF slightly better than the full length aptamer 2426-66 (SEQ ID NO: 1) and was chosen for further optimization.

TABLE 4

Sequences of Truncated Variants of Aptamer 2426-66

| Aptamer Designation | Sequence (5'→ 3') | SEQ ID NO: |
|---|---|---|
| 2426-66-30 (40-mer) | TGCAGCGGGACACAZ'GAGGACZ'Z'GGGGZ'Z'Z'AGCCGZ'Z'GZ'G | 31 |
| 2426-66-40 (39-mer) | GCAGCGGGACACAZ'GAGGACZ'Z'GGGGZ'Z'Z'AGCCGZ'Z'GZ'G | 32 |
| 2426-66-41 (38-mer) | CAGCGGGACACAZ'GAGGACZ'Z'GGGGZ'Z'Z'AGCCGZ'Z'GZ'G | 33 |
| 2426-66-42 (37-mer) | AGCGGGACACAZ'GAGGACZ'Z'GGGGZ'Z'Z'AGCCGZ'Z'GZ'G | 34 |

TABLE 4-continued

Sequences of Truncated Variants of Aptamer 2426-66

| Aptamer Designation | Sequence (5'→ 3') | SEQ ID NO: |
|---|---|---|
| 2426-66-52 (36-mer) | GCGGGACACAZ'GAGGACZ'Z'GGGGZ'Z'Z'AGCCGZ'Z'GZ'G | 35 |
| 2426-66-43 (35-mer) | CGGGACACAZ'GAGGACZ'Z'GGGGZ'Z'Z'AGCCGZ'Z'GZ'G | 36 |
| 2426-66-44 (34-mer) | GGGACACAZ'GAGGACZ'Z'GGGGZ'Z'Z'AGCCGZ'Z'GZ'G | 37 |
| 2426-66-45 (33-mer) | GGACACAZ'GAGGACZ'Z'GGGGZ'Z'Z'AGCCGZ'Z'GZ'G | 38 |
| 2426-66-46 (32-mer) | GACACAZ'GAGGACZ'Z'GGGGZ'Z'Z'AGCCGZ'Z'GZ'G | 39 |
| 2426-66-47 (31-mer) | ACACAZ'GAGGACZ'Z'GGGGZ'Z'Z'AGCCGZ'Z'GZ'G | 40 |
| 2426-66-48 (30-mer) | CACAZ'GAGGACZ'Z'GGGGZ'Z'Z'AGCCGZ'Z'GZ'G | 41 |
| 2426-66-49 (29-mer) | ACAZ'GAGGACZ'Z'GGGGZ'Z'Z'AGCCGZ'Z'GZ'G | 42 |
| 2426-66-50 (28-mer) | CAZ'GAGGACZ'Z'GGGGZ'Z'Z'AGCCGZ'Z'GZ'G | 2 |
| 2426-66-53 (27-mer) | AZ'GAGGACZ'Z'GGGGZ'Z'Z'AGCCGZ'Z'GZ'G | 43 |
| 2426-66-54 (26-mer) | Z'GAGGACZ'Z'GGGGZ'Z'Z'AGCCGZ'Z'GZ'G | 44 |
| 2426-66-55 (25-mer) | GAGGACZ'Z'GGGGZ'Z'Z'AGCCGZ'Z'GZ'G | 149 |
| 2426-66-56 (24-mer) | AGGACZ'Z'GGGGZ'Z'Z'AGCCGZ'Z'GZ'G | 150 |
| 2426-66-57 (23-mer) | GGACZ'Z'GGGGZ'Z'Z'AGCCGZ'Z'GZ'G | 151 |
| 2426-66-58 (22-mer) | GACZ'Z'GGGGZ'Z'Z'AGCCGZ'Z'GZ'G | 152 |
| 2426-66-59 (21-mer) | ACZ'Z'GGGGZ'Z'Z'AGCCGZ'Z'GZ'G | 153 |

Example 3

Determination of Desirable BndU Positions 26-mer Single Substitution of BndU to dT Nine of the 26 nucleotides of aptamer 2426-66-54 (SEQ ID NO: 44) are BndU. To determine which BndU positions are involved in binding, nine variants of 2426-66-54 were synthesized, each containing a single dT substitution at one of the nine BndU positions and β-NGF affinities were measured. Sequences of the variants are listed in Table 5 wherein Z' represents BndU and T represents dT.

TABLE 5

Sequences of Variants of Aptamer 2426-66-54

| Aptamer Designation | Substitution Position | Sequence (5'→ 3') | SEQ ID NO: |
|---|---|---|---|
| 2426-66-54 | none | Z'GAGGACZ'Z'GGGGZ'Z'Z'AGCCGZ'Z'GZ'G | 44 |
| 2426-66-66 | 1 | TGAGGACZ'Z'GGGGZ'Z'Z'AGCCGZ'Z'GZ'G | 156 |
| 2426-66-67 | 8 | Z'GAGGACT**Z'GGGGZ'Z'Z'AGCCGZ'Z'GZ'G | 157 |
| 2426-66-68 | 9 | Z'GAGGACZ'TGGGGZ'Z'Z'AGCCGZ'Z'GZ'G | 158 |
| 2426-66-69 | 14 | Z'GAGGACZ'Z'GGGGTZ'Z'Z'AGCCGZ'Z'GZ'G | 159 |
| 2426-66-70 | 15 | Z'GAGGACZ'Z'GGGGZ'TZ'AGCCGZ'Z'GZ'G | 160 |
| 2426-66-71 | 16 | Z'GAGGACZ'Z'GGGGZ'Z'TAGCCGZ'Z'GZ'G | 161 |
| 2426-66-72 | 22 | Z'GAGGACZ'Z'GGGGZ'Z'Z'AGCCGTZ'GZ'G | 162 |
| 2426-66-73 | 23 | Z'GAGGACZ'Z'GGGGZ'Z'Z'AGCCGZ'TGZ'G | 163 |
| 2426-66-74 | 25 | Z'GAGGACZ'Z'GGGGZ'Z'Z'AGCCGZ'GTG | 164 |

Substitution of BndU with dT at position 9 (variant 2426-66-68, SEQ ID NO: 158) and position 16 (variant 2426-66-71, SEQ ID NO: 161) showed no loss of affinity for β-NGF compared with the unsubstituted (all BndU) aptamer 2426-66-54 (SEQ ID NO: 44). Substitution of BndU with dT at position 1 (variant 2426-66-66, SEQ ID NO: 156), position 8 (variant 2426-66-67, SEQ ID NO: 157) and position 14 (2426-66-69, SEQ ID NO: 159) showed partial loss of affinity, and substitution at position 15 (2426-66-70, SEQ ID NO: 160), position 22 (2426-66-72, SEQ ID NO: 162), position 23 (2426-66-73, SEQ ID NO: 163) and position 25 (2426-66-74, SEQ ID NO: 164) showed complete loss of affinity. These results indicate that modified uridine residues at positions 1, 8, 14, 15, 22, 23 and 25 are desirable for maximal β-NGF binding affinity Truncated variants of 2426-66 (SEQ ID NO: 1) with BndU residues at positions 9 and 16 replaced with dT were synthesized and tested for affinity to β-NGF. Sequences are listed in Table 6 wherein Z' represents a BndU and T represents dT. Substitution of BndU with dT at two positions showed no loss of affinity compared to unsubstituted controls for any of the three variants.

TABLE 6

Truncated and Substituted Variants of Aptamer 2426-66

| Aptamer Designation | Substitution Positions | Sequence (5'→3') | SEQ ID NO: |
|---|---|---|---|
| 2426-66-75 (28mer) | 11, 18 | CAZ'GAGGACZ'TGGGGZ'Z'TAGCCGZ'Z'GZ'G | 166 |
| 2426-66-76 (27mer) | 10, 17 | AZ'GAGGACZ'TGGGGZ'Z'TAGCCGZ'Z'GZ'G | 167 |
| 2426-66-77 (26mer) | 9, 16 | Z'GAGGACZ'TGGGGZ'Z'TAGCCGZ'Z'GZ'G | 168 |

Based on these results, which are summarized in FIG. 2A, the consensus sequence (SEQ ID NO: 3) for binding to β-NGF was modified as follows to reflect the ability to substitute dT for BndU at two positions:

(SEQ ID NO: 45)
BAZGRGGRSZWGGGGZZWADCCGZZRZG wherein Z, R, S, Z and W are as defined above.

Example 4

Cell Assays

β-NGF aptamer 2426-66 (SEQ ID NO: 1) and truncated variants of 2426-66 were screened for inhibition of β-NGF activity in two in vitro cell assays. PC12 cells (CRL-1721 from ATCC), a cancer cell line from a rat pheochromocytoma and model for neuronal differentiation, respond to β-NGF by induction of the neuronal phenotype. Two manifestations of this response are the phosphorylation of membrane-bound TrkA and the extension of neurites. Aptamers were tested for their ability to inhibit β-NGF-stimulated TrkA phosphorylation and neurite growth of PC12 cells.

Neurite Growth Assays

PC12 cells were plated sparsely in 60 mm dishes and allowed to attach to the plate overnight. After attachment, normal growth medium was replaced with low-serum medium (LSM), as PC12 cells do not differentiate in normal high-serum growth medium. β-NGF (100 ng/mL) and aptamer (100 nM) were pre-mixed in LSM and allowed to equilibrate for one hour, then added to the plates to final concentrations of 10 ng/mL β-NGF (0.38 nM) and 10 nM aptamer. The cells were allowed to incubate for three days, and on day three, the media, (β-NGF, and aptamer were replaced as before. On day 5, images of the cells were captured with a phase-contrast microscope and neurite length was measured using the NeuronJ plugin for ImageJ (NIH program). Neurite length/cell was calculated and normalized to a value of 100 for the no-aptamer control sample (relative to neurite growth).

The ability of aptamers to inhibit human β-NGF induced differentiation of PC12 cells was tested in the Neurite Growth Assay. Aptamers were synthesized with an inverted dT amidite (3'-idT) on the 3' terminus to provide resistance to 3'-5' exonucleases present in the culture medium (see FIG. 5).

Aptamer 2426-66 (SEQ ID NO: 1) and truncated variant 2426-66-50 (SEQ ID NO: 2) effectively inhibited neurite growth induced with β-NGF. Variants 2426-66-53 (SEQ ID NO: 43), 2426-66-54 (SEQ ID NO: 44), and 2426-66-55 (SEQ ID NO: 149) were less effective at inhibiting β-NGF mediated neurite growth than 2426-66-50, indicating a minimum aptamer length of 28 nucleotides was required for maximal inhibition. Variant 2426-66-75 (SEQ ID NO: 166) in which BndU residues at positions 11 and 18 of 2426-66-50 were replaced by dT residues), was also not effective in blocking β-NGF mediated neurite growth. Variant 2426-66-3 (SEQ ID NO: 5), a 50-mer with poor affinity for β-NGF, showed little inhibition of β-NGF mediated neurite growth.

Figure 6:
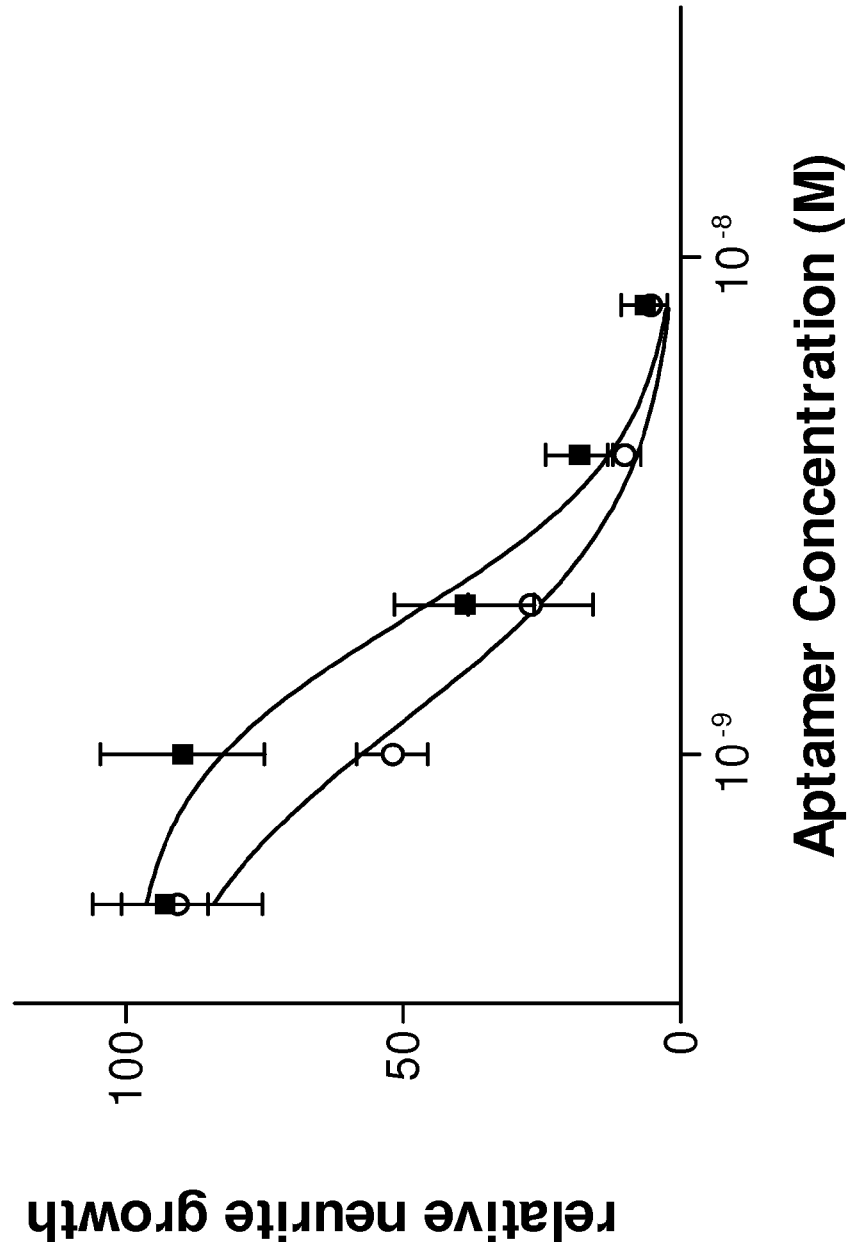
FIG. 6 illustrates graphically the inhibition of β-NGF mediated neurite growth as a function of aptamer concentration for aptamer 2426-66 (■) (SEQ ID NO: 1), and its truncated variant 2426-66-50 (○) (SEQ ID NO: 2), measured as described in Example 4.

The effectiveness of aptamer inhibition of β-NGF mediated neurite growth was determined by measuring relative neurite growth at aptamer concentrations ranging from 0.5 nM to 8.0 nM and calculating the half maximal inhibitory concentration ($IC_{50}$) using a non-linear curve fit (sigmoidal dose response with variable slope) (see FIG. 6). Aptamer 2426-66 (SEQ ID NO: 1) exhibited an $IC_{50}=2\times10^{-9}$ M, and truncated variant 2426-66-50 (SEQ ID NO: 2) exhibited an $IC_{50}=1\times10^{-9}$ M in this assay.

Aptamer 2426-66 (SEQ ID NO: 1) and truncated variants 2426-66-50 (SEQ ID NO: 2) and 2426-66-53 (SEQ ID NO: 43) were tested for inhibition of mouse β-NGF and rat β-NGF in the Neurite Growth Assay. All three inhibited mouse β-NGF nearly as effectively as human β-NGF, and inhibited rat β-NGF to a lesser extent (see FIG. 7).

TrkA Phosphorylation Assay

β-NGF binds to the TrkA receptor on the PC12 cell surface, inducing dimerization and auto-phosphorylation of the receptor. The TrkA Phosphorylation Assay examines the phosphorylation status of TrkA 10 minutes after treatment with β-NGF that has been pre-equilibrated with aptamer. While the Neurite Growth Assay is a terminal assay, looking at the end-point of β-NGF stimulation, the TrkA Phosphorylation Assay is a snapshot of the immediate signaling events following β-NGF stimulation.

PC12 cells were seeded on 100 mm plates and allowed to attach overnight. After attachment, the medium was changed to LSM. The cells were left in LSM overnight, and were then treated for 10 minutes with β-NGF alone (10 ng/mL final concentration, or 0.38 nM), β-NGF with TrkA phosphorylation inhibitor K252a (0.2 μM), and β-NGF pre-equilibrated with aptamer at 10 nM final concentration. Cells were collected, lysed, and TrkA was immuno-precipitated from the cleared lysate with a total Trk antibody (TrkA is the only Trk receptor expressed in PC12 cells). The immuno-precipitate was run on an SDS-PAGE gel, electro-blotted onto a PVDF membrane, and probed with a phospho-tyrosine antibody to quantify the amount of phosphorylated TrkA. The blot was stripped and probed with a TrkA antibody to quantify the amount of total TrkA. Percent TrkA phosphorylation (ratio of phosphorylated TrkA/total TrkA) was calculated for each sample and normalized to a value of 100 for the no-aptamer control. The results are set forth in FIG. 8.

Aptamer 2424-66 (SEQ ID NO: 1) and truncated variants 2426-66-50 (SEQ ID NO: 2) and 2426-66-3 (SEQ ID NO: 5) were tested for inhibition of TrkA phosphorylation by human β-NGF. Aptamer 2426-66 and truncated variant 2426-66-50 effectively inhibited phosphorylation of TrkA receptors induced with β-NGF. Variant 2426-66-3, a 50-mer with poor affinity for β-NGF, showed little inhibition of TrkA phosphorylation by β-NGF.

Variant 2426-66-50 (SEQ ID NO: 2) was tested for inhibition of mouse β-NGF and rat β-NGF in the TrkA phosphorylation Assay. The results are set forth in FIG. 9. Variant 2426-66-50 effectively inhibited both mouse β-NGF and rat β-NGF induced TrkA phosphorylation.

Example 5

Aptamer Treatment of Atopic Dermatitis in Mouse Model System

Inbred NC/NgaTnd mice raised in non-sterile (conventional) circumstances spontaneously develop skin lesions similar to atopic dermatitis lesions in humans and are an established model for investigating treatments for atopic dermatitis (Matsuda et al., Int. Immunol. 9:461, 1997). The following study was designed to assess the ability of NGF-neutralizing aptamers to reduce or eliminate the clinical manifestations of atopic dermatitis in vivo in this mouse model.

NC/NgaTnd mice were maintained in air-uncontrolled conventional circumstances at 20-26° C. with a 12 hour day/night cycle, and given access to standard food and water ad libitum. Mice at the age of 8-10 weeks that manifested mild skin lesions (disease phenotype) were used in this study. NC/NgaTnd mice maintained under specific pathogen free (SPF) conditions and exhibiting no clinical signs or symptoms of atopic dermatitis (no disease phenotype) were used as controls.

Hydrophilic ointment (HO) was prepared according to the Japanese Pharmacopoeia (25% white petrolatum, 20% stearyl alcohol, 12% propylene glycol, 4% polyoxyethylene hydrogenated castor oil 60, 1% glyceryl monostearate, 0.1% methyl parahydroxybenzoate, 0.1% propyl parahydroxybenzoate). Aptamer was prepared in HO by melting 20 g of HO in a water bath at 85° C., adding 20 g of 2% aptamer in water, and mixing in an ice-cold water bath until cool.

Mice were divided into four groups. Group 1 contained 7 mice with dermatitis, untreated. Group 2 contained 7 mice with dermatitis, treated with HO. Group 3 contained 7 mice with dermatitis, treated with aptamer 2426-66-50 (SEQ ID NO: 2) with a 3'-idT (1% w/v in HO). Group 4 contained 7 normal SPF mice, untreated. Mice in groups 2 and 3 were treated once daily for four weeks by applying 100 mg of sample to the affected dorsal areas. Once each week for four weeks (days 0, 7, 14, 21, 28) the scratching behavior and the clinical skin condition score of the mice were quantified.

Spontaneous scratching behavior was quantified using a SCLABA-Real system (Scratch Counting for LABoratory Animals, Noveltec Inc., Kobe, Japan) (Hattori et al., J. Immunol. 184:2729, 2010). Mice were put into the SCLABA instrument 30 minutes before measurement to allow them to adapt to the new environment, and scratching number was counted for one hour in an observation chamber. A series of scratching behaviors, starting with stretching of the hind paws to the head, face, or back and ending with the set-back of the paws, was counted as one bout of scratching.

Clinical skin condition score was determined according to the criteria described in Matsuda et al., Int. Immunol. 9:461, 1997. Observation items were 1) pruritus/itching, 2) erythema/hemorrhage, 3) edema, 4) excoriation/erosion, and 5) scaling/dryness. Scores for each observation item were graded as 0 (none), 1 (mild), 2 (moderate) and 3 (severe). The clinical skin condition score was the sum of the five observation item scores.

Figure 12:
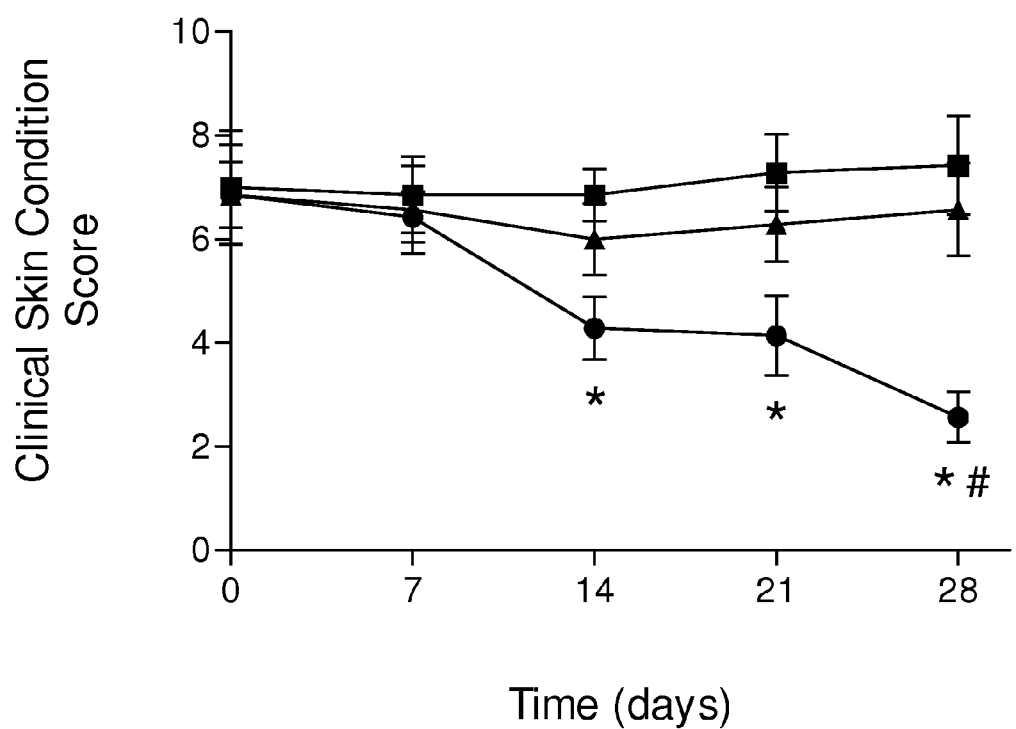
FIG. 12 illustrates graphically the reduction of clinical skin condition score over four weeks in diseased mice treated with aptamer 2426-66-50 (SEQ ID NO: 2), (●), but not in untreated mice (■) or mice treated with HO (▲), as described in Example 5. Statistically significant differences ($p<0.05$) were observed between aptamer treatment and no treatment (*), or aptamer treatment and HO treatment (#), as determined by t-test.

FIG. 11 illustrates the change in scratching frequency for each treatment group, plotted as averages with standard error bars. Scratching frequency decreased steadily from day 14-28 for group 3 (aptamer treatment), but showed no change in frequency over 28 days for groups 1 (no treatment) and 2 (HO treatment). Scratching frequency of group 4 (normal SPF mice) was very low (data not shown). FIG. 12 illustrates the change in clinical skin condition score for each treatment group, plotted as averages with standard error bars. Skin condition score decreased steadily from day 14-28 for group 3 (aptamer treatment), but showed no change over 28 days for groups 1 (no treatment) and 2 (HO treatment). Skin condition score of group 4 (normal SPF mice) was very low (data not shown).

The foregoing embodiments and examples are intended only as examples. No particular embodiment, example, or element of a particular embodiment or example is to be construed as a critical, required, or essential element or feature of any of the claims. Further, no element described herein is required for the practice of the appended claims unless expressly described as "essential" or "critical." Various alterations, modifications, substitutions, and other variations can be made to the disclosed embodiments without departing from the scope of the present invention, which is defined by the appended claims. The specification, including the figures and examples, is to be regarded in an illustrative manner, rather than a restrictive one, and all such modifications and substitutions are intended to be included within the scope of the invention. Accordingly, the scope of the invention should be determined by the appended claims and their legal equivalents, rather than by the examples given above. For example, steps recited in any of the method or process claims may be executed in any feasible order and are not limited to an order presented in any of the embodiments, the examples, or the claims.

TABLE 7

| Diseases with Potential for β-NGF | | | |
|---|---|---|---|
| AIDS dementia complex | Crohn's disease | Interstitial pneumonitis | Pruritis |
| Acquired immune deficiency syndrome (AIDS) | Cryptogenic autoimmune hepatitis | Ionizing radiation exposure | Psoriasis |
| Acquired immunodeficiency syndrome | Cryptogenic fibrosing alveolitis | Iridocyclitis/uveitis/optic neuritis | Psoriasis type 1 |
| Acquired pernicious anemia | Culture negative sepsis | Irritable bowel syndrome | Psoriasis type 2 |
| Acrocyanosis | Cystic fibrosis | Ischemia-reperfusion injury | Psoriatic arthritis |
| Acute and chronic pain (different forms of pain) | Cytokine therapy associated disorders | Ischemic stroke | Psoriatic arthropathy |
| Acute and chronic pain associated with infectious disease (bacterial or viral) | Deafferentation syndromes | Juvenile chronic arthritis | Pulmonary fibrosis |
| Acute immune disease associated with organ transplantation | Dementia pugilistica | Juvenile pernicious anemia | Pulmonary hypertension secondary to connective tissue disease |
| Acute leukemia | Demyelinating disease | Juvenile rheumatoid arthritis | Pulmonary manifestation of polyarteritis nodosa |
| Acute lymphoblastic leukemia (ALL) | Dengue hemorrhagic fever | Juvenile spinal muscular atrophy | Radiation fibrosis |
| Acute myeloid leukemia (AML) | Dental pain | Kaposi's sarcoma | Radiation therapy |
| Acute or chronic immune disease associated with organ transplantation | Dermatitis | Kawasaki's disease | Raynaud's phenomenon and disease |
| Acute pancreatitis | Dermatitis scleroderma | Kidney transplant rejection | Reactive arthritis |
| Acute renal failure | Dermatologic conditions | Legionella | Refsum's disease |
| Acute rheumatic fever | Dermatological diseases | Leishmaniasis | Regular narrow QRS tachycardia |
| Acute transverse myelitis | Dermatomyositis/polymyositis associated lung disease | Leprosy | Reiter's disease |
| Addison's disease | Diabetes | Lesions of the corticospinal system | Renal disease NOS |
| Adenocarcinomas | Diabetes mellitus | Linear IgA disease | Renal diseases |
| Adult (acute) respiratory distress syndrome | Diabetic ateriosclerotic disease | Lipedema | Renovascular hypertension |
| Aerial ectopic beats | Diabetic neuropathy | Liver transplant rejection | Reperfusion injury |
| Alcohol-induced hepatitis | Diffuse Lewy body disease | Lupus | Reperfusion injury after organ transplantation |
| Alcohol-induced liver injury | Dilated cardiomyopathy | Lyme arthritis | Restrictive cardiomyopathy |
| Alcoholic cirrhosis | Dilated congestive cardiomyopathy | Lyme disease | Retinal Degeneration |
| Allergic and atopic diseases | Discoid lupus erythematosus | Lymphederma | Rett Syndrome |
| Allergic conjunctivitis | Disorders of the basal ganglia | Lymphocytic infiltrative lung disease | Rheumatic diseases |
| Allergic contact dermatitis | Disseminated intravascular coagulation | Malaria | Rheumatoid arthritis |
| Allergic diseases | Disturbances of visceral motility at respiratory | Male infertility idiopathic or NOS | Rheumatoid arthritis associated interstitial lung disease |
| Allergic rhinitis | Down's Syndrome in middle age | Malignancies | Rheumatoid spondylitis |
| Allergic skin reactions | Drug sensitivity | Malignant Lymphoma | Sarcoidosis |
| Allergy and asthma | Drug-Induced hepatitis | Malignant histiocytosis | Sarcomas |
| Allograft rejection | Drug-induced interstitial lung disease | Malignant melanoma | Schmidt's syndrome |

TABLE 7-continued

| Diseases with Potential for β-NGF | | | |
|---|---|---|---|
| Alopecia | Drug-induced movement disorders induced by drugs which block CNS dopamine receptors | Memory Disorder | Scleroderma |
| Alopecia areata | Duodenal ulcers | Meningitis | Sciatic neuropathy |
| Alpha-1-antitrypsin deficiency | Dysmenorrhoea | Meningococcemia | Senile Dementia of Lewy body type |
| Alzheimer's disease | Dyspepsia | Mental disorders (e.g., depression and schizophrenia) | Senile chorea |
| Amyotrophic lateral sclerosis | Eczema | Metabolic and idiopathic diseases | Sepsis syndrome |
| Anemia | Encephalomyelitis | Metabolic/idiopathic | Septic arthritis |
| Angina pectoris | Endocarditis | Microscopic vasculitis of the kidneys | Septic shock |
| Ankylosing spondylitis associated lung disease | Endocrinopathy | Migraine | Seronegative arthopathy |
| Anterior horn cell degeneration | Enteropathic synovitis | Mitochondrial multi-system disorder | Shock |
| Anti cd3 therapy | Epilepsy | Mixed connective tissue disease | Sickle cell anemia |
| Anti-receptor hypersensitivity reactions | Epiglottitis | Mixed connective tissue disease associated lung disease | Sjogren's disease associated lung disease |
| Antibody mediated cytotoxicity | Epithelial tissue damage or dysfunction | Mixed-vascular or non-vacular syndromes | Sjogren's syndrome |
| Antiphospholipid syndrome | Epstein-barr virus infection | Monoclonal gammopathy | Skin allograft rejection |
| Aordic and peripheral aneurysims | Erythromelalgia | Multiple myeloma | Skin changes syndrome |
| Aortic dissection | Extrapyramidal and cerebellar disorders | Multiple sclerosis (all subtypes) | Skin complaints with inflammatory components |
| Arterial hypertension | Extramammary Paget's disease | Multiple systems degenerations (Mencel Dejerine-Thomas Shi-Drager and Machado-Joseph) | Small bowel transplant rejection |
| Arteriosclerosis | Familial hematophagocytic lymphohistiocytosis | Myalgic encephalitis/Royal Free Disease | Solid and liquid tumor pathologies |
| Arteriovenous fistula | Female infertility | Myasthenia gravis | Solid tumors |
| Arthritis | Fetal thymus implant rejection | Mycobacterium avium intracellulare | Specific arrythmias |
| Arthropathy | Fibromyalgia | Mycobacterium tuberculosis | Sperm autoimmunity |
| Asthenia | Fibrosis | Myelodyplastic syndrome | Spinal ataxia |
| Asthma | Fibrotic lung disease | Myocardial infarction | Spinocerebellar degenerations |
| Ataxia | Friedreich's ataxia | Myocardial ischemic disorders | Spondyloarthopathy |
| Atheromatous disease/arteriosclerosis | Functional peripheral arterial disorders | Myositis | Sporadic |
| Atherosclerosis | Fungal sepsis | β-NGF-related pain and hyperalgesia | Still's disease |
| Atopic allergy | Gas gangrene | Nasopharyngeal carcinoma | Streptococcal myositis |
| Atopic dermatitis | Gastric ulcer | Neonatal chronic lung disease | Stroke |
| Atrial fibrillation (sustained or paroxysmal) | Gastroesophageal reflux | Nephritis | Structural lesions of the cerebellum |
| Atrial flutter | Gastrointestinal or vascular regions | Nephrosis | Subacute sclerosing panencephalitis |
| Atrioventricular block | General gastrointestinal disorders | Nephrotic syndrome | Sunburn |

TABLE 7-continued

Diseases with Potential for β-NGF

| | | | |
|---|---|---|---|
| Atrophic autoimmune hypothyroidism | General headache | Neuritis | Surgical pain |
| Autoimmune bullous disease | General inflammation | Neurodegenerative diseases | Sympathetic ophthalmia |
| Autoimmune diseases | Genitourinary | Neurogenic I muscular atrophies | Sympathetically maintained pain |
| Autoimmune haemolytic anemia | Giant cell arteritis | Neurological diseases | Syncope |
| Autoimmune hepatitis | Glomerular nephritis | Neuropathic pain | Syphilis of the cardiovascular system |
| Autoimmune mediated hypoglycemia | Goitrous autoimmune hypothyroidism (Hashimoto's disease) | Neuropathic pain and associated hyperalgesia and allodynia | Systemic anaphalaxis |
| Autoimmune neutropenia | Goodpasture's syndrome | Neuropathic pain and associated hyperalgesia or allodynia | Systemic inflammatory response syndrome |
| Autoimmune thrombocytopenia | Gouty arthritis | Neutropenic fever | Systemic lupus erythematosus |
| Autoimmune thyroid disease | Graft rejection of any organ or tissue | Non-alcoholic Steatohepatitis | Systemic lupus erythematosus associated lung disease |
| B cell lymphoma | Glaucoma | Non-hodgkins lymphoma | Systemic onset juvenile rheumatoid arthritis |
| Bone graft rejection | Gram negative sepsis | Obstetric and gynecologic diseases | Systemic sclerosis |
| Bone marrow transplant (BMT) rejection | Gram positive sepsis | Occlusion of the abdominal aorta and its branches | Systemic sclerosis associated interstitial lung disease |
| Bronchial disorders | Granulomas due to intracellular organisms | Occulsive arterial disorders | T-cell or FAB ALL |
| Bronchiolitis obliterans | Grave's disease | Okt3 therapy | Takayasu's disease/arteritis |
| Bundle branch block | Group B streptococci (GBS) infection | Opthalmological diseases | Telangiectasia |
| Burkitt's lymphoma | HIV | Orchitis/epidymitis | Tension headache |
| Burns | HIV neuropathy | Orchitis/vasectomy reversal procedures | Th2 Type and Th1 Type mediated diseases |
| Cachexia | Haemosiderosis associated lung disease | Organ transplant rejection | Thalamic pain syndrome |
| Cancer | Hairy cell leukemia | Organomegaly | Thromboangitis obliterans |
| Cardiac arrhythmias | Hallerrorden-Spatz disease | Osteoarthritis | Thrombocytopenia |
| Cardiac stun syndrome | Hashimoto's thyroiditis | Osteoarthrosis | Thyroiditis |
| Cardiac tumors | Hay fever | Osteoporosis | Toxic shock syndrome |
| Cardiomyopathy | Heart failure | Diseases of airway inflammation | Toxicity |
| Cardiopulmonary bypass inflammation response | Heart transplant rejection | Ovarian failure | Toxins |
| Cardiovascular affections | Hemachromatosis | POEMS syndrome (polyneuropathy, organomegaly, endocrinopathy, monoclonal gammopathy, and skin changes syndrome) | Toxins and chemotherapy |
| Carditis | Hematopoietic malignancies (leukemia and lymphoma) Abetalipoprotemia | Pain | Transplant rejection diseases |
| Cartilage transplant rejection | Hemodialysis | Pain from amputation or abscess | Transplants |
| Causalgia | Hemolytic anemia | Pain from trauma | Trauma/hemorrhage |
| Cerebellar cortical degenerations | Hemolytic uremic syndrome/thrombolytic thrombocytopenic purpura, hemorrhage | Pancreas transplant rejection | Trigeminal neuralgia |

TABLE 7-continued

| Diseases with Potential for β-NGF | | | |
|---|---|---|---|
| Cerebellar disorders | Henoch-Schoenlein purpurea | Pancreatic carcinoma | Type B insulin resistance with acanthosis nigricans |
| Chaotic or multifocal atrial tachycardia | Hepatitis A | Pancreatitis | Type III hypersensitivity reactions |
| Chemotherapy | Hepatitis B | Paraneoplastic syndrome/hypercalcemia of malignancy | Type IV hypersensitivity |
| Cerebral Infarction | Hepatitis C | Parasitic diseases | Type-1 autoimmune hepatitis (classical autoimmune or lupoid hepatitis) |
| Chlamydia | Herpes simplex | Parathyroid transplant rejection | Type-2 autoimmune hepatitis (anti-LKM antibody hepatitis) |
| Choleosatatis | His bundle arrythmias | Parkinson's disease | Ulcerative colitic arthropathy |
| Chromic myelocytic leukemia (CML) | Hodgkin's disease | Pelvic inflammatory disease | Ulcerative colitis |
| Chronic active hepatitis | Huntington's chorea | Pemphigoid | Unstable angina |
| Chronic alcoholism | Hyperkinetic movement disorders | Pemphigus foliaceus | Uremia |
| Chronic eosinophilic pneumonia | Hypersensitivity reactions | Pemphigus vulgaris | Urosepsis |
| Chronic fatigue syndrome | Hypersensitivity pneumonitis | Perennial rhinitis | Urticaria |
| Chronic immune disease associated with organ transplantation | Hypertension | Pericardial disease | Uveitis |
| Chronic inflammatory conditions | Hyperthyroidism | Peripheral atherlosclerotic disease | Valvular heart diseases |
| Chronic inflammatory pain or neuropathic pain | Hypokinetic movement disorders | Peripheral vascular disorders | Varicose veins |
| Chronic inflammatory pathologies | Hypoglycemia | Peritonitis | Vasculitic diffuse lung disease |
| Chronic liver diseases | Hypoparathyroidism | Pernicious anemia | Vasculitis |
| Chronic lymphocytic leukemia (CLL) | Hypothalamic-pituitary-adrenal axis evaluation | Phacogenic uveitis | Vasomotor or allergic rhinitis |
| Chronic mucocutaneous candidiasis | Iatrogenic intoxication conditions | Pneumocystis carinii pneumonia | Venous diseases |
| Chronic obstructive pulmonary disease | Idiopathic Addison's disease | Pneumonia | Venous thrombosis |
| Chronic obstructive pulmonary disease (COPD) | Idiopathic leucopenia | Polyglandular deficiency type I and polyglandular deficiency type II | Ventricular fibrillation |
| Chronic salicylate intoxication | Idiopathic pulmonary fibrosis | Post herpetic neuralgia | Viral and fungal infections |
| Chronic visceral pain | Idiopathic thrombocytopenia | Post perfusion syndrome | Visceralgia or irritable bowel syndrome |
| Cluster headache | Idiosyncratic liver disease | Post pump syndrome | Vital encephalitis/aseptic meningitis |
| Colitis | Post-surgical pain | Post-MI cardiotomy syndrome | Vital-associated hemaphagocytic syndrome |
| Collagen vascular diseases | Infantile spinal muscular atrophy | Post-inflammatory interstitial lung disease | Vitiligo |
| Colorectal carcinoma | Infectious diseases | Postinfectious interstitial lung disease | Vitiligo acute liver disease |
| Common varied immunodeficiency (common variable hypogammaglobulinemia) | Inflammation of the aorta | Preeclampsia | Wallerian Degeneration |
| Congenital diseases | Inflammatory bowel disease | Premature ovarian failure | Wegener's granulomatosis |
| Congestive heart failure | Inflammatory bowel disorders | Primary biliary cirrhosis | Wernicke-Korsakoff syndrome |
| Conjunctivitis | Inflammatory diseases | Primary myxoedema | Wilson's disease |

TABLE 7-continued

Diseases with Potential for β-NGF

| | | | |
|---|---|---|---|
| Connective tissue disease associated interstitial lung disease | Inflammatory eye disorders | Primary pulmonary hypertension | Wounds |
| Contact dermatitis | Inflammatory or unstable bladder disorders | Primary sclerosing cholangitis | Xenograft rejection of any organ or tissue |
| Coombs positive hemolytic anemia | Inflammatory pain | Primary sclerosing hepatitis | Yersinia and salmonella associated arthropathy |
| Cor pulmonale | Inflammatory pain and associated hyperalgesia and allodynia | Primary vasculitis | |
| Coronary artery disease | Influenza A | Progressive supranucleo Palsy | |
| Creutzfeldt-Jakob disease | Insulin dependent diabetes mellitus | | |

What is claimed is:

1. An aptamer comprised of the sequence $$BAZGRGGRSN_{(0-1)}ZWGGGGN_{(0-1)}ZZWADCCGZZRZG$$ (SEQ ID NO: 154)

wherein

B is selected from a C, G or Z;

R is independently selected from an A or G;

S is selected from a C or G;

W is independently selected from a Z or T;

D is selected from an A, G or Z;

N is independently selected from any naturally occurring or modified nucleotide and Z is independently selected from a modified pyrimidine.

2. The aptamer of claim 1, wherein the aptamer binds to β-NGF.

3. The aptamer of claim 2, wherein the aptamer inhibits the function of β-NGF.

4. The aptamer of claim 2, wherein said aptamer has the ability to modulate the binding of β-NGF to its one or more of its cellular receptors.

5. The aptamer of claim 4 wherein said cellular receptor is selected from p75 or TrkA.

6. The aptamer of claim 2, wherein the aptamer comprises a $K_d$ for β-NGF of 30 nM or less.

7. The aptamer of claim 1, wherein said modified pyrimidine is a C-5 modified pyrimidine.

8. The aptamer of claim 7, wherein the C-5 modified pyrimidine is selected from the group consisting of the following compounds:

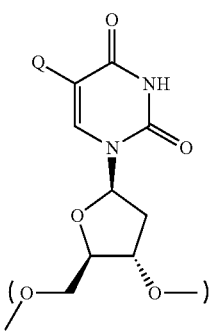
U

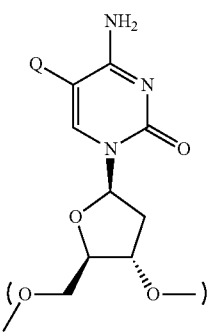
C

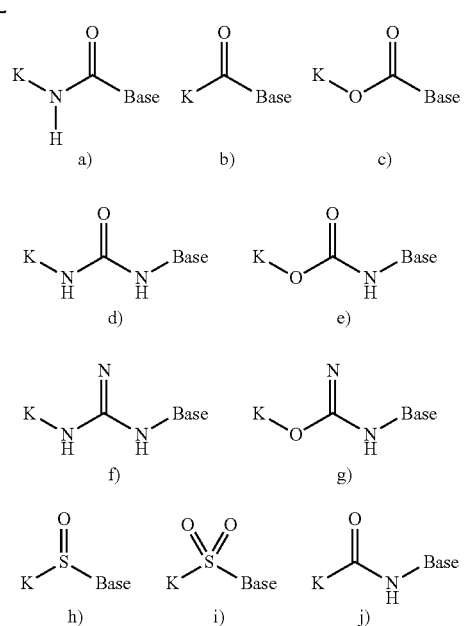

Base = Uridine (U) or Cytidine (C) (attachment is to the 5-position)
K = R' group plus $(CH_2)_n$ connecting group, where n = 0-3

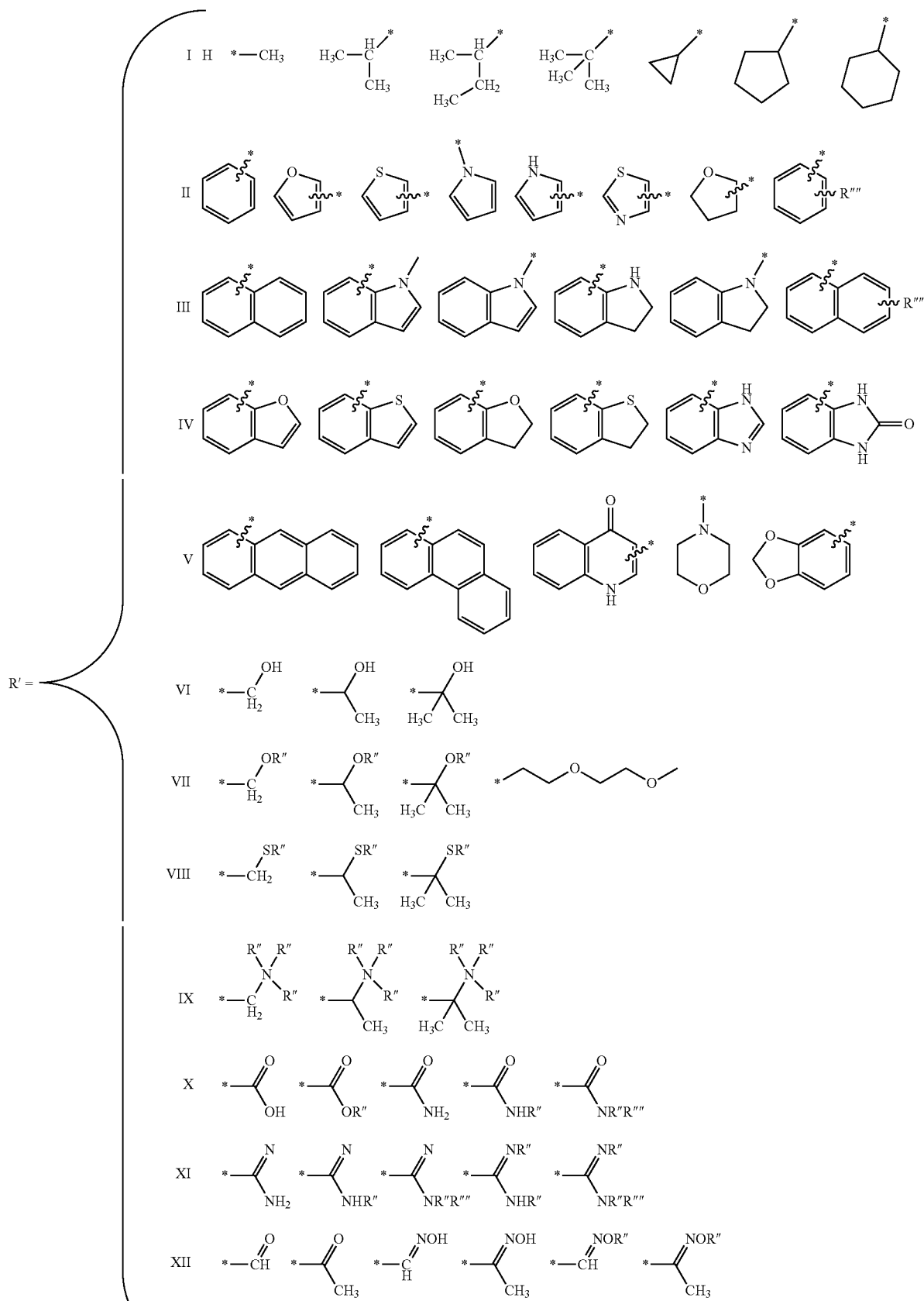
*Denotes point of attachment of the R' group to (CH₂)ₙ connecting group wherein R"" is selected from the group consisting of a branched or linear lower alkyl (C1-C20); halogen (F, Cl, Br, I); nitrile (CN); boronic acid (BO₂H₂); carboxylic acid (COOH); carboxylic acid ester (COOR"); primary amide (CONH₂); secondary amide (CONHR"); tertiary amide (CONR"R'"); sulfonamide (SO₂NH₂); N-alkylsulfonamide (SONHR");

wherein

R", R'" are independently selected from a group consisting of a branched or linear lower alkyl (C1-C2)); phenyl (C₆H₅); an R"" substituted phenyl ring (R""C₆H₄); wherein R"" is defined above; a carboxylic acid (COOH); a carboxylic acid ester (COOR""); wherein R"" is a branched or linear lower alkyl (C1-C20); and cycloalkyl; wherein R"=R'"=(CH₂)n; and wherein n=2-10.

9. The aptamer of claim 7, wherein the C-5 modified pyrimidine is selected from the group consisting of 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU) and 5-(N-naphthylmethylcarboxyamide)-2'-deoxyuridine (NapdU).

10. The aptamer of claim 7, wherein the C-5 modified pyrimidine is 5-(N-benzylcarboxyamide)-2'-deoxyuridine (BndU).

11. The aptamer of claim 1, wherein said aptamer has the following sequence:

(SEQ ID NO: 45)
BAZGRGGRSZWGGGGZZWADCCGZZRZG.

12. An aptamer comprised of the sequence (SEQ. ID. NO: 3)
BAZGRGGRSZZGGGGZZZADCCGZZRZG, wherein B is selected from a C, G or Z;
R is independently selected from an A or G;
S is selected from a C or G;
D is selected from an A, G or Z; and
Z is independently selected from a modified pyrimidine.

13. An aptamer that binds to β-NGF comprising a sequence selected from the group consisting of SEQ. ID. NOS: 1, 2, 9-44 and 149.

14. The aptamer of claim 13, wherein the aptamer inhibits the function of β-NGF.

15. The aptamer of claim 13, wherein said aptamer has the ability to modulate the binding of β-NGF to its one or more of its cellular receptors.

16. The aptamer of claim 15, wherein said cellular receptor is selected from p75 or TrkA.

17. The aptamer of claim 16, wherein the sequence has at least about 90% identity, at least about 91% identity, at least about 92% identity, at least about 93% identity, at least about 94% identity, or at least about 95% identity.

* * * * *

UNITED STATES PATENT AND TRADEMARK OFFICE
CERTIFICATE OF CORRECTION

PATENT NO. : 8,598,140 B2
APPLICATION NO. : 13/634618
DATED : December 3, 2013
INVENTOR(S) : Daniel J. Schneider et al.

It is certified that error appears in the above-identified patent and that said Letters Patent is hereby corrected as shown below:

In the Claims

In claim 8, at Columns 201-202, replace the structure with the following:

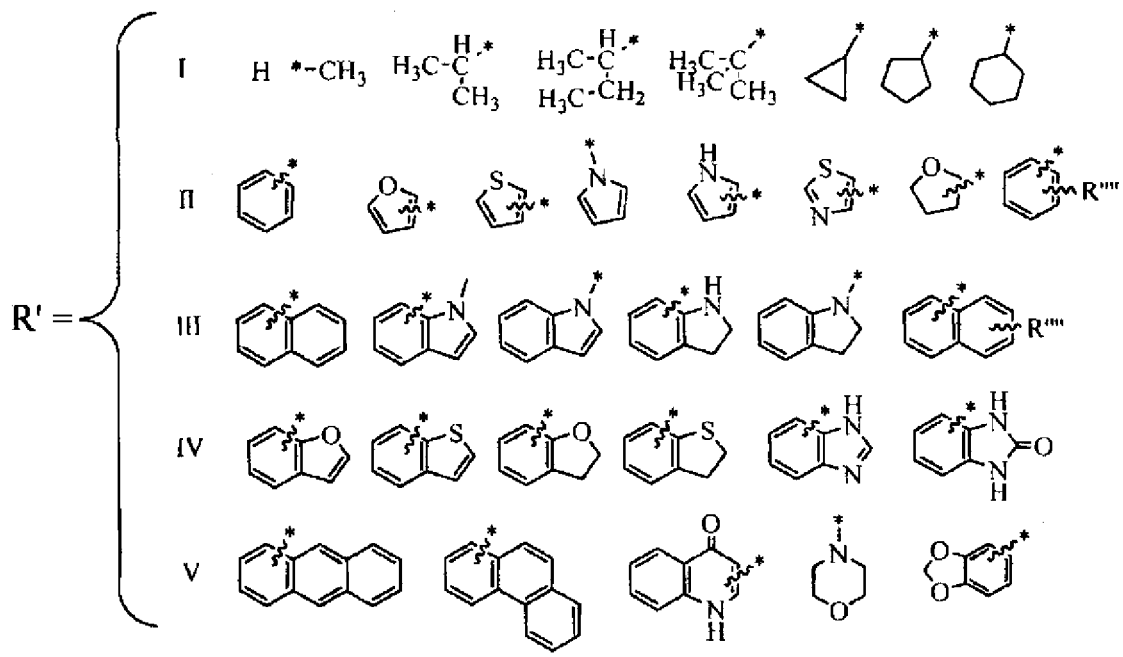

Signed and Sealed this
Thirtieth Day of December, 2014

Michelle K. Lee
*Deputy Director of the United States Patent and Trademark Office*

CERTIFICATE OF CORRECTION (continued)
U.S. Pat. No. 8,598,140 B2

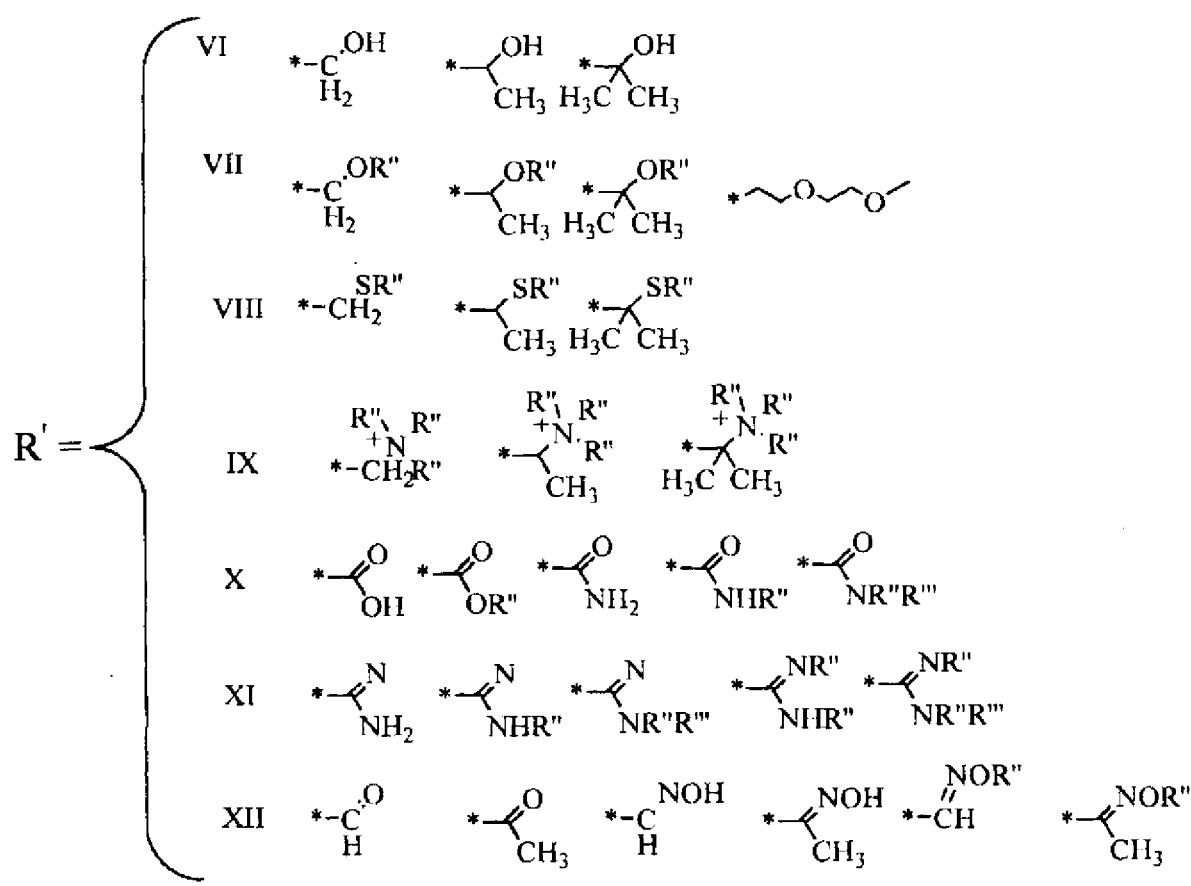

*Denotes point of attachment of the R' group to $(CH_2)_n$ connecting group